US011345722B2

(12) United States Patent
Hollander et al.

(10) Patent No.: US 11,345,722 B2
(45) Date of Patent: *May 31, 2022

(54) HIGH PH PROTEIN REFOLDING METHODS

(71) Applicant: BRISTOL-MYERS SQUIBB COMPANY, Princeton, NJ (US)

(72) Inventors: Cristopher Hollander, West Newton, MA (US); Benjamin C. Blum, Boston, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 802 days.

This patent is subject to a terminal disclaimer.

(21) Appl. No.: 16/050,417

(22) Filed: Jul. 31, 2018

(65) Prior Publication Data

US 2019/0077828 A1 Mar. 14, 2019

Related U.S. Application Data

(63) Continuation of application No. 14/766,848, filed as application No. PCT/US2014/015702 on Feb. 11, 2014, now Pat. No. 10,065,987.

(60) Provisional application No. 61/763,664, filed on Feb. 12, 2013.

(51) Int. Cl.
C07K 1/113 (2006.01)
C12P 21/02 (2006.01)
C07K 14/78 (2006.01)

(52) U.S. Cl.
CPC .......... C07K 1/1136 (2013.01); C07K 1/1133 (2013.01); C07K 14/78 (2013.01); C12P 21/02 (2013.01); C07K 2319/30 (2013.01); C07K 2319/70 (2013.01)

(58) Field of Classification Search
CPC ................ C07K 1/1136; C07K 1/1133; C07K 2319/30; C07K 2319/70; C12P 21/02
See application file for complete search history.

(56) References Cited

U.S. PATENT DOCUMENTS

| 5,340,926 | A | 8/1994 | Lowe et al. |
| 6,001,604 | A | 12/1999 | Hartman et al. |
| 6,670,148 | B2 | 12/2003 | Mundschenk |
| 6,818,418 | B1 | 11/2004 | Lipovsek et al. |
| 7,115,396 | B2 | 10/2006 | Lipovsek et al. |
| 7,556,925 | B2 | 7/2009 | Koide et al. |
| 7,598,352 | B2 | 10/2009 | Koide |
| 7,847,062 | B2 | 12/2010 | Chen et al. |
| 7,858,739 | B2 | 12/2010 | Chen et al. |
| 8,067,201 | B2 | 11/2011 | Morin et al. |
| 8,221,765 | B2 | 7/2012 | Camphausen et al. |
| 8,258,265 | B2 | 9/2012 | Koide |
| 8,263,741 | B2 | 9/2012 | Koide |
| 8,278,419 | B2 | 10/2012 | Jacobs et al. |
| 8,293,482 | B2 | 10/2012 | Jacobs et al. |
| 8,324,362 | B2 | 12/2012 | Chen et al. |
| 9,416,170 | B2 | 8/2016 | Davis et al. |
| 10,065,987 | B2 | 9/2018 | Hollander et al. |
| 10,183,967 | B2 | 1/2019 | Blum et al. |
| 11,053,278 | B2 | 7/2021 | Blum et al. |
| 2002/0019517 | A1 | 2/2002 | Koide |
| 2003/0170753 | A1 | 9/2003 | Koide |
| 2003/0186385 | A1 | 10/2003 | Koide |
| 2005/0038229 | A1 | 2/2005 | Lipovsek et al. |
| 2005/0255548 | A1 | 11/2005 | Lipovsek et al. |
| 2006/0210604 | A1 | 9/2006 | Dadey et al. |
| 2006/0246059 | A1 | 11/2006 | Lipovsek et al. |
| 2006/0270604 | A1 | 11/2006 | Lipovsek et al. |
| 2007/0082365 | A1 | 4/2007 | Lipovsek et al. |
| 2008/0015339 | A1 | 1/2008 | Lipovsek et al. |
| 2008/0063651 | A1 | 3/2008 | Lipovsek et al. |
| 2008/0108798 | A1 | 5/2008 | Lipovsek et al. |
| 2008/0125580 | A1* | 5/2008 | Pizarro ................... C07K 14/00 530/399 |
| 2008/0139791 | A1 | 6/2008 | Lipovsek et al. |
| 2008/0220049 | A1 | 9/2008 | Chen et al. |
| 2009/0042248 | A1* | 2/2009 | Gal ....................... C12N 9/6424 435/69.1 |
| 2009/0176654 | A1 | 7/2009 | Cappuccilli et al. |
| 2010/0081792 | A1 | 4/2010 | Grant et al. |
| 2010/0144601 | A1 | 6/2010 | Jacobs et al. |

(Continued)

FOREIGN PATENT DOCUMENTS

| EP | 1266025 B1 | 11/2006 |
| EP | 1137941 B1 | 8/2009 |

(Continued)

OTHER PUBLICATIONS

Ackermann, Maximilian et al., "Anti-VEGFR2 and anti-IGF-1R-Adnectins inhibit Ewing's sarcoma A673-xenograft growth and normalize tumor vascular architecture," Angiogenesis, vol. 15:685-695 (2012).
Application No. EP 17187867.1 European Search Report dated Nov. 23, 2017.
Batori, Vincent et al., "Exploring the potential of the monobody scaffold: effects of loop elongation on the stability of a fibronectin type III domain," Protein Engineering, vol. 15(12):1015-1020 (2002).
Carlk "Protein refolding for industrial processes" Current Opinion in Biotechnology 12:202-207 (Year: 2001).
Cota, Ernesto et al., "Folding of beta-sandwich proteins: Three-state transition of a fibronectin type III module," Protein Science, vol. 9:112-120 (2000).

(Continued)

Primary Examiner — Daniel E Kolker
Assistant Examiner — James L Rogers
(74) Attorney, Agent, or Firm — Nelson Mullins Riley & Scarborough, LLP; Jane E. Remillard, Esq.; Christopher L. Frank

(57) ABSTRACT

Provided herein are methods for refolding denatured protein (e.g., from inclusion bodies) that do not require the use of a denaturing agent. Exemplary methods use a high pH for solubilizing denatured protein, followed by a decrease in pH for refolding the proteins.

14 Claims, 14 Drawing Sheets
Specification includes a Sequence Listing.

(56) References Cited

U.S. PATENT DOCUMENTS

| | | | |
|---|---|---|---|
| 2010/0152063 A1* | 6/2010 | Cappuccilli | C12N 15/1044 506/17 |
| 2010/0273216 A1 | 10/2010 | Morin et al. | |
| 2010/0298541 A1 | 11/2010 | Wu et al. | |
| 2010/0322930 A1 | 12/2010 | Kolbinger et al. | |
| 2011/0021746 A1 | 1/2011 | Cappuccilli et al. | |
| 2011/0038866 A1 | 2/2011 | Hastewell et al. | |
| 2011/0123545 A1 | 5/2011 | Marsh et al. | |
| 2011/0124527 A1 | 5/2011 | Cappuccilli et al. | |
| 2011/0237509 A1* | 9/2011 | Skinner | C12P 21/06 514/11.4 |
| 2011/0274623 A1 | 11/2011 | Jacobs | |
| 2011/0275535 A1 | 11/2011 | Loew | |
| 2011/0284623 A1 | 11/2011 | Jones et al. | |
| 2012/0208704 A1 | 8/2012 | Loew et al. | |
| 2012/0270797 A1 | 10/2012 | Wittrup et al. | |
| 2013/0079243 A1 | 3/2013 | Diem et al. | |
| 2013/0079280 A1 | 3/2013 | Baca et al. | |
| 2013/0096019 A1 | 4/2013 | Jacobs et al. | |
| 2013/0096058 A1 | 4/2013 | Baca et al. | |
| 2013/0196871 A1 | 8/2013 | Davis et al. | |
| 2013/0237684 A1 | 9/2013 | Koide | |
| 2013/0245238 A1 | 9/2013 | Davis et al. | |
| 2013/0267676 A1 | 10/2013 | Koide | |
| 2014/0057807 A1 | 2/2014 | Loew et al. | |
| 2015/0376229 A1 | 12/2015 | Blum et al. | |
| 2019/0016922 A1 | 1/2019 | Moran | |

FOREIGN PATENT DOCUMENTS

| | | | | |
|---|---|---|---|---|
| EP | 2141243 | A2 | 1/2010 | |
| EP | 2154535 | A1 | 2/2010 | |
| EP | 2385067 | A1 | 11/2011 | |
| EP | 2439212 | A1 | 4/2012 | |
| EP | 2379718 | B1 | 3/2013 | |
| KR | 100247151 | B1 | 3/2000 | |
| KR | 20020011559 | A | 2/2002 | |
| KR | 20020011559 | A * | 2/2002 | C12N 15/00 |
| KR | 96001339 | B1 | 10/2006 | |
| WO | 199202540 | A1 | 2/1992 | |
| WO | 199204382 | A1 | 3/1992 | |
| WO | 9831700 | A1 | 7/1998 | |
| WO | 9856915 | A2 | 12/1998 | |
| WO | 9951773 | A1 | 10/1999 | |
| WO | 2000/34784 | A1 | 6/2000 | |
| WO | 2001/64942 | A1 | 9/2001 | |
| WO | 2002/04523 | A2 | 1/2002 | |
| WO | 2002/32925 | A2 | 4/2002 | |
| WO | 2002/081497 | A2 | 10/2002 | |
| WO | 2003/104418 | A2 | 12/2003 | |
| WO | 2003102013 | A2 | 12/2003 | |
| WO | 2004001056 | A1 | 12/2003 | |
| WO | WO-03102013 | A2 * | 12/2003 | C07K 14/4716 |
| WO | 2004015124 | A1 | 2/2004 | |
| WO | 2005056764 | A2 | 6/2005 | |
| WO | 2008066752 | A2 | 6/2008 | |
| WO | 2008097497 | A2 | 8/2008 | |
| WO | 2008/153745 | A2 | 12/2008 | |
| WO | 2009023184 | A2 | 2/2009 | |
| WO | 2009025806 | A2 | 2/2009 | |
| WO | 2009058379 | A2 | 5/2009 | |
| WO | 2009073115 | A1 | 6/2009 | |
| WO | 2009083804 | A2 | 7/2009 | |
| WO | 2009086116 | A2 | 7/2009 | |
| WO | 2009102421 | A2 | 8/2009 | |
| WO | 2009133208 | A1 | 11/2009 | |
| WO | 2009142773 | A2 | 11/2009 | |
| WO | 2010051274 | A2 | 5/2010 | |
| WO | 2010051310 | A2 | 5/2010 | |
| WO | 2010060095 | A1 | 5/2010 | |
| WO | 2010069913 | A1 | 6/2010 | |
| WO | 2010092233 | A1 | 8/2010 | |
| WO | 2010093627 | A2 | 8/2010 | |
| WO | 2010093771 | A1 | 8/2010 | |
| WO | 2011020033 | A2 | 2/2011 | |
| WO | 2011035202 | A2 | 3/2011 | |
| WO | 2011051333 | A1 | 5/2011 | |
| WO | 2011051466 | A1 | 5/2011 | |
| WO | 2011092233 | A1 | 8/2011 | |
| WO | 2011100700 | A2 | 8/2011 | |
| WO | 2011103105 | A1 | 8/2011 | |
| WO | 2011130324 | A1 | 10/2011 | |
| WO | 2011130328 | A1 | 10/2011 | |
| WO | 2011130354 | A1 | 10/2011 | |
| WO | 2011137319 | A2 | 11/2011 | |
| WO | 2011140086 | A2 | 11/2011 | |
| WO | 2011150133 | A2 | 12/2011 | |
| WO | 2012016245 | A2 | 2/2012 | |
| WO | 2012088006 | A1 | 6/2012 | |
| WO | 2012094653 | A2 | 7/2012 | |
| WO | 2012142515 | A2 | 10/2012 | |
| WO | WO-2012142515 | A2 * | 10/2012 | C07K 7/08 |
| WO | 2012158678 | A1 | 11/2012 | |
| WO | 2012158739 | A1 | 11/2012 | |
| WO | 2013049275 | A1 | 4/2013 | |
| WO | 2013/067029 | A2 | 5/2013 | |
| WO | 2014043344 | A1 | 3/2014 | |
| WO | 2014120891 | A2 | 8/2014 | |

OTHER PUBLICATIONS

Cota, Ernesto et al., "Two Proteins with the Same Structure Respond very Differently to Mutation: The Role of Plasticity in Protein Stability," J. Mol. Biol., vol. 302:713-725 (2000).

Dickinson, Craig D. et al., "Crystal Structure of the Tenth Type III Cell Adhesion Module of Human Fibronectin," J. Mol. Biol., vol. 236:1079-1092 (1994).

Dickinson, Craig D. et al., "Crystals of the Cell-binding Module of Fibronectin Obtained from a Series of Recombinant Fragments Differing in Length," J. Mol. Biol., vol. 238:123-127 (1994).

Dutta, Sanjib et al., "High-affinity fragment complementation of a fibronectin type III domain and its application to stability enhancement," Protein Science, vol. 14:2838-2848 (2005).

Dutta, Sanjib et al., "High-throughput analysis of the protein sequence-stability landscape using a quantitative 'yeast surface two-hybrid' system and fragment reconstitution," J. Mol. Biol., vol. 382(3):721-733 (2008).

Getmanova, Elena V. et al., "Antagonists to Human and Mouse Vascular Endothelial Growth Factor Receptor 2 Generated by Directed Protein Evolution In Vitro," Chemistry & Biology, vol. 13:549-556 (2006).

Gilbreth, Ryan N. et al., "A Dominant Conformational Role for Amino Acid Diversity in Minimalist Protein-Protein Interfaces," J. Mol. Biol., vol. 381(2):407-418 (2008).

Gilbreth, Ryan N. et al., "Isoform-specific monobody inhibitors of small ubiquitin-related modifiers engineered using structure-guided library design," PNAS, vol. 108(19):7751-7756 (2011).

Hackel, Benjamin J. et al., "Picomolar Affinity Fibronectin Domains Engineered Utilizing Loop Length Diversity, Recursive Mutagenesis, and Loop Shuffling," J. Mol Biol., vol. 381:1238-1252 (2008).

Patra, A.K., et al., "Optimization of Inclusion Body Solubilization and Renaturation of Recombinant Human Growth Hormone from *Escherichia coli*," Protein Expression and Purification, vol. 18, No. 2, pp. 182-192 (Mar. 2000).

Rudolph, R., et al., "In vitro folding of inclusion body proteins," The FASEB Journal, vol. 10, No. 1, pp. 49-56 (Jan. 1996).

Vallejo et al. "Strategies for the recovery of active proteins through refolding of bacterial inclusion body proteins" Microbial Cell Factories 2004, 3: 11 (Year: 2004).

Walsh, Daniel J., et al., "Non-Reducing Alkaline Solubilization and Rapid On-Column Refolding of Recombinant Prion Protein," Preparation Biochemistry & Biotechnology, vol. 42, No. 1, pp. 77-86 (Jan. 2012).

Zhizhou, Z., et al., "Mechanism of enhancement of prochymosin renaturation by solubilization of inclusion bodies at alkaline pH," Science in China (Series C) Life Sciences, vol. 40, No. 2, pp. 169-175, (Apr. 2007).

(56) References Cited

OTHER PUBLICATIONS

U.S. Appl. No. 16/211,094, filed Dec. 5, 2018, Benjamin C. Blum.
U.S. Appl. No. 16/211,094, Mar. 5, 2021.
U.S. Appl. No. 16/211,094, Nov. 17, 2020.
U.S. Appl. No. 16/211,094, Aug. 6, 2020.
U.S. Appl. No. 16/211,094, Jan. 8, 2020.
U.S. Appl. No. 14/766,848, filed Aug. 10, 2015, Cristopher Hollander.
U.S. Appl. No. 14/766,849, filed Aug. 10, 2015, Benjamin C. Blum.
U.S. Appl. No. 14/766,848, May 1, 2018.
U.S. Appl. No. 14/766,848, Oct. 5, 2017.
U.S. Appl. No. 14/766,848, Jul. 11, 2017.
U.S. Appl. No. 14/766,849, Sep. 6, 2018.
U.S. Appl. No. 14/766,849, May 3, 2018.
U.S. Appl. No. 14/766,849, Oct. 2, 2017.
U.S. Appl. No. 14/766,849, Jun. 1, 2017.
U.S. Appl. No. 14/766,849, Sep. 19, 2016.

* cited by examiner pH 9.0 refold pH 10.4 refold

G25 refold
30 minute incubation
No glutathione/TCEP

G25 refold
4 hour incubation
No glutathione/TCEP

← dimer

← monomer

SEQUENCE LISTING

<160> NUMBER OF SEQ ID NOS: 109

<210> SEQ ID NO 1
<211> LENGTH: 101
<212> TYPE: PRT
<213> ORGANISM: Homo sapiens

<400> SEQUENCE: 1

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser Gln
```

-continued

100

<210> SEQ ID NO 2
<211> LENGTH: 101
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Glu Lys Pro Ser Gln
            100

<210> SEQ ID NO 3
<211> LENGTH: 85
<212> TYPE: PRT
<213> ORGANISM: Homo sapiens

<400> SEQUENCE: 3

Leu Glu Val Val Ala Ala Thr Pro Thr Ser Leu Leu Ile Ser Trp Asp
1               5                   10                  15

Ala Pro Ala Val Thr Val Arg Tyr Tyr Arg Ile Thr Tyr Gly Glu Thr
            20                  25                  30

Gly Gly Asn Ser Pro Val Gln Glu Phe Thr Val Pro Gly Ser Lys Ser
        35                  40                  45

Thr Ala Thr Ile Ser Gly Leu Lys Pro Gly Val Asp Tyr Thr Ile Thr
50                  55                  60

Val Tyr Ala Val Thr Gly Arg Gly Asp Ser Pro Ala Ser Ser Lys Pro
65                  70                  75                  80

Ile Ser Ile Asn Tyr
                85

<210> SEQ ID NO 4
<211> LENGTH: 86
<212> TYPE: PRT
<213> ORGANISM: Homo sapiens

<400> SEQUENCE: 4

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Glu Thr Gly
            20                  25                  30

Gly Asn Ser Pro Val Gln Glu Phe Thr Val Pro Gly Ser Lys Ser Thr
        35                  40                  45

Ala Thr Ile Ser Gly Leu Lys Pro Gly Val Asp Tyr Thr Ile Thr Val

```
                    50                  55                  60
Tyr Ala Val Thr Gly Arg Gly Asp Ser Pro Ala Ser Ser Lys Pro Ile
 65                  70                  75                  80

Ser Ile Asn Tyr Arg Thr
                    85

<210> SEQ ID NO 5
<211> LENGTH: 94
<212> TYPE: PRT
<213> ORGANISM: Homo sapiens

<400> SEQUENCE: 5

Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
         50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr
                 85                  90

<210> SEQ ID NO 6
<211> LENGTH: 95
<212> TYPE: PRT
<213> ORGANISM: Homo sapiens

<400> SEQUENCE: 6

Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
         50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr Glu
                 85                  90                  95

<210> SEQ ID NO 7
<211> LENGTH: 96
<212> TYPE: PRT
<213> ORGANISM: Homo sapiens

<400> SEQUENCE: 7

Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
         50                  55                  60
```

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

<210> SEQ ID NO 8
<211> LENGTH: 97
<212> TYPE: PRT
<213> ORGANISM: Homo sapiens

<400> SEQUENCE: 8

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp

<210> SEQ ID NO 9
<211> LENGTH: 97
<212> TYPE: PRT
<213> ORGANISM: Homo sapiens

<400> SEQUENCE: 9

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Glu

<210> SEQ ID NO 10
<211> LENGTH: 98
<212> TYPE: PRT
<213> ORGANISM: Homo sapiens

<400> SEQUENCE: 10

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
                50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr Glu Ile
                 85                  90                  95

Asp Lys

<210> SEQ ID NO 11
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Gly Ser Lys Ser Thr Ala Thr Ile Ser Gly Leu Lys Pro
                50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr Glu Ile
                 85                  90                  95

Glu Lys

<210> SEQ ID NO 12
<211> LENGTH: 99
<212> TYPE: PRT
<213> ORGANISM: Homo sapiens

<400> SEQUENCE: 12

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Gly Ser Lys Ser Thr Ala Thr Ile Ser Gly Leu Lys Pro
                50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr Glu Ile
                 85                  90                  95

Asp Lys Pro

<210> SEQ ID NO 13
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 13

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Glu Lys Pro

<210> SEQ ID NO 14
<211> LENGTH: 100
<212> TYPE: PRT
<213> ORGANISM: Homo sapiens

<400> SEQUENCE: 14

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser
            100

<210> SEQ ID NO 15
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 15

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp

```
                65                  70                  75                  80
Ser Pro Ala Ser Ser Lys Pro Ile Ser Ile Asn Tyr Arg Thr Glu Ile
                    85                  90                  95

Glu Lys Pro Ser
            100

<210> SEQ ID NO 16
<211> LENGTH: 101
<212> TYPE: PRT
<213> ORGANISM: Homo sapiens

<400> SEQUENCE: 16

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Thr Glu Ile
                    85                  90                  95

Asp Lys Pro Ser Gln
            100

<210> SEQ ID NO 17
<211> LENGTH: 166
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(126)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (133)..(152)
<223> OTHER INFORMATION: Any amino acid and this region may encompass
      2-20, 2-15, 2-10, 2-8, 5-20, 5-15, 5-10, 5-8, 6-20, 6-15, 6-10,
```

6-8, 2-7, 5-7, or 6-7 residues, wherein some positions may be
    absent
<220> FEATURE:
<221> NAME/KEY: MOD_RES
<222> LOCATION: (160)..(179)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: misc_feature
<222> LOCATION: (1)..(186)
<223> OTHER INFORMATION: /note="see specification as filed for detailed
    description of substitutions and preferred embodiments"

<400> SEQUENCE: 17

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Ala Thr Ile Ser Gly Leu
        100                 105                 110

Xaa Xaa Xaa Xaa Xaa Xaa Xaa Xaa Xaa Xaa Xaa Xaa Xaa Xaa Xaa Xaa
    115                 120                 125

Xaa Xaa Xaa Xaa Tyr Thr Ile Thr Val Tyr Ala Xaa Xaa Xaa Xaa Xaa
130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr
                165

<210> SEQ ID NO 18
<211> LENGTH: 167
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: MOD_RES
<222> LOCATION: (14)..(33)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (39)..(58)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (64)..(83)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be

```
       absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 18

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
            35                  40                  45

Xaa Xaa Xaa Xaa Xaa Xaa Xaa Xaa Xaa Tyr Arg Ile Thr Tyr Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
            130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu
                165

<210> SEQ ID NO 19
<211> LENGTH: 168
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
```

6-8, 2-7, 5-7, or 6-7 residues, wherein some positions may be
    absent
<220> FEATURE:
<221> NAME/KEY: MOD_RES
<222> LOCATION: (64)..(83)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (87)..(106)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (113)..(132)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (140)..(159)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent

<400> SEQUENCE: 19

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
        35                  40                  45

Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile
                165

<210> SEQ ID NO 20
<211> LENGTH: 169
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: MOD_RES
<222> LOCATION: (14)..(33)
<223> OTHER INFORMATION: Any amino acid and this region may encompass 2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (39)..(58)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (64)..(83)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (87)..(106)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (113)..(132)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (140)..(159)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent

<400> SEQUENCE: 20

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
            35                  40                  45

Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
        130                 135                 140

Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp
                165

<210> SEQ ID NO 21
<211> LENGTH: 169
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 21

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Xaa Xaa Ile
145                 150                 155                 160
```

Ser Ile Asn Tyr Arg Thr Glu Ile Glu
                165

<210> SEQ ID NO 22
<211> LENGTH: 170
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 22

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Tyr Arg Ile Thr Tyr Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa Xaa 130                 135                 140
Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp Lys
                165                 170

<210> SEQ ID NO 23
<211> LENGTH: 170
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 23

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
            35                  40                  45

Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
            85                  90                  95

Xaa Xaa Xaa Xaa Xaa Xaa Xaa Xaa Xaa Xaa Ala Thr Ile Ser Gly Leu
                100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys
                165                 170

<210> SEQ ID NO 24
<211> LENGTH: 171
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 24

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

```
Xaa Xaa Xaa Xaa Xaa Xaa Xaa Xaa Xaa Tyr Arg Ile Thr Tyr Xaa
        50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Phe Thr Val Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
                115                 120                 125

Xaa Xaa Xaa Xaa Tyr Thr Ile Thr Val Tyr Ala Xaa Xaa Xaa Xaa
        130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp Lys Pro
                165                 170

<210> SEQ ID NO 25
<211> LENGTH: 171
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 25

Val Ser Asp Val Pro Arg Asp Leu Glu Val Val Ala Ala Xaa Xaa Xaa
```

```
1               5                   10                  15
Xaa Xaa Xaa Xaa Xaa Xaa Xaa Xaa Xaa Xaa Xaa Xaa Xaa Xaa Xaa
            20                  25                  30
Xaa Leu Leu Ile Ser Trp Xaa Xaa Xaa Xaa Xaa Xaa Xaa Xaa Xaa
            35                  40                  45
Xaa Xaa Xaa Xaa Xaa Xaa Xaa Xaa Xaa Tyr Arg Ile Thr Tyr Xaa
            50                  55                  60
Xaa Xaa Xaa Xaa Xaa Xaa Xaa Xaa Xaa Xaa Xaa Xaa Xaa Xaa Xaa
65                  70                  75                  80
Xaa Xaa Xaa Phe Thr Val Xaa Xaa Xaa Xaa Xaa Xaa Xaa Xaa Xaa
            85                  90                  95
Xaa Xaa Xaa Xaa Xaa Xaa Xaa Xaa Xaa Ala Thr Ile Ser Gly Leu
            100                 105                 110
Xaa Xaa Xaa Xaa Xaa Xaa Xaa Xaa Xaa Xaa Xaa Xaa Xaa Xaa Xaa
            115                 120                 125
Xaa Xaa Xaa Xaa Tyr Thr Ile Thr Val Tyr Ala Xaa Xaa Xaa Xaa
            130                 135                 140
Xaa Xaa Xaa Xaa Xaa Xaa Xaa Xaa Xaa Xaa Xaa Xaa Xaa Xaa Ile
145                 150                 155                 160
Ser Ile Asn Tyr Arg Thr Glu Ile Glu Lys Pro
                165                 170

<210> SEQ ID NO 26
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
```

```
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent

<400> SEQUENCE: 26

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
            35                  40                  45

Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
            85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa Xaa
130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp Lys Pro Ser
                165                 170

<210> SEQ ID NO 27
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
```

<222> LOCATION: (113)..(132)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (140)..(159)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent

<400> SEQUENCE: 27

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
            35                  40                  45

Xaa Xaa Xaa Xaa Xaa Xaa Xaa Xaa Xaa Tyr Arg Ile Thr Tyr Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa Xaa
    130                 135                 140

Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys Pro Ser
                165                 170

<210> SEQ ID NO 28
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"
<220> FEATURE:
<221> NAME/KEY: MOD_RES
<222> LOCATION: (14)..(33)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (39)..(58)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (64)..(83)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:

-continued

```
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 28

Val Ser Asp Val Pro Arg Asp Leu Glu Val Val Ala Ala Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa Leu Leu Ile Ser Trp Xaa Xaa Xaa Xaa Xaa Xaa Xaa Xaa Xaa Xaa
             35                  40                  45

Xaa Xaa Xaa Xaa Xaa Xaa Xaa Xaa Xaa Tyr Arg Ile Thr Tyr Xaa
         50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Phe Thr Val Xaa Xaa Xaa Xaa Xaa Xaa Xaa Xaa Xaa
             85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa
        130                 135                 140

Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Asp Lys Pro Ser Gln
                165                 170

<210> SEQ ID NO 29
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
```

```
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 29

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr Glu Ile Glu Lys Pro Ser Gln
                165                 170

<210> SEQ ID NO 30
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Met Gly Val Ser Asp Val Pro Arg Asp Leu
1               5                   10
```

```
<210> SEQ ID NO 31
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gly Val Ser Asp Val Pro Arg Asp Leu
1               5

<210> SEQ ID NO 32
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be
      absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 32

Met Gly Ser Asp Val Pro Arg Asp Leu
1               5

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be
      absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
```

<223> OTHER INFORMATION: /note="see specification as filed for detailed
      description of substitutions and preferred embodiments"

<400> SEQUENCE: 33

Met Gly Asp Val Pro Arg Asp Leu
1               5

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be
      absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 34

Met Gly Val Pro Arg Asp Leu
1               5

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: This region may encompass 0-2 residues selected
      from Met, Gly or "Met Gly," wherein some positions may be
      absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 35

Met Gly Pro Arg Asp Leu
1               5

<210> SEQ ID NO 36
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (1)..(2)
<223> OTHER INFORMATION: This region may encompass 0-2 residues selected from Met, Gly or "Met Gly," wherein some positions may be absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence have no preference with respect to those in the annotations for variant positions"
<220> FEATURE:
<221> NAME/KEY: misc_feature
<222> LOCATION: (1)..(8)
<223> OTHER INFORMATION: /note="see specification as filed for detailed description of substitutions and preferred embodiments"

<400> SEQUENCE: 36

Met Gly Arg Asp Leu
1               5

<210> SEQ ID NO 37
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (1)..(2)
<223> OTHER INFORMATION: This region may encompass 0-2 residues selected from Met, Gly or "Met Gly," wherein some positions may be absent
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(8)
<223> OTHER INFORMATION: /note="Variant residues given in the sequence have no preference with respect to those in the annotations for variant positions"
<220> FEATURE:
<221> NAME/KEY: misc_feature
<222> LOCATION: (1)..(8)
<223> OTHER INFORMATION: /note="see specification as filed for detailed description of substitutions and preferred embodiments"

<400> SEQUENCE: 37

Met Gly Asp Leu
1

<210> SEQ ID NO 38
<211> LENGTH: 6
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 38

Met Ala Ser Thr Ser Gly
1               5

<210> SEQ ID NO 39
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Glu Ile Glu Lys
1

<210> SEQ ID NO 40
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Glu Gly Ser Gly Cys
1               5

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Glu Ile Glu Lys Pro Cys Gln
1               5

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Glu Ile Glu Lys Pro Ser Gln
1               5

<210> SEQ ID NO 43
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 43

Glu Ile Glu Lys Pro
1               5

<210> SEQ ID NO 44
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Glu Ile Glu Lys Pro Ser
1               5

<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Glu Ile Glu Lys Pro Cys
1               5

<210> SEQ ID NO 46
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 46

His His His His His His
1               5

<210> SEQ ID NO 47
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Glu Ile Asp Lys
1

<210> SEQ ID NO 48
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Glu Ile Asp Lys Pro Cys Gln
1               5
```

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Glu Ile Asp Lys Pro Ser Gln
1               5

<210> SEQ ID NO 50
<211> LENGTH: 91
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Met Pro Ala Pro Thr Asp Leu Arg Phe Thr Asn Glu Thr Pro Ser Ser
1               5                   10                  15

Leu Leu Ile Ser Trp Thr Pro Pro Arg Val Gln Ile Thr Gly Tyr Ile
            20                  25                  30

Ile Arg Tyr Gly Pro Val Gly Ser Asp Gly Arg Val Lys Glu Phe Thr
        35                  40                  45

Val Pro Pro Ser Val Ser Ser Ala Thr Ile Thr Gly Leu Lys Pro Gly
    50                  55                  60

Thr Glu Tyr Thr Ile Ser Val Ile Ala Leu Lys Asp Asn Gln Glu Ser
65                  70                  75                  80

Glu Pro Leu Arg Gly Arg Val Thr Thr Gly Gly
                85                  90

<210> SEQ ID NO 51
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Thr Pro Ser Ser
1

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Thr Pro Pro Arg Val Gln Ile
1               5

<210> SEQ ID NO 53
<211> LENGTH: 6

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Val Gly Ser Asp Gly Arg
1               5

<210> SEQ ID NO 54
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Pro Ser Val Ser
1

<210> SEQ ID NO 55
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gly Leu Lys Pro Gly
1               5

<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Lys Asp Asn Gln Glu Ser Glu Pro
1               5

<210> SEQ ID NO 57
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
                20                  25                  30

Ile Thr Tyr Thr Pro Ser Asn Gly Pro Gly Glu Pro Lys Glu Leu Thr
            35                  40                  45

Val Pro Pro Ser Ser Thr Ser Val Thr Ile Thr Gly Ile Thr Pro Gly
```

Val Glu Tyr Val Val Ser Val Tyr Ala Leu Lys Asp Asn Gln Glu Ser
65                  70                  75                  80

Pro Pro Leu Val Gly Thr Cys Thr Thr
                85

<210> SEQ ID NO 58
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85

<210> SEQ ID NO 59
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Thr Glu Asp Ser
1

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Thr Ala Pro Asp Ala Ala Phe
1               5

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

```
Ser Glu Lys Val Gly Glu
1               5

<210> SEQ ID NO 62
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Ser Glu Arg
1

<210> SEQ ID NO 63
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Leu Lys Pro Gly
1               5

<210> SEQ ID NO 64
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Lys Gly Gly His Arg Ser Asn
1               5

<210> SEQ ID NO 65
<211> LENGTH: 330
<212> TYPE: PRT
<213> ORGANISM: Homo sapiens

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 66
<211> LENGTH: 227
<212> TYPE: PRT
<213> ORGANISM: Homo sapiens

<400> SEQUENCE: 66

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160
```

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 67
<211> LENGTH: 208
<212> TYPE: PRT
<213> ORGANISM: Homo sapiens

<400> SEQUENCE: 67

Val Phe Leu Phe Pro Pro Lys Pro Lys Asp Thr Leu Met Ile Ser Arg
1               5                   10                  15

Thr Pro Glu Val Thr Cys Val Val Asp Val Ser His Glu Asp Pro
            20                  25                  30

Glu Val Lys Phe Asn Trp Tyr Val Asp Gly Val Glu Val His Asn Ala
        35                  40                  45

Lys Thr Lys Pro Arg Glu Glu Gln Tyr Asn Ser Thr Tyr Arg Val Val
    50                  55                  60

Ser Val Leu Thr Val Leu His Gln Asp Trp Leu Asn Gly Lys Glu Tyr
65                  70                  75                  80

Lys Cys Lys Val Ser Asn Lys Ala Leu Pro Ala Pro Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Arg Asp Glu Leu Thr Lys Asn Gln Val Ser Leu Thr Cys
        115                 120                 125

Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
            180                 185                 190

Leu His Asn His Tyr Thr Gln Lys Ser Leu Ser Leu Ser Pro Gly Lys
        195                 200                 205

<210> SEQ ID NO 68
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Glu Pro Arg Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

```
Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 69
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140
```

-continued

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 70
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 71
<211> LENGTH: 232
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Gln Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 72
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Glu Pro Arg Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

Tyr Asn Ser Thr Tyr Arg Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 73
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

```
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225
```

<210> SEQ ID NO 74
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 74

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 75
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 75

```
Glu Pro Lys Ser Ser Asp Lys Thr His Thr Cys Pro Pro Cys Pro Ala
```

```
1               5                   10                  15
Pro Glu Ala Glu Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 76
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ser Ser Ile Glu Lys Thr Ile Ser Lys Ala Lys Gly Gln Pro
            115                 120                 125
```

```
Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 77
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Gly
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

-continued

```
<210> SEQ ID NO 78
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Gly
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 79
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Lys Phe Asn Trp Tyr Val Asp Gly Val
```

```
            50                  55                  60
Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 80
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Glu Pro Lys Ser Ser Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Gln Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Arg Leu Thr Val Asp Lys Ser Arg Trp Gln Glu Gly Asn Val Phe
            195                 200                 205

Ser Cys Ser Val Met His Glu Ala Leu His Asn His Tyr Thr Gln Lys
        210                 215                 220

Ser Leu Ser Leu Ser Leu Gly Lys
225                 230

<210> SEQ ID NO 81
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Ala Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 82
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 82

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Ala Tyr Thr Gln Lys
210                 215                 220

Ser Leu Ser Leu Ser Pro Gly Lys
225                 230
```

<210> SEQ ID NO 83
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

```
Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Gln Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
```

```
            100                 105                 110
Leu Pro Ser Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 84
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Ala Leu Gly
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

Ser Leu Ser Leu Ser Pro Gly Lys
225                 230

<210> SEQ ID NO 85
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Ala Leu Gly
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 86
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Glu Pro Lys Ser Ser Asp Lys Thr His Thr Cys Pro Pro Cys Pro Ala
1               5                   10                  15

Pro Glu Ala Gly Gly Gly Pro Ser Val Phe Leu Phe Pro Pro Lys Pro
            20                  25                  30

```
Lys Asp Thr Leu Met Ile Ser Arg Thr Pro Glu Val Thr Cys Val Val
                 35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Ser Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
                210                 215                 220

Ser Leu Ser Leu Ser Pro Gly Lys
225                 230

<210> SEQ ID NO 87
<211> LENGTH: 16
<212> TYPE: PRT
<213> ORGANISM: Homo sapiens

<400> SEQUENCE: 87

Asp Lys Thr His Thr Cys Pro Pro Cys Pro Ala Pro Glu Leu Leu Gly
1               5                   10                  15

<210> SEQ ID NO 88
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Glu Pro Lys Ser Ser Asp Lys Thr His Thr Cys Pro Pro Cys Pro Ala
1               5                   10                  15

Pro Glu Leu Leu Gly Gly Pro Ser
            20

<210> SEQ ID NO 89
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89
```

Glu Pro Lys Ser Ser Asp Lys Thr His Thr Cys Pro Pro Cys Pro Ala
1               5                   10                  15

Pro Glu Leu Leu Gly Gly Ser Ser
            20

<210> SEQ ID NO 90
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Glu Pro Lys Ser Ser Gly Ser Thr His Thr Cys Pro Pro Cys Pro Ala
1               5                   10                  15

Pro Glu Leu Leu Gly Gly Ser Ser
            20

<210> SEQ ID NO 91
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Asp Lys Thr His Thr Cys Pro Pro Cys Pro Ala Pro Glu Leu Leu Gly
1               5                   10                  15

Gly Pro Ser

<210> SEQ ID NO 92
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Asp Lys Thr His Thr Cys Pro Pro Cys Pro Ala Pro Glu Leu Leu Gly
1               5                   10                  15

Gly Ser Ser

<210> SEQ ID NO 93
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Glu Pro Lys Ser Ser Asp Lys Thr His Thr Cys Pro Pro Cys Pro
1               5                   10                  15

<210> SEQ ID NO 94
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 94

```
Met Gly Val Ser Asp Val Pro Arg Asp Leu Glu Val Val Ala Ala Thr
1               5                   10                  15

Pro Thr Ser Leu Leu Ile Ser Trp Val Pro Ser Asp Asp Tyr Gly
            20                  25                  30

Tyr Tyr Arg Ile Thr Tyr Gly Glu Thr Gly Gly Asn Ser Pro Val Gln
            35                  40                  45

Glu Phe Thr Val Pro Ile Gly Lys Gly Thr Ala Thr Ile Ser Gly Leu
50                  55                  60

Lys Pro Gly Val Asp Tyr Thr Ile Thr Val Tyr Ala Val Glu Phe Pro
65                  70                  75                  80

Trp Pro His Ala Gly Tyr Tyr His Arg Pro Ile Ser Ile Asn Tyr Arg
                85                  90                  95

Thr Glu Ile Glu Pro Lys Ser Ser Gly Ser Thr His Thr Cys Pro Pro
            100                 105                 110

Cys Pro Ala Pro Glu Leu Leu Gly Gly Ser Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
            245                 250                 255

Tyr Pro Ser Asp Ile Ala Val Glu Trp Glu Ser Asn Gly Gln Pro Glu
        260                 265                 270

Asn Asn Tyr Lys Thr Thr Pro Pro Val Leu Asp Ser Asp Gly Ser Phe
    275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330
```

<210> SEQ ID NO 95
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 95

Met Gly Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
210                 215                 220

Leu Ser Pro
225

<210> SEQ ID NO 96
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Ser Gly Ser
1

<210> SEQ ID NO 97
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Ser Gly Ser Gly Ser
1               5

<210> SEQ ID NO 98
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Ser Gly Ser Gly Ser Gly Ser
1               5

<210> SEQ ID NO 99
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gly Ser Gly Ser Gly Ser Gly Ser Gly Ser
1               5                   10

<210> SEQ ID NO 100
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Ser Gly Ser Gly Ser Gly Ser Gly Ser Gly Ser
1               5                   10

<210> SEQ ID NO 101
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gly Ser Gly Ser Gly Ser Gly Ser Gly Ser Gly Ser Gly Ser
1               5                   10

<210> SEQ ID NO 102
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Gly Ser Gly Ser Gly Ser Gly Ser Gly Ser Gly Ser Gly Ser Gly Ser
1               5                   10                  15

<210> SEQ ID NO 103
<211> LENGTH: 18
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 103

Gly Ser Gly Ser Gly Ser Gly Ser Gly Ser Gly Ser Gly Ser Gly Ser
1               5                   10                  15

Gly Ser

<210> SEQ ID NO 104
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Gly Ser Gly Ser Gly Ser Gly Ser Gly Ser Gly Ser Gly Ser Gly Ser
1               5                   10                  15

Gly Ser Gly Ser
            20

<210> SEQ ID NO 105
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Gly Gly Gly Gly Ser
1               5

<210> SEQ ID NO 106
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Gly Gly Gly Gly Ser Gly Gly Gly Gly Ser
1               5                   10

<210> SEQ ID NO 107
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gly Gly Gly Gly Ser Gly Gly Gly Gly Ser Gly Gly Gly Gly Ser
1               5                   10                  15

<210> SEQ ID NO 108
<211> LENGTH: 20
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Gly Gly Gly Gly Ser Gly Gly Gly Gly Ser Gly Gly Gly Gly Ser Gly
1               5                   10                  15

Gly Gly Gly Ser
            20

<210> SEQ ID NO 109
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

HIGH PH PROTEIN REFOLDING METHODS

CROSS-REFERENCE TO RELATED APPLICATIONS

This patent application is a continuation of U.S. patent application Ser. No. 14/766,848, filed Aug. 10, 2015 (now U.S. Pat. No. 10,065,987), which is a 35 U.S.C. 371 national stage filing of International Application No. PCT/US2014/015702, filed Feb. 11, 2014, which claims the benefit of U.S. Provisional Patent Application No. 61/763,664, filed Feb. 12, 2013. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Jul. 31, 2018, is named MXI_567USCN_Sequence_Listing.txt and is 128,109 bytes in size.

BACKGROUND

The backbone of an antibody, known as the Fc region, is responsible for pharmacokinetic properties that may be desirable in the case of many therapeutic biologics (Jeffries, B. Biotechnol Prog. 2005; 21: 11-16). The size of the Fc region makes it resistant to renal filtration and binding to the Fc Neonatal Receptor (FcRn) allows it to escape endosomal degradation by a recycling mechanism. In addition to the Fc region that is present in monoclonal antibody therapeutic products, there are Fc fusion products being investigated and developed (Hakim et al. Mabs. 2009; 1:281-287). Fc fusions are the fusion of an Fc region to another protein, peptide, or Active Pharmaceutical Ingredient (API). The Fc fusion then has both the properties of the Fc region and the therapeutic properties of the API.

There are many cell lines that are capable of being used to manufacture therapeutic biologics (Jung et al. Curr Opin Biotechnol. 2011; 22:1-10). The mammalian Chinese Hamster Ovary (CHO), insect Sf9, yeast S. cereviae, and bacterial E. coli are some of the most common cell lines that are discussed for recombinant protein production. So far, yeast, CHO and E. coli have been used for manufacture of Fc containing therapeutic biologics, including a large number of monoclonal antibodies. Expression in E. coli offers three potential and significant advantages over expression in other cell lines: the cell line development time is much shorter; the bioreactor runs are up to 7-fold shorter, resulting in a lower capital investment; and there is no need to control aberrant glycosylation that can occur in yeast and mammalian cell cultures.

Expression of larger proteins, like Fc fusions, in E. coli can be a unique challenge. E. coli lack the chaperone proteins and other refolding machinery found in a eukaryotic expression system. The cytoplasm of E. coli is also a reducing environment, which is not favorable for the formation of disulfide bonds. The Fc region of human IgG1 antibodies contains six disulfide bonds. Two disulfide bonds the hinge region join two peptide chains to form the homodimeric molecule and there are two more disulfide bonds within each of the peptide chains. E. coli also have a mechanism to prevent unfolded proteins from interfering with normal cell processes. Unfolded protein is shunted and isolated in insoluble aggregates, called Inclusion Bodies (IB), which can then be isolated in the insoluble fraction following cell lysis. Alternatively, when the rate of recombinant protein production is slowed to allow the protein to fold, a leader sequence may be added to direct soluble protein that is expressed to the periplasmic space. The periplasm is an oxidative environment favorable for the formation of disulfide bonds. However, the reported expression levels of recombinant protein in the periplasm remain low (Liu et al. Protein Expression Purif. 2008; 62:15-20).

In contrast, E. coli expression levels in IBs have been reported to be high. Expressing protein in IBs also has the advantages of resistance to protein degradation, and ease of isolation from the cells (Grune et al. Int J Biochem Cell Biol. 2004; 36:2519-2530). Since an IB is an insoluble aggregate, there may be a challenge in restoring the protein of interest to its biologically active conformation (Jungbauer et al. J Biotechnol. 2006; 587-596). Typically, a process is required to break apart and solubilize the IB. Then the protein must be renatured, or refolded, into the biologically active conformation while minimizing losses due to aggregation and precipitation. Current refolding processes may be specific to a given protein, requiring thorough optimization for each case. Many refolding processes require very low protein concentrations and consequently large volumes for the operation. This is difficult because it requires a larger amount of potentially expensive reagents. There is also a challenge in a manufacturing setting, where there is a physical limit to the container size that may be used to refold proteins. Finally, in the case of Fc fusions, the refolding process must correctly form the six disulfide bonds that exist in the native form of the protein.

SUMMARY

Provided herein are methods for refolding a denatured protein, comprising, e.g., (i) suspending a denatured protein in a suspension solution to obtain a composition comprising suspended denatured proteins; (ii) combining the composition comprising suspended denatured proteins with a solubilization buffer having a pH in the range of 10.5 to 13 to thereby obtain a composition comprising solubilized denatured proteins; and (iii) combining the composition comprising solubilized denatured proteins with a refold buffer having a pH in the range of 9 to 11 to thereby obtain a composition comprising refolded proteins. In certain methods, the method does not include the use of a significant amount of denaturing agent and/or reducing agent. The pH of the solubilization buffer may be in the range of pH 11.5 to 12.8, such as in the range of pH 12.0 to 12.6. The pH of the refold buffer may be in the range of pH 10 to 10.6, such as in the range of pH 10.3 to 10.5. The suspension solution may consist of water. The composition comprising solubilized denatured protein may have a pH in the range of 11 to 13, such as a pH in the range of pH 11.5 to 12.8, e.g., pH 12.0 to 12.6. The composition comprising refolded protein may have a pH in the range of 10 to 11, such as in the range of 10 to 10.6, e.g., pH 10.3 to 10.5.

The denatured proteins may be suspended in suspension solution at a ratio of weight (g) of denatured proteins: volume (ml) of suspension solution of 1:1-3, e.g., about 1:2. The suspension solution may be water. The composition comprising suspended denatured proteins may be combined with solubilization buffer at a ratio of weight (g; e.g., weight prior to adding suspension solution) of denatured proteins or volume of suspension solution (ml):volume (ml) of solubilization buffer of 1:10-30, such as about 1:20. The composition comprising solubilized denatured proteins may be combined with refold buffer at a ratio of volume of solubilization buffer:volume of refold buffer of 1:1-5, such as about 1:3-4.

In the methods described herein, the denatured proteins may be suspended in suspension solution at a ratio of weight (g) of denatured proteins:volume (ml) of suspension solution of 1:1-3; the composition comprising suspended denatured proteins may be combined with solubilization buffer at a ratio of weight (g) of denatured proteins:volume (ml) of solubilization buffer of 1:10-30; and the composition comprising solubilized denatured proteins may be combined with refold buffer at a ratio of volume of solubilization buffer:volume of refold buffer of 1:1-5. The solubilization buffer may have a pH in the range of 11.5 to 12.8 and the refold buffer may have a pH in the range of 10 to 10.9. The denatured proteins may be suspended in suspension solution at a ratio of weight (g) of denatured proteins:volume (ml) of suspension solution of about 1:2; the composition comprising suspended denatured proteins may be combined with solubilization buffer at a ratio of weight (g) of denatured proteins:volume (ml) of solubilization buffer of about 1:20; and the composition comprising solubilized denatured proteins may be combined with refold buffer at a ratio of volume of solubilization buffer:volume of refold buffer of about 1:3-4. The denatured proteins may be suspended in water at a ratio of weight (g) of denatured proteins:volume (ml) of suspension solution of about 1:2; the composition comprising suspended denatured proteins may be combined with solubilization buffer having a pH of about 12.2 at a ratio of weight (g) of denatured proteins:volume (ml) of solubilization buffer of about 1:20; and the composition comprising solubilized denatured proteins may be combined with refold buffer having a pH in the range of 10.2 to 10.6 at a ratio of volume of solubilization buffer:volume of refold buffer of about 1:3-4.

In the methods described herein, the suspended denatured proteins and the solubilization buffer may be combined for 1-10, e.g., 2-5, minutes prior to being combined with the refold buffer. The composition comprising the solubilized denatured proteins may be combined with the refold buffer for 5-60, e.g., 15-25, minutes.

In the methods described herein, the pH of the solution comprising the refolded proteins may be reduced following refolding.

In the methods described herein, the solubilization buffer and/or the refold buffer may comprise Arginine. The refold buffer may comprise an oxidizing agent, e.g., glutathione, wherein, e.g., glutathione is at an about 5:1 oxidized:reduced ratio.

In certain embodiments, the method does not comprise first suspending the denatured protein in a suspension solution. In certain embodiments, the method does not include the use of a denaturing agent. The denatured proteins may be in the form of inclusion bodies (IBs). The protein that is renatured according to the methods described herein may comprise at least one cysteine. The protein may comprise at least two cysteines that form a disulfide bond in the native protein. The protein may comprise an Fc region, which may comprise a hinge. The protein may comprise a binding domain that specifically binds to a target protein. The binding domain may be an alternative scaffold binding domain, such as a fibronectin based scaffold domain, e.g., a $^{10}$FN3 domain. In certain embodiments, the protein comprises a $^{10}$FN3 protein and an Fc region comprising a hinge, a CH2 and a CH3 domain.

Also provided herein are compositions, e.g., compositions comprising a protein comprising at least two cysteines that form a disulfide bond under appropriate conditions, and water, wherein the composition does not comprise a buffer or a denaturing agent. Also provided are compositions comprising a suspension of denatured proteins, wherein at least some proteins comprise at least two cysteines that form a disulfide bond under appropriate conditions, and wherein the composition does not comprise a buffer or a denaturing agent. Also provided are compositions comprising a protein comprising at least two cysteines that form a disulfide bond under appropriate conditions, and a solubilization buffer having a pH in the range of pH 10 to 13, wherein the composition does not comprise a denaturing agent. Further provided are compositions comprising a protein comprising at least two cysteines that form a disulfide bond under appropriate conditions, and a refold buffer having a pH in the range of pH 9 to 11 and an oxidizing agent, wherein the composition does not comprise a reducing agent other than a reducing agent that part of an oxidizing agent that is present in the composition. The protein may comprise an Fc region or a portion thereof. The protein may comprise a binding domain, e.g., an FBS domain, e.g., a $^{10}$Fn3 domain. The $^{10}$Fn3 domain may bind specifically to a target, and the $^{10}$Fn3 domain may comprise an amino acid sequence that is at least 50% identical to any of SEQ ID NOs: 1-29. The protein may be present in the composition at a concentration of at least 5 mg/ml or 10 mg/ml.

BRIEF DESCRIPTION OF THE FIGURES

FIG. 2A) G25 refold performed with 50 mM Tris pH 8.5 and 0.4 M Arginine. FIG. 2B) G25 refold performed with 50 mM Tris pH 9.0 and 0.4 M Arginine. FIG. 2C) G25 refold performed with 50 mM Tris pH 10.4 and 0.4 M Arginine.

FIG. 6A shows Near UV CD representing tertiary structure of the protein at varying pHs or in the presence of guanidine. FIG. 6B shows Far UV CD representing secondary structure of the protein at varying pHs and in the presence of guanidine.

DETAILED DESCRIPTION

Figure 1:
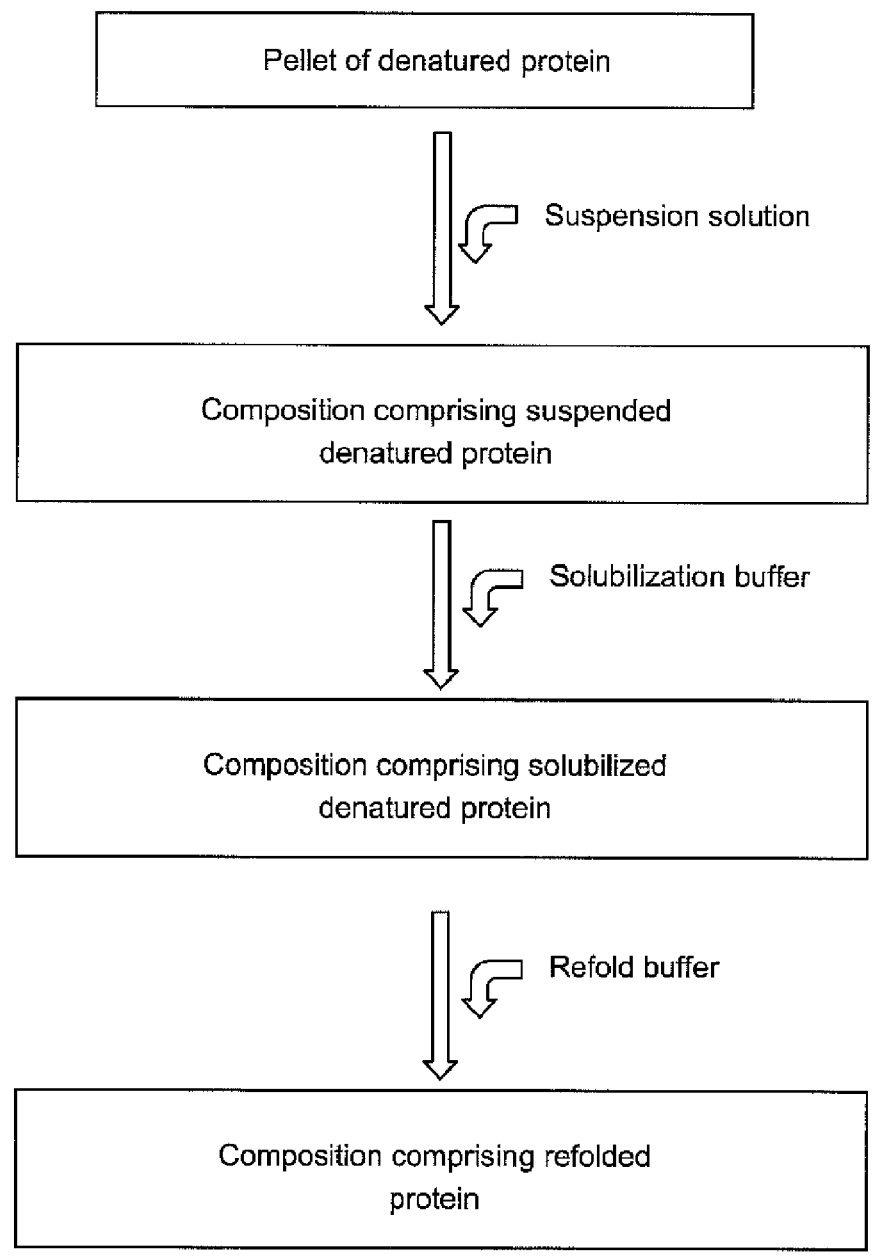
FIG. 1 shows a diagram showing exemplary steps for refolding a denatured protein.

Provided herein are methods for refolding denatured proteins, such as proteins present in the form of inclusion bodies (IBs). The methods are applicable to, e.g., proteins comprising at least one disulfide bond, such as proteins comprising an Fc region or domain (or portions thereof) of antibodies. A method may comprise combining a composition comprising denatured or unfolded proteins with a composition having a strongly alkaline pH, followed by incubation at reduced pH. Unlike commonly used methods for refolding proteins, e.g., from IBs, the methods described herein do not require the use of a denaturing or chaotropic agent. In addition, the methods described herein allow refolding of denatured proteins, e.g., from IBs, without the use of large volumes of buffer and in generally shorter time frames than those of current commonly used methods.

Definitions

By "polypeptide" is meant any sequence of two or more amino acids, regardless of length, post-translation modification, or function. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

A "region" of a $^{10}$Fn3 domain (or moiety) as used herein refers to either a loop (AB, BC, CD, DE, EF and FG), a β-strand (A, B, C, D, E, F and G), the N-terminus (corresponding to amino acid residues 1-7 of SEQ ID NO: 1), or the C-terminus (corresponding to amino acid residues 93-101 of SEQ ID NO: 1) of the human $^{10}$Fn3 domain having SEQ ID NO: 1.

A "north pole loop" refers to any one of the BC, DE and FG loops of a human fibronectin type 3 tenth ($^{10}$Fn3) domain.

A "south pole loop" refers to any one of the AB, CD and EF loops of a human fibronectin type 3 tenth ($^{10}$Fn3) domain.

A "scaffold region" refers to any non-loop region of a human $^{10}$Fn3 domain. The scaffold region includes the A, B, C, D, E, F and G β-strands as well as the N-terminal region (amino acids corresponding to residues 1-7 of SEQ ID NO: 1) and the C-terminal region (amino acids corresponding to residues 93-101 of SEQ ID NO: 1).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc., has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

As used herein, an amino acid residue in a polypeptide is considered to "contribute to binding" a target if (1) any of the non-hydrogen atoms of the residue's side chain or main chain is found to be within five angstroms of any atom of the binding target based on an experimentally determined three-dimensional structure of the complex, and/or (2) mutation of the residue to its equivalent in wild-type $^{10}$Fn3 (e.g., SEQ ID NO: 1), to alanine, or to a residue having a similarly sized or smaller side chain than the residue in question, leads to a measured increase of the equilibrium dissociation constant to the target (e.g., an increase in the $k_{on}$).

"Moiety" refers to a portion of a protein. For example, a fusion protein may comprise several moieties. In one embodiment, a fusion protein comprises a fibronectin based scaffold moiety and an Fc moiety. An Fc moiety may comprise a CH2 and a CH3 domain, but does not necessarily comprise a hinge.

A "denatured protein" refers to a protein that is not properly folded (i.e., does not have the proper spatial conformation or three dimensional structure). "Denaturation" refers to a process in which the native conformation of the protein is changed but the primary structure (amino acid chain, peptide links) of the protein remains unchanged. To be able to perform its biological function, a protein folds into a specific spatial conformation, by the action of non-covalent interactions such as ionic interactions, Van Der Waals forces, hydrogen bonding, and hydrophobic packing. A protein that is denatured (i.e., not properly folded) may be a protein that does not have a proper secondary, tertiary or quaternary structure. The secondary structure of a protein or polypeptide refers to highly regular local sub-structures, such as the alpha helix and the beta strand or beta sheets, of a protein. The tertiary structure of a protein or a polypeptide refers to the three-dimensional structure of a single protein molecule, in which the folding of the alpha-helices and beta-sheets into a compact globule is driven by the non-specific hydrophobic interactions (the burial of hydrophobic residues from water), salt bridges, hydrogen bonds, and the tight packing of side chains and disulfide bonds. The quaternary structure of a protein is the three-dimensional structure of subunits of a multi-subunit protein. The subunits of a protein are held together by the same bonds as those that maintain a tertiary structure of a protein. Disulfide bonds contribute to the tertiary and quaternary structure of a protein, polypeptide or polypeptide complex. A denatured protein may be a protein that contains cysteines, but in which the disulfide bonds are not present or are improperly formed. Denatured proteins are generally insoluble and precipitate out of a solution. The presence of one or more disulfide bonds in a protein generally makes its renaturation from a denatured state more challenging. Protein structure can be visualized or determined with various tools, e.g., X-ray crystallography, Nuclear Magnetic Resonance (NMR), circular dichroism and cryo-electron microscopy.

Methods for Refolding Denatured Proteins

When proteins are expressed in certain expression systems, they are produced in a denatured form and must be renatured, i.e., their secondary, tertiary and/or quaternary structure must be reformed. For example, proteins expressed at high levels in *E. coli* are shunted into inclusion bodies (IBs). IBs are essentially made of denatured proteins. The methods described herein may be used to renature unfolded or improperly folded proteins, e.g., present in IBs.

A method for refolding a denatured protein, may comprise: (i) combining denatured protein with a solubilization buffer having a pH in the range of 10 to 13 to thereby obtain a composition comprising solubilized denatured protein; and (ii) combining the composition comprising solubilized denatured protein, with a refold buffer having a pH in the range of 9 to 11 to thereby obtain a composition comprising refolded protein. A method for refolding a denatured protein, may comprise: (i) suspending the denatured protein in a suspension solution to obtain a composition comprising suspended denatured protein; (ii) combining the composition comprising suspended denatured protein with a solubilization buffer having a pH in the range of 10 to 13 to thereby obtain a composition comprising solubilized denatured protein; and (iii) combining the composition comprising solubilized denatured protein, with a refold buffer having a pH in the range of 9 to 11 to thereby obtain a composition comprising refolded protein. When a denatured protein is part of an IB, a method for refolding the protein may comprise: (i) combining the IBs with a solubilization buffer having a pH in the range of 10 to 13 to thereby obtain a composition comprising solubilized IBs; and (ii) combining the composition comprising solubilized IBs with a refold buffer having a pH in the range of 9 to 11 to thereby obtain a composition comprising refolded protein. A method for refolding a protein may comprise (i) suspending IBs comprising a protein in an IB suspension solution to obtain a composition comprising suspended IBs; (ii) combining the composition comprising suspended IBs with a solubilization buffer having a pH in the range of 10 to 13 to thereby obtain a composition comprising solubilized IBs; and (iii) combining the composition comprising solubilized IBs with a refold buffer having a pH in the range of 9 to 11 to thereby obtain a composition comprising refolded protein. A diagram showing exemplary refolding steps is provided in FIG. 1. The first step of the method may be removed.

Certain commonly used methods for refolding denatured proteins known in the art use denaturing agents for solubilizing the denatured proteins. In certain embodiments, the methods described herein or one or more of the compositions, buffers or solutions used in the methods described herein, do not include a significant amount of a denaturing agent. Exemplary denaturing (or chaotropic) agents include: guanidine (or guanidium), guanidium hydrochloride, guanidium chloride, guanidium thiocyanate, urea, thiourea, lithium perchlorate, magnesium chloride, phenol, betain, sarcosine, carbamoyl sarcosine, taurine, dimethylsulfoxide (DMSO); alcohols such as propanol, butanol and ethanol; detergents, such as sodium dodecyl sulfate (SDS), N-lauroyl sarcosine, Zwittergents, non-detergent sulfobetains (NDSB), TRITON™ X-100, NONIDET™ P-40, the TWEEN™ series and BRIJ™ series; hydroxides such as sodium potassium hydroxide, and combinations thereof. A "significant" amount of a denaturant refers to an amount of denaturant that is sufficient to contribute to the solubilization of denatured protein. Certain concentrations of denaturants denature proteins, and these concentrations are referred to as "denaturing concentrations." Certain concentrations of denaturants do not denature proteins, but may contribute to the solubilization of proteins, and these concentrations are referred to as "non-denaturing concentrations." For example, 6 M guanidium is a denaturing concentration, whereas 1M guanidium is not a denaturing concentration. Similarly, urea concentrations of 1-2 M are not considered to be denaturing concentrations. A solution comprising less than a significant amount of a denaturant includes solutions comprising less than a denaturing or non-denaturing concentration of a denaturant. For example, the methods described herein preferably do not include urea or guanidium at a concentration of 1M or more. In certain embodiments, minor amounts of any denaturing agent that is low enough that it does not contribute to denaturation and/or solubilization of a denatured protein may be present at any time in the methods described herein, e.g., in one or more of the compositions, buffers and solutions used in the methods described herein. As defined herein, when referring to methods which do not include the use of a denaturing agent or a significant amount of a denaturing agent, the agent that produces the alkaline conditions in the solubilization buffer is not considered to be a denaturing agent, or in the alternative, if it is considered to be a denaturing agent, then the statement is intended to mean that no other denaturing agent is added or used.

In certain embodiments, a minor amount of a denaturant is an amount of denaturant that is sufficiently low that its inclusion in a refolding method does not require an additional step to later reduce its concentration or remove it from a solution. For example, in certain embodiments, the methods described herein do not include a dialysis step, e.g., they do not include a dialysis step before or after any of the steps of the methods described herein. For example, no dialysis prior to, or after, adding the suspension solution, solubilization buffer or refold buffer is performed.

In certain embodiments, the concentration of a denaturing agent in the methods described herein or in any step of the methods described herein is less than 1M, 100 mM 10 mM, 1 mM, 0.1 mM, $10^{-2}$ mM, $10^{-3}$ mM, $10^{-4}$ mM, $10^{-5}$ mM, or $10^{-6}$ mM. In certain embodiments, no denaturing agent is added to, or present in, one or more of the following solutions used in the methods described herein: the suspension solution, such as an IB suspension solution; the solubilization buffer; and the refold buffer. In certain embodiments, no denaturing agent is used or present in any step in the methods described herein.

In certain embodiments, the concentration of guanidium or salt or analog thereof (e.g., guanidium chloride, guanidium hydrochloride and guanidium thiocyanate) in any step of the methods described herein is less than 1M, 100 mM, 10 mM, 1 mM, 0.1 mM, $10^{-2}$ mM, $10^{-3}$ mM, $10^{-4}$ mM, $10^{-5}$ mM, or $10^{-6}$ mM. In certain embodiments, no guanidium, salt or analog thereof (e.g., guanidium chloride, guanidium hydrochloride and guanidium thiocyanate) is added to, or present in, one or more of the following solutions used in the methods described herein: the suspension solution, such as an IB suspension solution; the solubilization buffer; and the refold buffer. In certain embodiments, no guanidium, salt or analog thereof (e.g., guanidium chloride, guanidium hydrochloride and guanidium thiocyanate) is used or present in any step in the methods described herein. In certain embodiments, the concentration of urea or analog thereof (e.g., dimethylhydroxy urea, dimethylsulphone) in any step of the methods described herein is less than 1M, 100 mM, 10 mM, 1 mM, 0.1 mM, $10^{-2}$ mM, $10^{-3}$ mM, $10^{-4}$ mM, $10^{-5}$ mM, or $10^{-6}$ mM. In certain embodiments, no urea or analogs thereof (e.g., dimethylhydroxy urea and dimethylsulphone) is added to, or present in, one or more of the following solutions used in the methods described herein: the suspension solution, such as an IB suspension solution; the solubilization buffer; and the refold buffer. In certain embodiments, no urea or analogs thereof (e.g., dimethylhydroxy urea and dimethylsulphone) is used or present in any step in the methods described herein. In certain embodiments, the concentration of a detergent, e.g., ionic or non-ionic, in any step of the methods described herein is less than 1M, 100 mM, 10 mM, 1 mM, 0.1 mM, $10^{-2}$ mM, $10^{-3}$ mM, $10^{-4}$ mM, $10^{-5}$ mM, or $10^{-6}$ mM or less than 10%, 1%, 0.1%, 0.01% or 0.001% final concentration. In certain embodiments, no detergent, e.g., ionic or non-ionic, is added to, or present in, one or more of the following solutions used in the methods described herein: the suspension solution, such as an IB suspension solution; the solubilization buffer; and the refold buffer. In certain embodiments, no detergent, e.g., ionic or non-ionic, is used or present in any step in the methods described herein. Non-ionic detergents include TRITON™ X-100, NONIDET™ P-40, the TWEEN™ series and BRIJ™ series. Ionic detergents include deoxycholate, SDS, and CTAB.

In certain embodiments, the methods described herein do not use a significant amount of a reducing agent. A reducing agent is an agent that breaks disulfide bonds by reducing one or the two cysteines of the disulfide bond or maintains cysteines in a reduced state (i.e., maintains free sulfhydryl groups so that the intra- or intermolecular disulfide bonds are chemically disrupted). A "significant amount" of a reducing agent is an amount that is sufficient for reducing at least some disulfide bonds in a protein solution or for maintaining at least some cysteines in a protein solution in a reduced state. Exemplary reducing agents include the following: beta-mercaptoethanol (BME), dithiothreitol (DTT), dithioerythritol (DTE), tris(2-carboxyethyl)phosphine (TCEP), cysteine, cysteamine, thioglycolate, glutathione and sodium borohydride. In certain embodiments, no reducing agent is added to, or present in, one or more of the following solutions used in the methods described herein: the suspension solution, such as an IB suspension solution; the solubilization buffer; and the refold buffer. In certain embodiments, no reducing agent is used or present in any step in the methods described herein. In certain embodiments, the concentration of a reducing agent in any step of the methods described herein is less than 10 mM, 1 mM, 0.1 mM, $10^{-2}$ mM, $10^{-3}$ mM, $10^{-4}$ mM, $10^{-5}$ mM, or $10^{-6}$ mM.

A method for refolding a denatured protein, e.g., a protein that is present in IBs, may include washing the denatured protein, e.g., IBs, prior to suspending them in a suspension solution. Washing denatured protein, e.g., IBs, may be performed with, e.g., Tris/HCL buffer, phosphate buffer, acetate buffer, citrate buffer or water, or a combination of two or more of these.

Suspension of Denatured Protein

Denatured protein, e.g., protein in IBs, which denatured protein may be, e.g., in the form of a pellet (such as a frozen pellet) may be suspended in a suspension solution (or buffer). The denatured protein may be incubated with suspension solution under conditions sufficient to substantially suspend the denatured protein. Incubation may take place under conditions of concentration, incubation time, and incubation temperature to allow suspension of the desired amount or most or substantially all the denatured protein (e.g., at least 70%, 80%, 90%, 95%, 97%, 98% or 99%).

In certain embodiments, the suspension solution is water. Water may be, e.g., tap water, distilled, double distilled, deionized water, reverse osmosed water, or reversed osmosed/deionized (RODI) water. In certain embodiments, a suspension solution comprises low concentrations of a buffer, e.g., TRIS/HCL, e.g., less than about 10 mM, 1 mM, 0.1 mM or less TRIS. A suspension solution may have a pH of 6-10, 6-9, 6-8, 6.5 to 7.5.

In certain embodiments, a pellet of denatured protein is contacted with a suspension solution at a ratio of weight of denatured protein pellet (e.g., IB) (in grams):volume (in ml) of suspension solution (e.g., IB suspension solution) of 1:1-10; 1:1-9; 1:1-8; 1:1-7; 1:1-6; 1:1-5; 1:1-4; 1:1-3; 1:1-2; 1:1; 1:2; 1:3; 1:4; 1; 5; 1:6; 1:7; 1:8 1:9 or 1:10. In certain embodiments, a pellet of denatured protein is contacted with a suspension solution at a ratio of weight of denatured protein pellet (e.g., IB) (in grams):volume (in ml) of suspension solution (e.g., IB suspension solution) of 1:1-3. A weight to volume ratio of "1:3" in this context refers to a ratio of 1 gram of denatured protein to 3 ml of suspension solution. A weight to volume ratio of "1:1-3" in this context refers to a ratio of 1 gram of denatured protein to 1-3 ml (e.g., 1 ml, 2 ml or 3 ml and any values in between) of suspension solution. A weight to volume ratio may also be defined in kgs:liters. The combination of the denatured proteins and the suspension solution is referred to as the "suspension reaction."

The suspension reaction may be conducted at a temperature, e.g., ranging from 2° C. to 40° C.; 4° C. to 37° C.; 25° C. to 37° C.; room temperature; or 4° C. to 25° C. In an exemplary embodiment, a pellet of denatured protein, e.g., an IB pellet, is suspended in water at room temperature (e.g., 25° C.) at a weight (grams) to volume (ml) ratio of denatured protein pellet:suspension solution of 1:1-3, such as 1:1, 1:2 or 1:3.

A suspension reaction may be incubated, and optionally stirred, with a suspension solution until most or essentially all denatured protein has been resuspended, and optionally a fine suspension is obtained. Any portion of a pellet of denatured protein that has not fully been suspended will probably not be renatured efficiently. The proportion of denatured protein that is suspended in the suspension solution may be determined optically. In certain embodiments, the denatured protein is incubated and optionally stirred, e.g., for less than 1 minute, in the suspension buffer. In certain embodiments, the denatured protein is incubated and optionally stirred, e.g., for 1-10 minutes; 1-5 minutes or 1-3 minutes in the suspension solution. Longer incubation times, especially at lower temperatures may also be used.

In certain embodiments, a pellet of denatured protein is suspended in water at a weight (grams) to volume (ml) ratio of denatured protein pellet:volume of suspension solution of 1:1-3, e.g., 1:2, at room temperature and incubated at room temperature for 1-3 minutes, to thereby obtain a composition comprising a suspension of denatured proteins. In an exemplary embodiment, a pellet of IBs is suspended in water at a weight (grams) to volume (ml) ratio of IB:suspension solution of 1:1-3, e.g., 1:2, at room temperature and incubated at room temperature for 1-3 minutes, to thereby obtain a composition comprising an IB suspension.

In certain embodiments, the suspension solution or suspension reaction does not comprise a significant amount of denaturing agent, as further described herein. In certain embodiments, the suspension solution or suspension reaction does not comprise a significant amount of reducing agent, as further described herein. In certain embodiments, the suspension solution or suspension reaction comprises neither a significant amount of denaturing agent nor a significant amount of reducing agent.

Solubilization of Denatured Protein

A suspension of denatured proteins, e.g., an IB suspension, (obtained, e.g., as described above) may be combined with a solubilization buffer to thereby obtain a composition comprising solubilized denatured protein, e.g., solubilized IBs. In certain embodiments, a the denatured protein, e.g., in the form of a pellet, is directly combined with solubilization buffer, without prior suspension. The denatured protein, e.g., in the form of a suspension of denatured proteins, may be incubated with solubilization buffer under conditions sufficient to substantially solubilize the protein. Incubation may take place under conditions of concentration, incubation time, and incubation temperature to allow solubilization of the desired amount or most or substantially all the protein (e.g., at least 70%, 80%, 90%, 95%, 97%, 98% or 99%).

In certain embodiments, a solubilization buffer comprises a buffering agent suitable for maintaining the pH of the solubilization buffer and/or that of the composition comprising the solubilization buffer and denatured protein ("solubilization reaction") in a range of pH 10 to 13. The pH of the solubilization buffer and/or the solubilization reaction may also be within the following ranges of pH: pH 10.5 to 13; pH 11 to 13; pH 11 to 12.8; pH 11.5 to 12.8; pH 11.8 to 12.6; pH 12.0 to 12.6; pH 12.0 to 12.4 and pH 12.2 to 12.5. Exemplary pHs of solubilization buffers and/or solubilization reactions include pH 12.0; pH 12.1; pH 12.2; pH 12.3; pH 12.4 and pH 12.5.

A solubilization buffer may comprise Arginine (or another positively charged amino acid), e.g., L-arginine/HCl (which is encompassed by the term "Arginine"). A solubilization buffer may comprise Arginine at a concentration that is sufficient for buffering the solubilization buffer at the desired pH, e.g., a pH in the range of pH 10.5 to 13; such as pH 12.0 to pH 12.5. Arginine may be present at concentrations in the range of 50 mM to 500 mM; 100 mM to 500 mM; 200 mM to 500 mM; 300 mM to 500 mM; 350 mM to 450 mM. In certain embodiments, the solubilization buffer includes Arginine at a concentration of 300 mM to 400 mM. In certain embodiments, a solubilization buffer comprises Arginine at 50 mM to 500 mM and has a pH in the range of 10.5 to 13. In certain embodiments, a solubilization buffer comprises Arginine at 200 mM to 500 mM and has a pH in the range of 12 to 12.4.

As Arginine buffers the pH of a solution to an alkaline value, it is not necessary to include another buffer in the solubilization buffer. However, in certain embodiments, one may include one or more of the following buffers: TRIS (Tris[hydroxymethyl] aminomethane), HEPES (N-[2-Hydroxyethyl]piperazine-N'-[3-propane-sulfonic acid]), CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), arginine, lysine, and sodium borate. In certain embodiments, the solubilization buffer comprises a buffer, e.g., TRIS, at a concentration of 1 mM to 1 M; 1 mM to 100 mM; 10 mM to 100 nM; 10 mM to 50 mM; 50 mM to 100 mM; 30 mM to 70 mM; or 40 mM to 60 mM. In certain embodiments, the solubilization buffer comprises a buffer, e.g., TRIS, at a concentration of about 50 mM. In certain embodiments, the solubilization buffer comprises TRIS, e.g., at 40-60 mM, and has a pH in the range of pH 12.0 to 12.4.

The solubilization buffer may comprise TRIS and Arginine and have a pH in the range of 12.0 to 12.4. In certain embodiments, the solubilization buffer comprises TRIS at a concentration in the range of 10 mM to 100 mM; Arginine; and have a pH in the range of pH 12.0 to 12.4. The solubilization buffer may comprise TRIS and Arginine, wherein Arginine is at a concentration in the range of 300 mM to 500 mM; and has a pH in the range of 12.0 to 12.4. The solubilization buffer may comprise TRIS at a concentration in the range of 10 mM to 100 mM; Arginine at a concentration in the range of 300 mM to 500 mM; and have a pH in the range of pH 12.0 to 12.4. In certain embodiments, the solubilization buffer comprises TRIS at a concentration in the range of 30 mM to 70 mM; Arginine at a concentration in the range of 300 mM to 500 mM; and has a pH in the range of pH 12.0 to 12.4. In certain embodiments, the solubilization buffer comprises TRIS at a concentration of about 50 mM, Arginine at a concentration of about 400 mM, and has a pH of about 12.2.

The composition comprising the suspended denatured protein, e.g., suspended IBs, may be combined with solubilization buffer at a weight (in grams) to volume (in ml) ratio of weight of denatured protein (e.g., IBs):volume of solubilization buffer of 1:5-50; 1:10-50; 1:10-30; 1:15-25. Exemplary ratios include 1:10, 1:20 and 1:30. For example, for 1 gram of denatured protein (that was suspended in suspension solution), 5-50 ml; 10-50 ml; 10 to 30 ml or 15 to 25 ml of solubilization buffer may be added. In other embodiments, for 1 kg of denatured protein (that was suspended in suspension solution), 5-50 liters; 10-50 liters; 10 to 30 liters or 15 to 25 liters of solubilization buffer may be added.

The solubilization reaction may be conducted at a temperature, e.g., ranging from 2° C. to 40° C.; 4° C. to 37° C.; 25° C. to 37° C.; room temperature; or 4° C. to 25° C. In certain embodiments, the solubilization reaction is conducted at room temperature (e.g., 25° C.) at a weight (in grams) to volume (in ml) ratio of weight of denatured protein (e.g., IBs):volume of solubilization buffer of 1:10-30, e.g., 1:10, 1:20 or 1:30.

The composition comprising the suspended denatured proteins and the solubilization buffer (the "solubilization reaction") is incubated, and optionally stirred, for a time sufficient to solubilize essentially all (e.g., at least 70%, 80%, 90%, 95%, 97%, 98% or 99%) of the protein, e.g., prior to adding the refold buffer. The solubilization reaction may be incubated for less than 1 minute; 1 minute to 6 hours; 1 minute to 5 hours; 1 minute to 3 hours; 1 minute to 2 hours; 1 to 60 minutes; 1 to 30 minutes; 1 to 20 minutes; 1 to 10 minutes; 1 to 5 minutes; 1 to 3 minutes; 1 to 2 minutes; 2 to 5 minutes or 2 to 3 minutes, e.g., prior to adding the refold buffer. The solubilization reaction is preferably performed for a time frame sufficient for most proteins to be solubilized. That most or essentially all of the proteins have been solubilized in the solubilization buffer can be determined optically, as the solution becomes clear (transparent) once all or most of the proteins have been solubilized. At the same time, it is preferable to keep the incubation time of the solubilization reaction as short as possible as deamidation occurs at high pH values. For example, incubation of the solubilization reaction may be conducted for a time that results in less than 15%; 12%; 10%; 7%; 5%; 3%; 2% or 1% deamidation (corresponding, e.g., to total additive percentage of deamidation and isoaspartate formation at multiple sites). Deamidation can be measured, e.g., by Liquid Chomatography Mass Spectrometry (LCMS)/peptide map analysis.

In certain embodiments, a suspension of denatured proteins, e.g., IBs, is combined, and optionally mixed, with a solubilization buffer comprising Arginine at a concentration in the range of 300 mM to 500 mM and optionally TRIS at a concentration in the range of 30 mM to 70 mM; and having a pH in the range of 12.0 to 12.4 at a ratio of weight (grams) of denatured protein:volume (ml) of solubilization buffer of 1:10-30, at room temperature; and wherein incubation is conducted for 2 to 5 minutes prior to, e.g., the addition of refold buffer, to thereby obtain a composition comprising solubilized denatured proteins, e.g., solubilized IBs.

In certain embodiments, the solubilization buffer or solubilization reaction does not comprise a significant amount of denaturing agent, as further described herein. In certain embodiments, the solubilization buffer or solubilization reaction does not comprise a significant amount of reducing agent, as further described herein. In certain embodiments, the solubilization buffer or solubilization reaction comprises neither a significant amount of denaturing agent nor a significant amount of reducing agent.

Protein concentration during the solubilization step may be about 1 mg/ml to about 60 mg/ml, e.g., about 10-50 mg/ml.

Refolding of Denatured Protein

A composition comprising solubilized denatured protein, e.g., a composition comprising solubilized IBs, (obtained, e.g., as described above) may be combined with a refold buffer to thereby obtain a composition comprising refolded protein. The composition comprising solubilized denatured proteins may be incubated with refold buffer under conditions sufficient to substantially refold the protein. Incubation may take place under conditions of concentration, incubation time, and incubation temperature to allow refolding of the desired amount or most or substantially all the protein (e.g., at least 70%, 80%, 90%, 95%, 97%, 98% or 99%).

In certain embodiments, a refold buffer comprises a buffering agent suitable for maintaining the pH of the refold buffer and/or that of the composition comprising the solubilized refold buffer and solubilized protein (the "refold reaction") in a range of pH of 9 to 11. The pH of the refold buffer and/or the refold reaction may also be within the following ranges of pH: pH 9 to 11; pH 9.5 to 11; pH 10 to 11; pH 10 to 10.5; pH 10 to 10.8; and pH 10.2 to 10.6. Exemplary pHs of refold buffers and/or refold reactions include pH 10.0; pH 10.1; pH 10.2; pH 10.3; pH 10.4; pH 10.5; pH 10.6 and pH 10.7.

Refold buffer may comprise Arginine (or another positively charged amino acid), e.g., L-arginine/HCl (which is encompassed by the term "Arginine"). A refold buffer may comprise Arginine at a concentration that is sufficient for buffering the solubilization buffer at the desired pH, e.g., a pH in the range of pH 9 to 11; such as pH 10 to 10.8. Arginine may be present at concentrations in the range of 50 mM to 500 mM; 100 mM to 500 mM; 200 mM to 500 mM; 300 mM to 500 mM; 350 mM to 450 mM. In certain embodiments, the refold buffer includes Arginine at a concentration of 300 mM to 400 mM. In certain embodiments, a refold buffer comprises Arginine at 50 mM to 500 mM and has a pH in the range of 9 to 11. In certain embodiments, a refold buffer comprises Arginine at 200 mM to 500 mM and has a pH in the range of pH 10 to 10.8.

As Arginine is buffering the refold solution at pH 10.4, it is not necessary to include another buffer. However, if desired, any of the following buffers may be added: TRIS (Tris[hydroxymethyl]aminomethane), HEPPS (N-[2-Hydroxyethyl]piperazine-N'-[3-propane-sulfonic acid]), CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), arginine, lysine, and sodium borate. In certain embodiments, the refold buffer includes a buffer, e.g., TRIS, at a concentration of 1 mM to 1 M; 1 mM to 100 mM; 10 mM to 100 nM; 10 mM to 50 mM; 50 mM to 100 mM; 30 mM to 70 mM; or 40 mM to 60 mM. In certain embodiments, the refold buffer comprises a buffer, e.g., TRIS, at a concentration of about 50 mM. In certain embodiments, the refold buffer comprises TRIS, e.g., at 40-60 mM, and has a pH in the range of pH 10.2 to 10.6.

The refold buffer may comprise TRIS and Arginine and have a pH in the range of pH 10.2 to 10.6. In certain embodiments, the refold buffer comprises TRIS at a concentration in the range of 10 mM to 100 mM; Arginine; and has a pH in the range of pH 10.2 to 10.6. The refold buffer may comprise TRIS and Arginine, wherein Arginine is at a concentration in the range of 300 mM to 500 mM; and have a pH in the range of pH 10.2 to 10.6. The refold buffer may comprise TRIS at a concentration in the range of 10 mM to 100 mM; Arginine at a concentration in the range of 300 mM to 500 mM; and have a pH in the range of pH 10.2 to 10.6. In certain embodiments, the refold buffer comprises TRIS at a concentration in the range of 30 mM to 70 mM; Arginine at a concentration in the range of 300 mM to 500 mM; and have a pH in the range of pH 10.2 to 10.6. In certain embodiments, the solubilization buffer comprises TRIS at a concentration of about 50 mM, Arginine at a concentration of about 400 mM, and has a pH of about 10.4.

In embodiments, in which the protein to be refolded comprise one or more disulfide bonds when properly folded, the refold buffer may also comprise an oxidizing agent to facilitate the formation of disulfide bonds. For refolding proteins that do not comprise a disulfide bond, it is not necessary to include an oxidizing agent. In certain embodiments, the oxidizing agent comprises glutathione, e.g., in a ratio of oxidized glutathione:reduced glutathione of about 5:1 or a similar ratio sufficient to facilitate the formation of disulfide bonds. In certain embodiments, a refold buffer comprises 0.1 mM to 10 mM of oxidized glutathione and 0.02 mM to 2 mM of reduced glutathione. In certain embodiments, a refold buffer comprises 0.5 mM to 2 mM of oxidized glutathione and 0.1 to 0.4 mM of reduced glutathione. In certain embodiments, a refold buffer comprises about 1 mM of oxidized glutathione and about 0.2 mM of reduced glutathione. Other oxidizing agents known in the art may also be used.

A composition comprising solubilized protein may be combined with refold buffer at a ratio of volume (ml) of solubilization buffer used to solubilize the denatured protein: volume (ml) of refold buffer of 1:1-50; 1:1-20; 1:1-10; 1:1-5; 1:2-10; 1:2-8; or 1:2-5. Exemplary ratios include about 1:1, 1:2, 1:3, 1:4; 1:5 or 1:6.

The refold reaction may be conducted at a temperature, e.g., ranging from 2° C. to 40° C.; 4° C. to 37° C.; 25° C. to 37° C.; room temperature; or 4° C. to 25° C. In certain embodiments, the refold reaction is conducted at room temperature (e.g., 25° C.) at a ratio of volume (ml) of solubilization buffer used to solubilize the denatured protein: volume (nil) of refold buffer of 1:1-5, e.g., 1:1, 1:3 or 1:5.

Refold occurs essentially instantaneously, and is generally performed for a time frame sufficient for most proteins to be refolded. In certain embodiments, the refold reaction may be incubated (e.g., with or without stirring), e.g., overnight; for 1 minute to 12 hours; 1 minute to 6 hours; 1 minute to 3 hours; 1 to 120 minutes; 1 to 30 minutes; 1 to 20 minutes; 1 to 10 minutes; 1 to 100 minutes; 10 to 100 minutes; 10 to 80 minutes; 20 to 60 minutes prior to, e.g., adjusting the pH down. Incubation may be performed with or without stirring. In certain embodiments, the refold reaction is stirred and then incubated without stirring.

In certain embodiments, a composition comprising solubilized proteins is combined with a refold buffer comprising Arginine at a concentration in the range of 300 mM to 500 mM; oxidized glutathione at a concentration in the range of 0.5 mM to 2 mM; (optionally TRIS at a concentration in the range of 30 mM to 70 mM) reduced glutathione at a concentration in the range of 0.1 to 0.4 mM, and having a pH in the range of 10.2 to 10.6, at a volume ratio of solubilization buffer:refold buffer of 1:1-5, and incubated at room temperature for 1 minute to overnight, prior to, e.g., adjusting the pH to a lower value.

In certain embodiments, the refold buffer or refold reaction does not comprise a significant amount of denaturing agent, as further described herein. In certain embodiments, the refold buffer or refold reaction does not comprise a significant amount of reducing agent (except when co-administered together with an oxidant, e.g., when oxidized and reduced glutathione are added together), as further described herein. In certain embodiments, the refold buffer or refold reaction comprises neither a significant amount of denaturing agent nor a significant amount of reducing agent.

Following the refolding reaction, the pH may be adjusted to a lower value, e.g., pH 6 to 8 or pH 7 to 8. In certain embodiments, the pH is adjusted to about pH 8. In certain embodiments, adjusting the pH down to about pH 8 comprises adding 0.3 fold volume of 1M HCl. The addition of the HCl may be conducted slowly, e.g., over 0.5 to 2 minutes.

Following the adjustment to a lower pH, the reaction mixture may be incubated for 30 minutes to 3 hours; for 30 minutes to 2 hours, or overnight, prior to a next step, e.g., a purification step. A refolded protein may be further processed, e.g., purified, according to methods known in the art, e.g., using protein A chromatography and other types of chromatography or purification methods.

Protein concentration during the refold step may be from 1 mg/ml or less to about 10 mg/ml. For example, the protein concentration may be about 5 mg/ml, 6 mg/ml or 7 mg/ml.

In certain embodiments, total recovery of protein refolded as described herein may be greater than 70% or 80% as measured by reverse phase chromatography. Total downstream processing recoveries may be as high as 20%, 30%, 40% or more from solubilization of the denatured protein, e.g., IBs, through final chromatography.

During standard expression and purification of recombinant protein comprising an Fc, the disulfide bond of the CH3 loop breaks in about 0.5-5% of the protein composition. Using certain methods described herein, the CH3 open loop has been shown to be in the range of 0.5-3% in the refolded proteins. Accordingly certain Fc containing protein compositions, wherein the proteins have been refolded as described herein, have less than 5%, 4%, 3%, 2%, 1% CH3 open loops. It has also been shown herein that deamidation can be reduced from 40% to 12% (total additive percentage of deamidation and isoasp formation at multiple sites). Accordingly, in certain embodiments, protein refolded using a method described herein comprise less than 40%, 30%, 20%, 15%, or 13% deamidation.

In certain embodiments, refolding denatured protein, e.g., from an IB, is performed in less than 4 hours, 3 hours, or 2 hours.

Exemplary Methods

A method for refolding a denatured protein, e.g., from an IB, may comprise: (i) suspending a pellet of denatured protein, e.g., an IB pellet, in suspension solution (e.g., water) at a ratio of weight (grams) of denatured protein pellet: volume (ml) of suspension solution of 1:1-3 at room temperature for a time sufficient for most of the denatured protein to be suspended, e.g., 1-10 minutes, to thereby obtain a composition comprising a suspension of denatured protein; (ii) combining (and optionally mixing) the composition comprising a suspension of denatured protein with a solubilization buffer comprising Arginine at a concentration sufficient to buffer the solubilization buffer to a pH in the range of pH 12.0 to 12.4, e.g., in the range of 100 mM to 500 mM (and optionally TRIS at a concentration in the range of 10 mM to 100 mM); at a ratio of weight (grams) of denatured protein:volume (ml) of solubilization buffer of 1:10-30, wherein the incubation is conducted at room temperature for a time sufficient to solubilize most of the denatured protein, e.g., 2 to 5 minutes, to thereby obtain a composition comprising solubilized denatured protein; and (iii) combining the composition comprising solubilized denatured protein with a refold buffer comprising Arginine at a concentration sufficient to buffer the refold buffer to a pH in the range of pH 10.2 to 10.6, e.g., at a concentration in the range of 100 mM to 500 mM (and optionally TRIS at a concentration in the range of 10 mM to 100 mM); a concentration of oxidizing agent sufficient to promote disulfide bond formation, e.g., oxidized glutathione at a concentration in the range of 0.5 mM to 2 mM and reduced glutathione at a concentration in the range of 0.1 mM to 0.4 mM; at a ratio of volume of solubilization buffer used in step (ii):volume of refold buffer of 1:1-5, wherein the incubation is conducted at room temperature for a time sufficient to refold most of the protein, e.g., for 1 minute to overnight; and wherein the method does not comprise using a significant amount of denaturing agent and optionally does not comprise using a significant amount of a reducing agent (other than the reduced agent that is used together with the oxidizing agent).

In certain embodiments, a method for refolding a denatured protein, e.g., from an IB, comprises: (i) suspending a pellet of denatured protein, e.g., an IB pellet, in water at a volume ratio of weight (grams) of denatured protein pellet:volume (ml) of water of 1:1-3 at room temperature for 1-10 minutes to thereby obtain a composition comprising a suspension of denatured protein; (ii) combining and mixing the composition comprising a suspension of denatured protein with a solubilization buffer comprising Arginine at a concentration in the range of 300 mM to 500 mM (and optionally TRIS at a concentration in the range of 30 mM to 70 mM); and having a pH in the range of pH 12.0 to 12.4; at a ratio of weight (grams) of denatured protein:volume (ml) of solubilization buffer of 1:10-30, wherein the incubation is conducted at room temperature for 2 to 5 minutes, to thereby obtain a composition comprising solubilized denatured protein; and (iii) combining the composition comprising solubilized denatured protein with a refold buffer comprising Arginine at a concentration in the range of 300 mM to 500 mM (and optionally TRIS at a concentration in the range of 30 mM to 70 mM); oxidized glutathione at a concentration in the range of 0.5 mM to 2 mM; reduced glutathione at a concentration in the range of 0.1 mM to 0.4 mM; and having a pH in the range of pH 10.2 to 10.6; at a ratio of volume of solubilization buffer used in step (ii):volume of refold buffer of 1:1-5, wherein the incubation is conducted at room temperature for 1 to 120 minutes; and wherein the method does not comprise using a significant amount of denaturing agent and optionally does not comprising using a significant amount of a reducing agent (other than the reduced agent that is used together with the oxidizing agent).

Generally, the margin of error of pH for a prepared buffer solution is +/−0.1 units.

Exemplary Proteins

Proteins that may be refolded from a denatured state, e.g., from IBs, using the methods described herein include any protein that is in a denatured form, e.g., proteins comprising at least one disulfide bond in their native state. Proteins without disulfide bonds may also be refolded as described herein. Proteins may comprise a binding domain that specifically binds to a target protein. A protein may be a naturally occurring protein or a genetically engineered or fusion protein. An exemplary protein that may be refolded as described herein is an Fc containing protein, such as an Fc fused to a heterologous domain (e.g., a non-Fc or non-antibody domain). A heterologous protein may be any protein, including an antigen binding portion of an antibody and derivatives thereof, e.g., Fabs, scFvs, bispecific scFvs, single domain antibodies ("sdAbs") (e.g., $V_HH$ or camelid antibodies and $V_{NAR}$s), diabodies (dAbs), single chain diabodies (scDb), Darpins, anticalins, and fibronectin based scaffolds, such as $^{10}$Fn3, Fibcons and Tencons. A full length antibody may also be refolded as described herein. Heterologous proteins linked to Fc may also be unrelated to antibodies and may be, e.g., TNFR.

Fibronectin Based Scaffolds

As used herein, a "fibronectin based scaffold" or "FBS" protein or moiety refers to proteins or moieties that are based on a fibronectin type III ("Fn3") repeat. Fn3 is a small (about 10 kDa) domain that has the structure of an immunoglobulin (Ig) fold (i.e., an Ig-like β-sandwich structure, consisting of seven β-strands and six loops). Fibronectin has 18 Fn3 repeats, and while the sequence homology between the repeats is low, they all share a high similarity in tertiary structure. Fn3 domains are also present in many proteins other than fibronectin, such as adhesion molecules, cell surface molecules, e.g., cytokine receptors, and carbohydrate binding domains. For reviews see Bork & Doolittle, Proc Natl Acad Sci USA 89(19):8990-4 (1992); Bork et al., J Mol Biol. 242(4):309-20 (1994); Campbell & Spitzfaden, Structure 2(5):333-7 (1994); Harpez & Chothia, J Mol Biol. 238(4):528-39 (1994)). The term "fibronectin based scaffold" protein or moiety is intended to include scaffolds based on Fn3 domains from these other proteins (i.e., non fibronectin molecules).

An example of fibronectin-based scaffold proteins are Adnectins (Adnexus, a wholly owned subsidiary of Bristol-Myers Squibb). It has been shown that the CDR-like loop regions of the fibronectin based scaffolds can be modified to evolve a protein capable of binding to any compound of interest. For example, U.S. Pat. No. 7,115,396 describes Fn3 domain proteins wherein alterations to the BC, DE, and FG loops result in high affinity TNFα binders. U.S. Pat. No. 7,858,739 describes Fn3 domain proteins wherein alterations to the BC, DE, and FG loops result in high affinity VEGFR2 binders.

An Fn3 domain is small, monomeric, soluble, and stable. It lacks disulfide bonds and, therefore, is stable under reducing conditions. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole"). Any or all of loops AB, BC, CD, DE, EF and FG may participate in ligand binding.

In exemplary embodiments, the ligand binding fibronectin based scaffold moieties described herein are based on the tenth fibronectin type III domain, i.e., the tenth module of Fn3 ($^{10}$Fn3). The amino acid sequence of wild-type human $^{10}$Fn3 (with N-terminal tail (in italics)) is set forth in SEQ ID NO: 1:

(SEQ ID NO: 1)
*VSDVPRDL*EVVAA<u>TPTSLLI</u>SWDAPAVTVRYYRITY<u>GETGGNS</u>PVQEFTV
PGSKSTATISGL<u>KPGVD</u>YTITVYAVTGRGDSPASSKPISINYR*TEIDKPS
Q*

(the AB, CD and EF loops are underlined; the BC, FG, and DE loops are emphasized in bold; the β-strands are located between each of the loop regions; and the N-terminal and C-terminal regions are shown in italics). Wild-type $^{10}$Fn3 without the tail set forth in italics in SEQ ID NO: 1 is provided as SEQ ID NO: 5.

In some embodiments, the AB loop corresponds to residues 14-17, the BC loop corresponds to residues 23-31, the CD loop corresponds to residues 37-47, the DE loop corresponds to residues 51-56, the EF loop corresponds to residues 63-67, and the FG loop corresponds to residues 75-87 of SEQ ID NO: 1. The BC, DE and FG loops align along one face of the molecule, i.e. the "north pole", and the AB, CD and EF loops align along the opposite face of the molecule, i.e. the "south pole". In SEQ ID NO: 1, β-strand A corresponds to residues 8-13, β-strand B corresponds to residues 18-22, β-strand C corresponds to residues 32-36, beta strand D corresponds to residues 48-50, β-strand E corresponds to residues 57-62, β-strand F corresponds to residues 68-74, and β-strand G corresponds to residues 88-92. The β-strands are connected to each other through the corresponding loop, e.g., strands A and B are connected via loop AB in the formation β-strand A, loop AB, β-strand B, etc. The N-terminal and/or C-terminal regions of SEQ ID NO: 1 (italicized above), may be removed or altered to generate a molecule retaining biological activity and comprising, e.g., an amino acid sequence selected from the group consisting of SEQ ID NOs: 2-16. In certain embodiments, the first 8 amino acid residues of SEQ ID NO: 1 and/or the last 7 amino acid residues of SEQ ID NO: 1 (i.e., amino acid residues 1-8 and 95-101 of SEQ ID NO: 1, respectively) may be removed or altered to generate a polypeptide comprising the amino acid sequence of SEQ ID NO: 4.

As described above, amino acid residues corresponding to residues 14-17, 23-31, 37-47, 51-56, 63-67 and 75-87 of SEQ ID NO: 1 define the AB, BC, CD, DE, EF and FG loops, respectively. However, it should be understood that not every residue within a loop region needs to be modified in order to achieve a $^{10}$Fn3 binding domain having strong affinity for a desired target. Additionally, insertions and deletions in the loop regions may also be made while still producing high affinity $^{10}$Fn3 binding domains.

Accordingly, in some embodiments, one or more loops selected from AB, BC, CD, DE, EF and FG may be extended or shortened in length relative to the corresponding loop in wild-type human $^{10}$Fn3. In any given polypeptide, one or more loops may be extended in length, one or more loops may be reduced in length, or combinations thereof. In some embodiments, the length of a given loop may be extended by 2-25, 2-20, 2-15, 2-10, 2-5, 5-25, 5-20, 5-15, 5-10, 10-25, 10-20, or 10-15 amino acids. In some embodiments, the length of a given loop may be reduced by 1-15, 1-11, 1-10, 1-5, 1-3, 1-2, 2-10, or 2-5 amino acids. In particular, the FG loop of $^{10}$Fn3 is 13 residues long, whereas the corresponding loop in antibody heavy chains ranges from 4-28 residues. To optimize antigen binding in polypeptides relying on the FG for target binding, therefore, the length of the FG loop of $^{10}$Fn3 may be altered in length as well as in sequence to obtain the greatest possible flexibility and affinity in target binding.

In some embodiments, one or more residues of the integrin-binding motif "arginine-glycine-aspartic acid" (RGD) (amino acids 78-80 of SEQ ID NO: 1) may be substituted so as to disrupt integrin binding. In some embodiments, the FG loop of the polypeptides provided herein does not contain an RGD integrin binding site. In one embodiment, the RGD sequence is replaced by a polar amino acid-neutral amino acid-acidic amino acid sequence (in the N-terminal to C-terminal direction). In another embodiment, the RGD sequence is replaced with SGE. In yet another embodiment, the RGD sequence is replaced with RGE (see, e.g., SEQ ID NO: 16).

As used herein, a "$^{10}$Fn3 domain" or "$^{10}$Fn3 moiety" refers to wild-type $^{10}$Fn3 (e.g., comprising one of SEQ ID NOs: 1-8, 10, 12, 14 or 16) and biologically active variants thereof, e.g., biologically active variants that specifically bind to a target, such as a target protein and biologically active variants having SEQ ID NO: 9, 11, 13 or 15. A wild type $^{10}$Fn3 domain may comprise one of the amino acid sequenced set forth in SEQ ID NO: 1-8, 10, 12, 14 and 16. Biologically active variants of a $^{10}$Fn3 domain include $^{10}$Fn3 domains that comprise at least, at most or about 1, 2, 3, 4, 5, 6, 7, 8, 9, 10, 11, 12, 13, 14, 15, 16, 17, 18, 19, 20, 21, 22, 23, 24, 25, 30, 35, 40 or 45 amino acid changes, i.e., substitutions, additions or deletions, relative to a $^{10}$Fn3 domain comprising any one of SEQ ID NOs: 1-16. A biologically active variant of a $^{10}$Fn3 domain may also comprise, or comprise at most, 1-3, 1-5, 1-10, 1-15, 1-10, or 1-25 amino acid changes relative to a $^{10}$Fn3domain comprising any one of SEQ ID NOs: 1-16. In certain embodiments, a biologically active variant of a $^{10}$Fn3domain does not comprise more than 1, 2, 3, 4, 5, 6, 7, 8, 9, 10, 11, 1, 2, 13, 14, 15, 16, 17, 18, 19, 20, 21, 22, 23, 24, 25, 30, 35, 40 or 45 amino acid changes, i.e., substitutions, additions or deletions, relative to an $^{10}$Fn3domain comprising any one of SEQ ID NOs: 1-16. Amino acid changes may be in a loop region and/or in a strand. Exemplary degenerate $^{10}$Fn3 amino acid sequences are provided herein as SEQ ID NOs: 17-29.

In some embodiments, a fibronectin based scaffold moiety comprises a $^{10}$Fn3 domain having at least 40%, 50%, 55%, 60%, 65%, 70%, 75%, 80%, 85%, or 90% identity to a human $^{10}$Fn3 domain having an amino acid sequence selected from the group of sequence comprising SEQ ID NOs: 1-16. In certain embodiments, the fibronectin based scaffold moiety provided herein have at least 50% identity to an amino acid sequence selected from the group of amino acid sequences comprising SEQ ID NO: 1-16. In other embodiments, the fibronectin based scaffold moiety has at least 65% identity to an amino acid sequence selected from the group of amino acid sequences comprising SEQ ID NO: 1-16. In certain embodiments, one or more of the loops will not be modified relative to the sequence of the corresponding loop of the wild-type sequence and/or one or more of the β-strands will not be modified relative to the sequence of the corresponding β-strand of the wild-type sequence. In certain embodiments, each of the beta or beta-like strands of a $^{10}$Fn3 domain in a fibronectin based scaffold moiety may comprise, consist essentially of, or consist of an amino acid sequence that is at least 80%, 85%, 90%, 95% or 100% identical to the sequence of a corresponding beta or beta-like strand of SEQ ID NO: 1. Preferably, variations in the β-strand regions will not disrupt the stability of the polypeptide in physiological conditions. In exemplary embodiments, the $^{10}$Fn3 domain binds to a desired target with a $K_d$ of less than 500 nM, 100 nM, 50 nM, 10 nM, 5 nM, 1 nM, 500 pM, 100 pM or less. In some embodiments, the $^{10}$Fn3 domain of a fibronectin based protein scaffold binds to a desired target with a $K_d$ between 1 pM and 1 μM, between 100 pM and 500 nM, between 1 nM and 500 nM, or between 1 nM and 100 nM. In exemplary embodiments, the fibronectin based scaffold moiety binds specifically to a target that is not bound by a wild-type $^{10}$Fn3 domain, particularly the wild-type human $^{10}$Fn3 domain having, e.g., SEQ ID NO: 1-8, 10, 12, 14 or 16.

In some embodiments, fusion proteins comprise a fibronectin based scaffold moiety comprising a $^{10}$Fn3 domain, wherein the $^{10}$Fn3 domain comprises a loop, AB; a loop, BC; a loop, CD; a loop, DE; a loop, EF; and a loop, FG; and has at least one loop selected from loop AB, BC, CD, DE, EF and FG with an altered amino acid sequence relative to the sequence of the corresponding loop of the human $^{10}$Fn3 domain of SEQ ID NO: 1-16. In some embodiments, the BC, DE and FG loops are altered. In certain embodiments, the AB, CD and EF loops are altered. In certain embodiments, the FG loop is the only loop that is altered. In other embodiments, the CD and FG loops are both altered, and optionally, no other loops are altered. In certain embodiments, the CD and EF loops are both altered, and optionally, no other loops are altered. In some embodiments, one or more specific scaffold alterations are combined with one or more loop alterations. By "altered" is meant one or more amino acid sequence alterations relative to a template sequence (i.e., the corresponding wild-type human fibronectin domain) and includes amino acid additions, deletions, and substitutions.

In some embodiments, the fibronectin based scaffold moiety comprises a $^{10}$Fn3 domain wherein the non loop regions comprise an amino acid sequence that is at least 80, 85, 90, 95, 98, or 100% identical to the non-loop regions of SEQ ID NO: 1, wherein at least one loop selected from AB, BC, CD, DE, EF and FG is altered. For example, in certain embodiments, the AB loop may have up to 4 amino acid substitutions, up to 10 amino acid insertions, up to 3 amino acid deletions, or a combination thereof; the BC loop may have up to 10 amino acid substitutions, up to 4 amino acid deletions, up to 10 amino acid insertions, or a combination thereof; the CD loop may have up to 6 amino acid substitutions, up to 10 amino acid insertions, up to 4 amino acid deletions, or a combination thereof; the DE loop may have up to 6 amino acid substitutions, up to 4 amino acid deletions, up to 13 amino acid insertions, or a combination thereof; the EF loop may have up to 5 amino acid substitutions, up to 10 amino acid insertions, up to 3 amino acid deletions, or a combination thereof; and/or the FG loop may have up to 12 amino acid substitutions, up to 11 amino acid deletions, up to 25 amino acid insertions, or a combination thereof.

In certain embodiments, a fibronectin based scaffold moiety comprises an amino acid sequence that is at least 40%, 50%, 60%, 70%, 75%, 80%, 85%, 90%, 95%, 97%, 98%, or 99% identical to an amino acid sequence selected from the group of sequences consisting of SEQ ID NOs: 1-16, and the fusion protein binds specifically to a target, e.g., with a $K_d$ of less than 500 nM, 100 nM, 50 nM, 10 nM, 5 nM, 1 nM, 500 pM, 100 pM or less. The proteins may comprise amino acid changes (or alterations) in one or more loops and one or more strands.

In certain embodiments, the fibronectin based scaffold moiety comprises a $^{10}$Fn3 domain that is defined generally by following the sequence:

```
                                        (SEQ ID NO: 17)
VSDVPRDLEVVAA(X)_uLLISW(X)_vYRITY(X)_wFTV(X)_xATISGL
(X)_yYTITVYA(X)_zISINYRT,
``` or by the sequence having SEQ ID NO: 18-29. In SEQ ID NOs: 17-29, the AB loop is represented by $(X)_u$, the BC loop is represented by $(X)_v$, the CD loop is represented by $(X)_w$, the DE loop is represented by $(X)_x$, the EF loop is represented by $(X)_y$ and the FG loop is represented by $X_z$. X represents any amino acid and the subscript following the X represents an integer of the number of amino acids. In particular, u, v, w, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. The sequences of the beta strands (underlined) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NOs: 17-29. In some embodiments, the sequences of the beta strands may have anywhere from 0 to 10, from 0 to 8, from 0 to 6, from 0 to 5, from 0 to 4, from 0 to 3, from 0 to 2, or from 0 to 1 substitutions, e.g., conservative substitutions, across all 7 scaffold regions relative to the corresponding amino acids shown in SEQ ID NO: 17-29. In certain embodiments, the hydrophobic core amino acid residues (bolded residues in SEQ ID NO: 17 above) are fixed, and any substitutions, conservative substitutions, deletions or additions occur at residues other than the hydrophobic core amino acid residues. In some embodiments, the hydrophobic core residues of the polypeptides provided herein have not been modified relative to the wild-type human $^{10}$Fn3 domain (e.g., SEQ ID NO: 1 or 5).

In some embodiments, the amino acid sequences of the N-terminal and/or C-terminal regions of a fibronectin based scaffold moiety may be modified by deletion, substitution or insertion relative to the amino acid sequences of the corresponding regions of $^{10}$Fn3 domains comprising one of SEQ ID NOs: 1-16). In some embodiments, the first eight (i.e., residues 1-8) and the last seven amino acids (i.e., residues 95-101) of SEQ ID NO: 1 are deleted, generating a $^{10}$Fn3 domain having the amino acid sequence of SEQ ID NO: 4. Additional sequences may also be added to the N- or C-terminus of a $^{10}$Fn3 domain having the amino acid sequence of any one of SEQ ID NOs: 1-16. For example, in some embodiments, the N-terminal extension consists of an amino acid sequence selected from the group consisting of: M, MG, and G.

In certain embodiments, the amino acid sequence of the first 1, 2, 3, 4, 5, 6, 7, 8 or 9 residues of SEQ ID NO: 1 may be modified or deleted in the polypeptides provided herein relative to the sequence of the corresponding amino acids in the wild-type human $^{10}$Fn3 domain having SEQ ID NO: 1. In exemplary embodiments, the amino acids corresponding to amino acids 1-8 of SEQ ID NO: 1 are replaced with an alternative N-terminal region having from 1-20, 1-15, 1-10, 1-8, 1-5, 1-4, 1-3, 1-2, or 1 amino acids in length. Exemplary alternative N-terminal regions include (represented by the single letter amino acid code) M, MG, G, MGVSDVPRDL (SEQ ID NO: 30) and GVSDVPRDL (SEQ ID NO: 31), or N-terminal truncations of any one of SEQ ID NOs: 30 and 31. Other suitable alternative N-terminal regions include, for example, $X_n$SDVPRDL (SEQ ID NO: 32), $X_n$DVPRDL (SEQ ID NO: 33), $X_n$VPRDL (SEQ ID NO: 34), $X_n$PRDL (SEQ ID NO: 35), $X_n$RDL (SEQ ID NO: 36), $X_n$DL (SEQ ID NO: 37), or $X_n$L, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus. In other embodiments, the alternative N-terminal region comprises the amino acid sequence MASTSG (SEQ ID NO: 38).

In certain embodiments, the amino acid sequence corresponding to amino acids 93-101, 94-101, 95-101, 96-101, 97-101, 98-101, 99-101, 100-101, or 101 of SEQ ID NO: 1 are deleted or modified in the polypeptides provided herein relative to the sequence of the corresponding amino acids in the wild-type human $^{10}$Fn3 domain (SEQ ID NO: 1). In exemplary embodiments, the amino acids corresponding to amino acids 95-101 of SEQ ID NO: 1 are replaced with an alternative C-terminal region having from 1-20, 1-15, 1-10, 1-8, 1-5, 1-4, 1-3, 1-2, or 1 amino acids in length. Specific examples of alternative C-terminal region sequences include, for example, polypeptides comprising, consisting essentially of, or consisting of, EIEK (SEQ ID NO: 39), EGSGC (SEQ ID NO: 40), EIEKPCQ (SEQ ID NO: 41), EIEKPSQ (SEQ ID NO: 42), EIEKP (SEQ ID NO: 43), EIEKPS (SEQ ID NO: 44), EIEKPC (SEQ ID NO: 45), or HHHHHH (SEQ ID NO: 46). In some embodiments, the alternative C-terminal region comprises EIDK (SEQ ID NO: 47), and in particular embodiments, the alternative C-terminal region is either EIDKPCQ (SEQ ID NO: 48) or EIDKPSQ (SEQ ID NO: 49).

In certain embodiments, a fibronectin based scaffold moiety comprises a $^{10}$Fn3 domain having both an alternative N-terminal region sequence and an alternative C-terminal region sequence.

In certain embodiments, a fibronectin based scaffold moiety is based on an Fn3 repeat other than the $10^{th}$ repeat of the type III domain of fibronectin, e.g., human fibronectin. For example, a fibronectin based scaffold moiety may be similar to any of $9^{th}$, the other fibronectin type III repeats, e.g., the $1^{st}$, $2^{nd}$, $3^{rd}$, $4^{th}$, $5^{th}$, $6^{th}$, $7^{th}$, $8^{th}$, $9^{th}$, $11^{th}$, $12^{th}$, $13^{th}$, $14^{th}$, $15^{th}$, $16^{th}$, $17^{th}$, and $18^{th}$ Fn3 repeats. In yet other embodiments, a fibronectin based scaffold moiety may be from a molecule other than fibronectin. Exemplary fibronectin based scaffold moieties may be derived from tenascin, a protein that is composed of 15 Fn3 domains with similar sequence similarities to one another as found in fibronectin. These repeats are described, e.g., in Jacobs et al. (2012) Protein Engineering, Design & Selection 25:107. Based on the homology of the repeats in the fibronectin molecule and those in the tenascin molecule, artificial molecules based on these homologies have been created. The consensus amino acid sequences based on the homology of the domains in the fibronectin molecule are referred to as Fibcon and FibconB (WO2010/093627 and Jacobs et al. (2012) supra) and those based on the homology of the domains in the tenascin molecule are referred to as Tencon. An exemplary Fibcon amino acid sequence comprises the following amino acid sequence: MPAPTDLRFTNETPSSLLISWTPPRVQITG-YIIRYGPVGSDGRVKEFTVPPSVSSATI TGLKPGTEY-TISVIALKDNQESEPLRGRVTTGG (FibconB; SEQ ID NO: 50), wherein loop AB consists of amino acids 13-16 (TPSS; SEQ ID NO: 51), loop BC consists of amino acids 22-28 (TPPRVQI; SEQ ID NO: 52), loop CD consists of amino acids 38-43 (VGSDGR; SEQ ID NO: 53), loop DE consists of amino acids 51-54 (PSVS; SEQ ID NO: 54), loop EF consists of amino acids 60-64 (GLKPG; SEQ ID NO: 55) and loop FG consist of amino acids 75-81 (KDNQESEP; SEQ ID NO: 56). Another Fibcon amino acid sequence comprises the following amino acid sequence:

```
LDAPTDLQVTNVTDTSITVSWTPPSATITGYRITYTPSNGPGEPKELTVP
PSSTSVTITGITPGVEYVVSVYALKDNQESPPLVGTCTT (SEQ ID
NO: 57; Jacobs et al., supra).
```

Tenascin derived Fn3 proteins include Tencons (WO2010/051274, WO2010/051310 and WO2011/137319, which are specifically incorporated by reference herein). An exemplary Tencon protein has the following amino acid sequence: LPAPKNLVVSEVTEDSLRLSWTAPDAAFD-SFLIQYQESEKVGEAINLTVPGSERSY DLTGLKPGTE-YTVSIYGVKGGHRSNPLSAEFTT (SEQ ID NO: 58; Jacobs et al., supra, and WO2011/137319), wherein loop AB consists of amino acids 13-16 (TEDS; SEQ ID NO: 59, loop BC consists of amino acids 22-28 (TAPDAAF; SEQ ID NO: 60), loop CD consists of amino acids 38-43 (SEKVGE; SEQ ID NO: 61), loop DE consists of amino acids 51-54 (GSER; SEQ ID NO: 62), loop EF consists of amino acids 60-64 (GLKPG; SEQ ID NO: 63) and loop FG consists of amino acids 75-81 (KGGHRSN; SEQ ID NO: 64).

A Fibcon, FibconB or Tencon moiety, or target binding variants thereof, whether by themselves or linked to a heterologous moiety, e.g., an Fc, may be refolded as described herein. Fn3 domains from other proteins, e.g., cell surface hormone and cytokine receptors, chaperonins, and carbohydrate-binding domains, may also be refolded as described herein, either on their own or as part of a fusion protein to, e.g., Fc.

Fibronectin based scaffold proteins or moieties are described, e.g., in WO2010/093627, WO2011/130324, WO2009/083804, WO2009/133208, WO02/04523, WO2012/016245, WO2009/023184, WO2010/051310, WO2011/020033, WO2011/051333, WO2011/051466, WO2011/092233, WO2011/100700, WO2011/130324, WO2011/130328, WO2011/137319, WO2010/051274, WO2009/086116, WO09/058379 and WO2013/067029 (all of which are specifically incorporated by reference herein, in particular, the various types of molecules are specifically incorporated by reference herein): any of the fibronectin based scaffold proteins or moieties described in these publications may be refolded as described herein.

In certain embodiments, a protein that may be refolded as described herein is a multivalent protein that comprises two or more fibronectin based scaffold moieties, e.g., $^{10}$Fn3 domains. For example, a multivalent fusion protein may comprise 2, 3 or more fibronectin based scaffold moieties, e.g., $^{10}$Fn3 domains, that are covalently associated. In exemplary embodiments, the fusion protein is a bispecific or dimeric protein comprising two $^{10}$Fn3 domains.

Fc Domains

Proteins that may be refolded as described herein include fusion proteins that comprise an Fc portion fused to a heterologous portion. In some aspects, the heterologous portion is a fibronectin based scaffold, e.g., an $^{10}$Fn3 domain, however, the heterologous portion may be any other protein.

As used herein, "Fc portion" encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination. The term "Fc moiety" or "Fc domain" as used herein refers to any of the combination of CH1, hinge, CH2, CH3 and CH4 domains. Thus, an "Fc domain" or moiety may or may not comprise a hinge.

Shown below is the sequence of a human IgG1 immunoglobulin constant region, and the relative position of each domain within the constant region are indicated based on the EU numbering format:

```
                                          (SEQ ID NO: 65)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS
```

```
HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

The core hinge sequence is underlined, and the CH1 region is italicized; the CH2 and CH3 regions are in regular text. It should be understood that the C-terminal lysine is optional. In certain embodiments, the C-terminal lysine of an IgG sequence may be removed or replaced with a non-lysine amino acid, such as alanine, to further increase the serum half-life of the Fc fusion protein.

In certain embodiments, an Fc fusion protein comprises a human hinge, CH2 and CH3 domains, and may have the following amino acid sequence:

```
                                          (SEQ ID NO: 66)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK,
``` wherein the core hinge sequence is underlined and the CH2 and CH3 regions are in regular text.

In certain embodiments, an Fc fusion protein comprises a CH2 and a CH3 region of a human IgG1 as shown below:

```
                                          (SEQ ID NO: 67)
VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQ

KSLSLSPGK.
```

It should be understood that the glycine and lysine at the end of a CH3 domain are optional.

Fc fusion proteins may also comprise an Fc domain that is at least 50%, 60%, 75%, 80%, 85%, 90%, 95%, 96%, 97%, 98%, or 99% identical to SEQ ID NOs: 65-67. An Fc fusion protein may also comprise an Fc domain having at least 50, 100, or 150 contiguous amino acids of SEQ ID NOs: 65-67. Fc fusion proteins may also comprise an Fc domain having from 50-100, 50-150, or 100-150 contiguous amino acids of any one of SEQ ID NOs: 65-67. Fc fusion proteins may comprise an Fc domain comprising any one of SEQ ID NOs: 65-67 with from 1-5, 1-10, 1-15, 1-20, or 1-25 substitutions, e.g., conservative substitutions.

The Fc domain may be a naturally occurring Fc sequence, including natural allelic or splice variants. Alternatively, an Fc domain may be a non-naturally occurring Fc domain, e.g., a hybrid domain comprising a portion of an Fc domain from two or more different Ig isotypes, for example, an IgG2/IgG4 hybrid Fc domain. In exemplary embodiments, the Fc domain is derived from a human immunoglobulin molecule. Alternatively, the Fc domain may be a humanized or deimmunized version of an Fc domain from a non-human animal, including but not limited to mouse, rat, rabbit, camel, llama, dromedary and monkey.

In certain embodiments, the Fc domain is a variant Fc sequence, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity.

For example, one may make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc substitutions therein, e.g., of the specific Fc region positions identified herein. Proteins comprising Fcs that are mutated to modify the biological activity of the Fc may be refolded as described herein. Exemplary Fc mutants are described, e.g., in WO97/34631; WO96/32478; U.S. Pat. Nos. 5,624,821; 5,648,260; 6,194,551; WO 94/29351; WO00/42072; U.S. Pat. Nos. 5,624,821; 6,277,375; 6,737,056; 6,194,551; 7,317,091; 8,101,720; PCT Patent Publications WO 00/42072; WO 01/58957; WO 02/06919; WO 04/016750; WO 04/029207; WO 04/035752; WO 04/074455; WO 04/099249; WO 04/063351; WO 05/070963; WO 05/040217; WO 05/092925; WO 06/020114; and Strohl, 2009, Current Opinion in Biotechnology 20:685-691; U.S. Pat. No. 6,277,375; Hinton et al., 2004, J. Biol. Chem. 279(8): 6213-6216; Hinton et al. 2006 Journal of Immunology 176:346-356; Dall Acqua et al. Journal of Immunology, 2002, 169:5171-5180, Dall'Acqua et al., 2006, Journal of Biological Chemistry 281:23514-23524; Yeung et al., 2010, J Immunol, 182:7663-7671; WO88/07054; WO88/07089; U.S. Pat. No. 6,277,375; WO99/051642; WO01/058957; WO2003/074679; WO2004/029207; U.S. Pat. No. 7,317,091 and WO2004/099249.

Exemplary variant Fcs are set forth as SEQ ID NOs: 68-86. In some aspects, an Fc fusion protein described herein comprises an Fc domain having at least 50, 100, or 150 contiguous amino acids of any one of SEQ ID NOs: 68-86. In other embodiments, an Fc fusion protein described herein comprises an Fc domain having from 50-100, 50-150, or 100-150 contiguous amino acids of SEQ ID NOs: 68-86. In yet other embodiments, an Fc fusion protein described herein comprises an Fc domain comprising SEQ ID NOs: 68-86 with from 1-5, 1-10, 1-15, 1-20, or 1-25 substitutions, e.g., conservative substitutions.

Fc fusion proteins may contain an immunoglobulin hinge region. The hinge region may be derived from antibodies belonging to any of the immunoglobulin classes, i.e. IgA, IgD, IgE, IgG, or IgM. In certain embodiments, the hinge region is derived from any of the IgG antibody subclasses, i.e. IgG1, IgG2, IgG3, and IgG4. In some embodiments, the hinge region may further include residues derived from the CH1 and CH2 regions that flank the core hinge sequence, as discussed further below.

In certain embodiments, a hinge contains a free cysteine residue that is capable of forming a disulfide bond with another monomer to form a dimer. The hinge sequence may naturally contain a cysteine residue, or may be engineered to contain one or more cysteine residues.

In certain embodiments, the Fc fusion proteins comprise a hinge region derived from a human IgG1. In some embodiments, the hinge region comprises the core hinge residues DKTHTCPPCPAPELLG (SEQ ID NO: 87) of IgG1, which corresponds to positions 221-236 according to EU numbering.

In certain embodiments, the hinge sequence may include substitutions that confer desirable pharmacokinetic, biophysical, and/or biological properties. Some exemplary hinge sequences include EPKSS<u>DKTHTCPPCPAPELLG</u>GPS;   (SEQ ID NO: 88)

core hinge region underlined),

EPKSS<u>DKTHTCPPCPAPELLG</u>GSS;   (SEQ ID NO: 89)

core hinge region underlined),

EPKSS<u>GSTHTCPPCPAPELLG</u>GSS;   (SEQ ID NO: 90)

core hinge region underlined),

<u>DKTHTCPPCPAPELLG</u>GPS;   (SEQ ID NO: 91)

core hinge region underlined), and

<u>DKTHTCPPCPAPELLG</u>GSS,   (SEQ ID NO: 92)

core hinge region underlined). In one embodiment, the hinge sequence is a derivative of an IgG1 hinge comprising a P122S substitution (EU numbering 238) (e.g., the Proline residue at position 122 in SEQ ID NO: 22 is substituted with serine). The P122S substitution ablates Fc effector function and is exemplified by the hinges having any one of SEQ ID NOs: 25, 26, and 28. In another embodiment, the hinge sequence is a derivative of an IgG1 hinge comprising D104G and K105S substitutions (EU numbering 221-222). The D104G and K105S substitutions remove a potential cleavage site and therefore increase the protease resistance of the fusion molecule. A hinge having D104G and K105S substitutions is exemplified in SEQ ID NO: 26. In another embodiment, the hinge sequence is a derivative of an IgG1 hinge comprising a C103S substitution (EU numbering 220). The C103S substitution prevents improper cysteine bond formation in the absence of a light chain. Hinges having a C103S substitution are exemplified by SEQ ID NOs: 24-26.

Fc fusion proteins may comprise a hinge sequence that comprises, consists essentially of, or consists of an amino acid sequence that is at least 50%, 60%, 75%, 80%, 85%, 90%, 95%, 96%, 97%, 98%, or 99% to that of any hinge described herein, e.g., a hinge having SEQ ID NOs: 88-92, or comprises, consists essentially of, or consists of an amino acid sequence of any hinge described herein, e.g., one of SEQ ID NOs: 88-92. Fc fusion proteins may comprise a hinge portion comprises at least or at most 2, 5, 10, 12, 15, 18 or 20 contiguous amino acid residues from any of SEQ ID NOs: 88-92, or a sequence comprising from 1-5, 1-10, 1-15, 1-20, 2-5, 2-10, 2-15, 2-20, 5-10, 5-15, 5-20, 10-15, 10-20, or 15-20 contiguous amino acid residues from any of SEQ ID NOs: 88-92. In exemplary embodiments, the hinge sequence comprises a cysteine residue.

In certain embodiments, an Fc fusion protein does not comprise a hinge. For example, an Fc fusion protein may comprise an Fc domain linked to a heterologous protein, e.g., in the Fc-X or X-Fc format, without comprising a hinge or a core hinge. In one example, an Fc fusion protein does not comprise the sequence EPKSSDKTHTCPPCP (SEQ ID NO: 93) or a variant thereof.

In certain embodiments, an Fc fusion protein does not comprise a linker. For example, an Fc fusion protein may comprise an Fc domain that is linked directly to a heterologous protein, e.g., a $^{10}$Fn3 protein without an intervening sequence. In certain embodiments, there may be 1, 2, 3, 4 or 5 amino acids (e.g., from 1-5 or 1-10 amino acids) between the Fc domain and the heterologous protein. Such Fc fusion proteins may be X-Fc (the heterologous protein is linked at the N-terminus of the Fc) or Fc-X (the heterologous protein is linked at the C-terminus of the Fc) fusion proteins, wherein X is the heterologous protein, and wherein X and Fc are directly linked to each other.

In certain embodiments, an Fc fusion protein comprises neither a hinge nor a linker.

In certain embodiments, an Fc fusion protein is a dimer, wherein each monomer comprises a fusion protein (a homodimer). In certain embodiments, an Fc fusion protein is a heterodimer comprising, e.g., a monomer that comprises an Fc fusion protein and a monomer that comprises an Fc that is not linked to another moiety. The Fc portion of a monomer may comprise one or more amino acid modifications (or mutations) relative to a wild type Fc that favor dimer, e.g., heterodimer, formation with another Fc. For example, an Fc of a dimer may comprise a "hole" and the other Fc of the dimer may comprise a "bump" or "knob," as described, e.g., in WO96/027011; U.S. Pat. Nos. 5,731,168 and 5,821,333. Other modifications, such as electrostatic modifications may be used to enhance dimer formation. Exemplary modifications are described, e.g., in WO2007/110205; WO2009/089004 and WO2010/129304. Such changes are particularly useful for enhancing the association of two heterologous monomers to form a dimer, such as a dimer that comprises a monomer comprising an Fc fusion protein and a monomer comprising an Fc that is different from the Fc fusion protein, e.g., by the lack of a heterologous protein.

In certain embodiments, an Fc fusion protein comprises a monomer comprising the structure X-Fc and a monomer comprising the structure Fc-X (or Fc-Y). An Fc fusion protein may also comprise two monomers, each comprising the structure X-Fc-X (a "quad" structure), as used, e.g., in Examples 1-3. An Fc fusion protein may also comprise two monomers, each comprising the structure X-Fc-Y, or one monomer comprising the structure X-Fc-Y and a monomer comprising the structure Y-Fc-X. Each monomer may optionally comprise a linker and optionally comprise a hinge.

An Fc fusion protein may comprise a single chain Fc (scFc), wherein the first and the second Fc domain (or the first and the second hinge-Fc domains) are linked through a linker. In one embodiment, a scFc comprises in N- to C-terminal order a first CH2 domain, which first CH2 domain is linked to a first CH3 domain, which CH3 domain is linked to an Fc linker, which Fc linker is linked the a second CH2 domain, which second CH2 domain is linked to a second CH3 domain, wherein the first and the second CH2 and CH3 domains associate to form a dimeric Fc. An scFc may comprise in N- to C-terminal order a first hinge, which first hinge is linked to a first CH2 domain, which first CH2 domain is linked to a first CH3 domain, which first CH3 domain is linked to an Fc linker, which Fc linker is linked to a second hinge, which second hinge is linked to a second CH2 domain, which second CH2 domain is linked to a second CH3 domain, wherein the first and the second hinges, CH2 domains and CH3 domains associate to form a dimeric Fc. scFcs are described, e.g., in WO2008/131242, WO2008/143954 and WO2008/012543.

Exemplary Linkers for Connecting a Heterologous Protein to an Fc Moiety

Any linker may be used for covalently linking a heterologous protein, e.g., a fibronectin based scaffold moiety, to an Fc moiety, provided that the linker allows the fusion protein comprising the heterologous protein to properly fold and be biologically active. For example, the fusion protein should be able to bind efficiently to its target and may have a long half-life in serum relative to the heterologous protein that is not linked to an Fc. A linker is also preferably essentially not immunogenic and not reactive with other proteins (i.e., chemically inert).

A linker may be from 1-6, 1-10, 1-15, 1-20, 1-25, 1-30, 1-35, 1-40, 1-45, 1-50, 5-10, 5-15, 5-15, 5-20, 5-25, 5-30, 5-35, 5-40, 5-45, or 5-50 amino acids long.

Exemplary linkers may comprise, consist of, or consist essentially of GS linkers, e.g., $(GS)_1$, $(GS)_2$, $(GS)_3$, $(GS)_4$, $(GS)_5$, $(GS)_6$, $(GS)_7$, $(GS)_8$, $(GS)_9$ or $(GS)_{10}$. Linkers may also comprise, consist of, or consist essentially of $G_4S$ linkers, e.g., $(G_4S)_1$, $(G_4S)_2$, $(G_4S)_3$, $(G_4S)_4$ or $(G_4S)_5$. Additional exemplary linkers are provided in WO2012/142515.

Exemplary Fc Fusion Proteins that May be Refolded

Fusion proteins comprising a heterologous moiety X, e.g., $^{10}$Fn3, and an Fc moiety are collectively referred to herein as X/Fc fusions regardless of whether they contain a linker or a hinge and regardless of orientation (the "/" indicates that it covers both orientations, i.e., where the Fc is N-terminal or where the Fc is C-terminal to X).

In certain embodiments, an Fc is linked directly to X, i.e., without one or more intervening amino acid (e.g., without a linker). In certain embodiment, an Fc is linked indirectly to X, i.e., with one or more intervening amino acids, e.g., a linker.

Exemplary fusion proteins are as follows, and as shown in the N- to C-terminal order:

X-hinge-CH2-CH3; X-linker-hinge-CH2-CH3; X—CH2-CH3; X-linker-CH2-CH3; hinge-CH2-CH3-X; hinge-CH2-CH3-linker-X; CH2-CH3-Fc; CH2-CH3-linker-X, wherein X is a heterologous protein relative to the Fc portion. In either orientation, the X/Fc fusion proteins described herein may further contain an N-terminal methionine and/or a leader sequence (e.g., for expression in mammalian cells).

In certain embodiments, a fusion protein comprises (i) a fibronectin based scaffold moiety comprising an amino acid sequence that is at least about 70%, 75%, 80%, 85%, 90%, 95%, 97%, 98%, or 99% identical to any one of SEQ ID NOs: 1-29; and (ii) an Fc moiety, e.g., comprising an amino acid sequence that is at least about 70%, 75%, 80%, 85%, 90%, 95%, 97%, 98%, or 99% identical to SEQ ID NO: 65-86, wherein the fusion protein binds specifically to a target (e.g., with a $K_d$ of less than 500 nM, 100 nM, 50 nM, 10 nM, 5 nM, 1 nM, 500 pM, 100 pM or less) that is not bound by a wild-type fibronectin based scaffold moiety (e.g., SEQ ID NOs: 1-8, 10, 12, 14 or 16). In certain embodiments, a fusion protein comprises (i) a fibronectin based scaffold moiety comprising an amino acid sequence that is at least about 70%, 75%, 80%, 85%, 90%, 95%, 97%, 98%, or 99% identical to any one of SEQ ID NOs: 1-29; (ii) an Fc moiety, e.g., comprising an amino acid sequence that is at least about 70%, 75%, 80%, 85%, 90%, 95%, 97%, 98%, or 99% identical to SEQ ID NO: 65-86; and (iii) a linker that covalently links the fibronectin based scaffold moiety to the Fc moiety, wherein the fusion protein binds specifically to a target (e.g., with a $K_d$ of less than 500 nM, 100 nM, 50 nM, 10 nM, 5 nM, 1 nM, 500 pM, 100 pM or less) that is not bound by a wild-type fibronectin based scaffold moiety (e.g., SEQ ID NOs: 1-8, 10, 12, 14 or 16). In certain embodiments, a fusion protein comprises (i) a fibronectin based scaffold moiety comprising an amino acid sequence that is at least about 70%, 75%, 80%, 85%, 90%, 95%, 97%, 98%, or 99% identical to any one of SEQ ID NOs: 1-29, (ii) an Fc moiety, e.g., comprising an amino acid sequence that is at least about 70%, 75%, 80%, 85%, 90%, 95%, 97%, 98%, or 99% identical to SEQ ID NO: 65-86; and (iii) a linker that covalently links the fibronectin based scaffold moiety to the Fc moiety, wherein the linker comprises 1-10 amino acids, such as 6 amino acids, and wherein the fusion protein binds specifically to a target (e.g., with a $K_d$ of less than 500 nM, 100 nM, 50 nM, 10 nM, 5 nM, 1 nM, 500 pM, 100 pM or less) that is not bound by a wild-type fibronectin based scaffold moiety (e.g., SEQ ID NOs: 1-8, 10, 12, 14 or 16). Exemplary fibronectin based scaffold moieties linked to an Fc are disclosed in WO2012/142515.

Also provided herein are protein compositions, e.g., compositions comprising one or more protein in one of the solutions or buffers described herein. For example, provided herein are compositions comprising a protein comprising at least two cysteines (wherein, e.g., the protein is a dimer comprising one cysteine on each dimer) that form a disulfide bond under appropriate conditions, and water, wherein the composition does not comprise a significant amount of buffer or a denaturing agent and optionally does not comprise a reducing agent. Also provided herein are compositions comprising a suspension of denatured proteins, wherein at least some proteins comprise at least two cysteines that form a disulfide bond under appropriate conditions, and wherein the composition does not comprise a buffer or a denaturing agent and optionally does not comprise a reducing agent. Further provided herein are compositions comprising a protein comprising at least two cysteines that form a disulfide bond under appropriate conditions, and a solubilization buffer having a pH in the range of pH 10 to 13, wherein the composition does not comprise a denaturing agent and optionally does not comprise a reducing agent. Also provided are compositions comprising a protein comprising at least two cysteines that form a disulfide bond under appropriate conditions, and a refold buffer having a pH in the range of pH 9 to 11 and an oxidizing agent, wherein the composition does not comprise a reducing agent other than a reducing agent that part of an oxidizing agent that is present in the composition. The protein concentration in any of these compositions may be at least 20 mg/ml, 15 mg/ml, 10 mg/ml, 5 mg/ml or 1 mg/ml. The compositions may comprise at least 70%, 80%, 90%, 95%, 97%, 98% or 99% of the protein of interest, e.g., a fibronectin based scaffold moiety linked to an Fc, relative to the total amount (e.g., in mg/ml) of protein in the composition. In the composition comprising refold buffer, refolded protein may constitute at least 70%, 80%, 90%, 95%, 97%, 98% or 99% of the protein in the sample.

Protein Synthesis

Proteins that can be refolded as described herein may be synthesized according to any method known in the art. Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Purified proteins may be prepared by culturing suitable host/vector systems to express the recombinant proteins. Expressed proteins, e.g., fibronectin based scaffold proteins, may then be purified from culture media or cell extracts.

Proteins may be synthesized chemically, enzymatically or recombinantly. Proteins may also be produced using cell-free translation systems. For such purposes the nucleic acids encoding the fusion protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system). For chemical synthesis, see, e.g., the methods described in Solid Phase Peptide Synthesis, 2nd ed., 1984, The Pierce Chemical Co., Rockford, Ill.).

Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 Jan. 21; 100(2):438-42; Sinclair et al. Protein Expr Purif. 2002 October; 26(1):96-105; Connell N D. Curr Opin Biotechnol. 2001 October; 12(5):446-9; Makrides et al. Microbiol Rev. 1996 September; 60(3):512-38; and Sharp et al. Yeast. 1991 October; 7(7):657-78.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from prokaryotic, mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The proteins may comprise a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence may be substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO90/13646. In mammalian cell expression, mammalian signal sequences as well as viral secretory leaders, for example, the herpes simplex gD signal, are available. The DNA for such precursor regions may be ligated in reading frame to DNA encoding the protein.

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the fusion protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the protein.

The recombinant DNA can also include any type of protein tag sequence that may be useful for purifying the fusion proteins. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct may be introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Expression in bacterial cells may be conducted essentially as follows or with certain variations therein. DNA encoding a protein of interest, e.g., a $^{10}$Fn3/Fc protein, is inserted into the pET9d (EMD Bioscience, San Diego, Calif.) vector and are expressed in *E. coli* HMS174 cells. Twenty ml of an inoculum culture (generated from a single plated colony) is used to inoculate 1 liter of LB medium containing 50 μg/ml carbenicillin and 34 μg/ml chloromphenicol. The culture is grown at 37° C. until $A_{600}$ 0.6-1.0. After induction with 1 mM isopropyl-β-thiogalactoside (IPTG) the culture is grown for 4 hours at 30° C. and is harvested by centrifugation for 30 minutes at ≥10,000 g at 4° C. Cell pellets are frozen at −80° C. The cell pellet is resuspended in 25 ml of lysis buffer (20 mM NaH$_2$PO$_4$, 0.5 M NaCl, 1× Complete Protease Inhibitor Cocktail-EDTA free (Roche), 1 mM PMSF, pH 7.4) using an Ultra-turrax homogenizer (IKA works) on ice. Cell lysis is achieved by high pressure homogenization (≥18,000 psi) using a Model M-110S MICROFLUIDIZER® (Microfluidics). The insoluble fraction is separated by centrifugation for 30 minutes at 23,300 g at 4° C. The insoluble pellet recovered from centrifugation of the lysate is washed with 20 mM sodiumphosphate/500 mM NaCl, pH7.4. The pellet may optionally be further washed with water, and suspended in a suspension solution as further described herein. Other methods are described in WO2012/142515.

Proteins may be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, proteins may be exchanged into different buffers and/or concentrated by any of a variety of methods known to the art, including, but not limited to, filtration and dialysis. Methods for expressing fusion proteins in *E. coli* are also provided in WO2012/142515.

The purified protein may be 85%, 95%, 98% or 99% pure. Regardless of the exact numerical value of the purity, the protein may be sufficiently pure for use as a pharmaceutical product.

Exemplary Uses

In one aspect, the application provides proteins, e.g., fusion proteins, comprising a fibronectin based scaffold moiety, useful in the treatment of disorders. The diseases or disorders that may be treated will be dictated by the binding specificity of the fibronectin based scaffold moiety. As described herein, fibronectin based scaffold moieties may be designed to bind to any target of interest. Exemplary targets include, for example, TNF-alpha, VEGFR2, PCSK9, IL-23, EGFR and IGF1R. Merely as an example, fibronectin based scaffold moieties that bind to TNF-alpha may be used to treat autoimmune disorders such as rheumatoid arthritis, inflammatory bowel disease, psoriasis, and asthma. Fusion proteins described herein may also be used for treating cancer.

The application also provides methods for administering proteins to a subject. In some embodiments, the subject is a human. In some embodiments, the proteins are pharmaceutically acceptable to a mammal, in particular a human. A "pharmaceutically acceptable" composition refers to a composition that is administered to an animal without significant adverse medical consequences. Examples of pharmaceutically acceptable compositions include compositions, e.g., comprising fibronecting based scaffold moiety, that are essentially endotoxin or pyrogen free or have very low endotoxin or pyrogen levels.

SEQUENCES

WT $^{10}$Fn3 Domain:
VSDVPRDLEVVAATPTSLLISWDAPAVTVRYYRITYGETGGNSPVQEFTV
PGSKSTATISGLKPGVDYTITVYAVTGRGDSPASSKPISINYRTEIDKPS
Q (SEQ ID NO: 1)

$^{10}$Fn3 Domain of SEQ ID NO: 1 (with D97E)
VSDVPRDLEVVAATPTSLLISWDAPAVTVRYYRITYGETGGNSPVQEFTV
PGSKSTATISGLKPGVDYTITVYAVTGRGDSPASSKPISINYRTEIEKPS
Q (SEQ ID NO: 2)

WT $^{10}$Fn3 Domain Core Sequence version 1:
LEVVAATPTSLLISWDAPAVTVRYYRITYGETGGNSPVQEFTVPGSKSTA
TISGLKPGVDYTITVYAVTGRGDSPASSKPISINY (SEQ ID NO: 3)

WT $^{10}$Fn3 Domain Core Sequence version 2:
EVVAATPTSLLISWDAPAVTVRYYRITYGETGGNSPVQEFTVPGSKSTAT
ISGLKPGVDYTITVYAVTGRGDSPASSKPISINYRT (SEQ ID NO: 4)

WT $^{10}$Fn3 Domain Core Sequence version 3:
VSDVPRDLEVVAATPTSLLISWDAPAVTVRYYRITYGETGGNSPVQEFTV
PGSKSTATISGLKPGVDYTITVYAVTGRGDSPASSKPISINYRT (SEQ ID NO: 5)

WT $^{10}$Fn3 Domain Core Sequence version 4:
VSDVPRDLEVVAATPTSLLISWDAPAVTVRYYRITYGETGGNSPVQEFTV
PGSKSTATISGLKPGVDYTITVYAVTGRGDSPASSKPISINYRTE (SEQ ID NO: 6)

WT $^{10}$Fn3 Domain Core Sequence version 5:
VSDVPRDLEVVAATPTSLLISWDAPAVTVRYYRITYGETGGNSPVQEFTV
PGSKSTATISGLKPGVDYTITVYAVTGRGDSPASSKPISINYRTEI
(SEQ ID NO: 7)

WT $^{10}$Fn3 Domain Core Sequence version 6:
VSDVPRDLEVVAATPTSLLISWDAPAVTVRYYRITYGETGGNSPVQEFTV
PGSKSTATISGLKPGVDYTITVYAVTGRGDSPASSKPISINYRTEID
(SEQ ID NO: 8)

$^{10}$Fn3 Domain Core Sequence version 7 (version 6 with D97E):
VSDVPRDLEVVAATPTSLLISWDAPAVTVRYYRITYGETGGNSPVQEFTV
PGSKSTATISGLKPGVDYTITVYAVTGRGDSPASSKPISINYRTEIE
(SEQ ID NO: 9)

WT $^{10}$Fn3 Domain Core Sequence version 8:
VSDVPRDLEVVAATPTSLLISWDAPAVTVRYYRITYGETGGNSPVQEFTV
PGSKSTATISGLKPGVDYTITVYAVTGRGDSPASSKPISINYRTEIDK
(SEQ ID NO: 10)

$^{10}$Fn3 Domain Core Sequence version 9 (version 8 with D97E):
VSDVPRDLEVVAATPTSLLISWDAPAVTVRYYRITYGETGGNSPVQEFTV
PGSKSTATISGLKPGVDYTITVYAVTGRGDSPASSKPISINYRTEIEK
(SEQ ID NO: 11)

WT $^{10}$Fn3 Domain Core Sequence version 10:
VSDVPRDLEVVAATPTSLLISWDAPAVTVRYYRITYGETGGNSPVQEFTV
PGSKSTATISGLKPGVDYTITVYAVTGRGDSPASSKPISINYRTEIDKP
(SEQ ID NO: 12)

$^{10}$Fn3 Domain Core Sequence version 11 (version 10 with D97E):
VSDVPRDLEVVAATPTSLLISWDAPAVTVRYYRITYGETGGNSPVQEFTV
PGSKSTATISGLKPGVDYTITVYAVTGRGDSPASSKPISINYRTEIEKP
(SEQ ID NO: 13)

WT $^{10}$Fn3 Domain Core Sequence version 12:
VSDVPRDLEVVAATPTSLLISWDAPAVTVRYYRITYGETGGNSPVQEFTV
PGSKSTATISGLKPGVDYTITVYAVTGRGDSPASSKPISINYRTEIDKPS
(SEQ ID NO: 14)

$^{10}$Fn3 Domain Core Sequence version 13 (version 12 with D97E):
VSDVPRDLEVVAATPTSLLISWDAPAVTVRYYRITYGETGGNSPVQEFTV
PGSKSTATISGLKPGVDYTITVYAVTGRGDSPASSKPISINYRTEIEKPS
(SEQ ID NO: 15)

WT $^{10}$Fn3 Domain with D80E Substitution
VSDVPRDLEVVAATPTSLLISWDAPAVTVRYYRITYGETGGNSPVQEFTV
PGSKSTATISGLKPGVDYTITVYAVTGRGESPASSKPISINYRTEIDKPS
Q (SEQ ID NO: 16)

Degenerate WT $^{10}$Fn3 Domain Core Sequence:
VSDVPRDLEVVAA(X)$_u$LLISW(X)$_v$YRITY(X)$_w$FTV(X)$_x$ATISGL
(X)$_y$YTITVYA(X)$_z$ISINYRT (SEQ ID NO: 17)

VSDVPRDLEVVAA(X)$_u$LLISW(X)$_v$YRITY(X)$_w$FTV(X)$_x$ATISGL
(X)$_y$YTITVYA(X)$_z$ISINYRTE (SEQ ID NO: 18)

VSDVPRDLEVVAA(X)$_u$LLISW(X)$_v$YRITY(X)$_w$FTV(X)$_x$ATISGL
(X)$_y$YTITVYA(X)$_z$ISINYRTEI (SEQ ID NO: 19)

VSDVPRDLEVVAA(X)$_u$LLISW(X)$_v$YRITY(X)$_w$FTV(X)$_x$ATISGL
(X)$_y$YTITVYA(X)$_z$ISINYRTEID (SEQ ID NO: 20)

VSDVPRDLEVVAA(X)$_u$LLISW(X)$_v$YRITY(X)$_w$FTV(X)$_x$ATISGL
(X)$_y$YTITVYA(X)$_z$ISINYRTEIE (SEQ ID NO: 21)

SEQUENCES

VSDVPRDLEVVAA(X)$_u$LLISW(X)$_v$YRITY(X)$_w$FTV(X)$_x$ATISGL(X)$_y$YTITVYA(X)$_z$ISINYRTEIDK (SEQ ID NO: 22)

VSDVPRDLEVVAA$(X)_u$LLISW$(X)_v$YRITY$(X)_w$FTV$(X)_x$ATISGL
$(X)_y$YTITVYA$(X)_z$ISINYRTEIEK (SEQ ID NO: 23)

VSDVPRDLEVVAA$(X)_u$LLISW$(X)_v$YRITY$(X)_w$FTV$(X)_x$ATISGL
$(X)_y$YTITVYA$(X)_z$ISINYRTEIDKP (SEQ ID NO: 24)

VSDVPRDLEVVAA$(X)_u$LLISW$(X)_v$YRITY$(X)_w$FTV$(X)_x$ATISGL
$(X)_y$YTITVYA$(X)_z$ISINYRTEIEKP (SEQ ID NO: 25)

VSDVPRDLEVVAA$(X)_u$LLISW$(X)_v$YRITY$(X)_w$FTV$(X)_x$ATISGL
$(X)_y$YTITVYA$(X)_z$ISINYRTEIDKPS (SEQ ID NO: 26)

VSDVPRDLEVVAA$(X)_u$LLISW$(X)_v$YRITY$(X)_w$FTV$(X)_x$ATISGL
$(X)_y$YTITVYA$(X)_z$ISINYRTEIEKPS (SEQ ID NO: 27)

VSDVPRDLEVVAA$(X)_u$LLISW$(X)_v$YRITY$(X)_w$FTV$(X)_x$ATISGL
$(X)_y$YTITVYA$(X)_z$ISINYRTEIDKPSQ (SEQ ID NO: 28)

VSDVPRDLEVVAA$(X)_u$LLISW$(X)_v$YRITY$(X)_w$FTV$(X)_x$ATISGL
$(X)_y$YTITVYA$(X)_z$ISINYRTEIEKPSQ (SEQ ID NO: 29)

MGVSDVPRDL (SEQ ID NO: 30)

GVSDVPRDL (SEQ ID NO: 31)

$X_n$SDVPRDL (SEQ ID NO: 32)

$X_n$DVPRDL (SEQ ID NO: 33)

$X_n$VPRDL (SEQ ID NO: 34)

$X_n$PRDL (SEQ ID NO: 35)

$X_n$RDL (SEQ ID NO: 36)

$X_n$DL (SEQ ID NO: 37)

MASTSG (SEQ ID NO: 38)

EIEK (SEQ ID NO: 39)

EGSGC (SEQ ID NO: 40)

EIEKPCQ (SEQ ID NO: 41)

EIEKPSQ (SEQ ID NO: 42)

EIEKP (SEQ ID NO: 43)

EIEKPS (SEQ ID NO: 44)

EIEKPC (SEQ ID NO: 45)

HHHHHH (SEQ ID NO: 46)

EIDK (SEQ ID NO: 47)

EIDKPCQ (SEQ ID NO: 48)

EIDKPSQ (SEQ ID NO: 49)

MPAPTDLRFTNETPSSLLISWTPPRVQITGYIIRYGPVGSDGRVKEFTVP
PSVSSATITGLKPGTEYTISVIALKDNQESEPLRGRVTTGG
(FibconB; SEQ ID NO: 50)

TPSS (SEQ ID NO: 51)

TPPRVQI (SEQ ID NO: 52)

VGSDGR (SEQ ID NO: 53)

PSVS (SEQ ID NO: 54)

-continued

SEQUENCES

GLKPG (SEQ ID NO: 55)

KDNQESEP (SEQ ID NO: 56)

LDAPTDLQVTNVTDTSITVSWTPPSATITGYRITYTPSNGPGEPKELTVP
PSSTSVTITGITPGVEYVVSVYALKDNQESPPLVGTCTT (SEQ ID
NO: 57)

LPAPKNLVVSEVTEDSLRLSWTAPDAAFDSFLIQYQESEKVGEAINLTVP
GSERSYDLTGLKPGTEYTVSIYGVKGGHRSNPLSAEFTT (SEQ ID
NO: 58)

TEDS (SEQ ID NO: 59)

TAPDAAF (SEQ ID NO: 60)

SEKVGE (SEQ ID NO: 61)

GSER (SEQ ID NO: 62)

GLKPG (SEQ ID NO: 63)

KGGHRSN (SEQ ID NO: 64)

ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK (SEQ ID NO: 65)

DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK (SEQ ID NO: 66)

VFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQK
SLSLSPGK (SEQ ID NO: 67)

EPRSSDKTHTCPPCPAPEAEGAPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPSSIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK (SEQ ID NO: 68)

EPKSSDKTHTCPPCPAPEAEGAPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPSSIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK (SEQ ID NO: 69)

EPKSSDKTHTCPPCPAPEAEGAPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPSSIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPG (SEQ ID NO: 70)

EPKSCDKTHTCPPCPAPELLGGPSVFLFPPKPKDTLMISRTPEVTCVVVD
VSHEDPEVKFNWYVDGVEVHNAKTKPREEQYQSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK (SEQ ID NO: 71)

EPRSSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK (SEQ ID NO: 72)

DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK

| SEQUENCES |
|---|
| GFYPSDIAVEWESNGQPENNYKTTPPVLDSDGSFLYSKLTVDKSRWQQGN<br>VFSCSVMHEALHNHYTQKSLSLSPGK (SEQ ID NO: 73) |
| EPKSSDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLN<br>GKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK (SEQ ID NO: 74) |
| EPKSSDKTHTCPPCPAPEAEGAPSVFLFPPKPKDTLMISRTPEVTCVVVD<br>VSHEDPEVKFNWYVDGVEVHNAKTKPREEQYNSTYRVVSVLTVLHQDWLN<br>GKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK (SEQ ID NO: 75) |
| EPKSSDKTHTSPPSPAPEAEGAPSVFLFPPKPKDTLMISRTPEVTCVVVD<br>VSHEDPEVKFNWYVDGVEVHNAKTKPREEQYNSTYRVVSVLTVLHQDWLN<br>GKEYKCKVSNKALPSSIEKTISKAKGQPREPQVYTLPPSRDELTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK (SEQ ID NO: 76) |
| EPKSSDKTHTSPPSPAPEAEGAPSVFLFPPKPKDTLMISRTPEVTCVVVD<br>VSHEDPEVKFNWYVDGVEVHNAKTKPREEQYNSTYRVVSVLTVLHQDWLN<br>GKEYKCKVSNKALPSSIEKTISKAKGQPREPQVYTLPPSRDELTKNQVSL<br>TCLVKGFYPSDIAVEWESNGQPENNYKTTPPVLDSDGSFFLGSKLTVDKS<br>RWQQGNVFSCSVMHEALHNHYTQKSLSLSPGK (SEQ ID NO: 77) |
| EPKSSDKTHTSPPSPAPELLGGPSVFLFPPKPKDTLMISRTPEVTCVVVD<br>VSHEDPEVKFNWYVDGVEVHNAKTKPREEQYNSTYRVVSVLTVLHQDWLN<br>GKEYKCKVSNKALPAPIEKTISKAKGQPREPQVYTLPPSRDELTKNQVSL<br>TCLVKGFYPSDIAVEWESNGQPENNYKTTPPVLDSDGSFFLGSKLTVDKS<br>RWQQGNVFSCSVMHEALHNHYTQKSLSLSPGK (SEQ ID NO: 78) |
| ESKYGPPCPPCPAPEFLGGPSVFLFPPKPKDTLMISRTPEVTCVVVDVSQ<br>EDPEVKFNWYVDGVEVHNAKTKPREEQFNSTYRVVSVLTVLHQDWLNGKE<br>YKCKVSNKGLPSSIEKTISKAKGQPREPQVYTLPPSQEEMTKNQVSLTCL<br>VKGFYPSDIAVEWESNGQPENNYKTTPPVLDSDGSFFLYSRLTVDKSRWQ<br>EGNVFSCSVMHEALHNHYTQKSLSLSLGK (SEQ ID NO: 79) |
| EPKSSDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLN<br>GKEYKCKVSNKALPAPIEKTISKAKGQPREPQVYTLPPSQEEMTKNQVSL<br>TCLVKGFYPSDIAVEWESNGQPENNYKTTPPVLDSDGSFFLYSRLTVDKS<br>RWQEGNVFSCSVMHEALHNHYTQKSLSLSLGK (SEQ ID NO: 80) |
| EPKSSDKTHTCPPCPAPELLGGPSVFLAPPKPKDTLMISRTPEVTCVVVD<br>VSHEDPEVKFNWYVDGVEVHNAKTKPREEQYNSTYRVVSVLTVLHQDWLN<br>GKEYKCKVSNKALPSSIEKTISKAKGQPREPQVYTLPPSRDELTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK (SEQ ID NO: 81) |
| EPKSSDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLN<br>GKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKS<br>RWQQGNVFSCSVMHEALHNAYTQKSLSLSPGK (SEQ ID NO: 82) |
| EPKSSDKTHTCPPCPAPEAEGAPSVFLFPPKPKDTLMISRTPEVTCVVVD<br>VSHEDPEVKFNWYVDGVEVHNAKTKPREEQYQSTYRVVSVLTVLHQDWLN<br>GKEYKCKVSNKALPSSIEKTISKAKGQPREPQVYTLPPSRDELTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK (SEQ ID NO: 83) |
| EPKSSDKTHTSPPSPAPEAEGAPSVFLFPPKPKDTLMISRTPEVTCVVVD<br>VSHEDPEVKFNWYVDGVEVHNAKTKPREEQYNSTYRVVSVLTVLHQDWLN<br>GKEYKCKVSNKALPSSIEKTISKAKGQPREPQVYTLPPSRDELTKNQVSL<br>TCLVKGFYPSDIAVEWESNGQPENNYKTTPPVLDSDGSFALGSKLTVDKS<br>RWQQGNVFSCSVMHEALHNHYTQKSLSLSPGK (SEQ ID NO: 84) |
| EPKSSDKTHTSPPSPAPELLGGPSVFLFPPKPKDTLMISRTPEVTCVVVD<br>VSHEDPEVKFNWYVDGVEVHNAKTKPREEQYNSTYRVVSVLTVLHQDWLN<br>GKEYKCKVSNKALPAPIEKTISKAKGQPREPQVYTLPPSRDELTKNQVSL<br>TCLVKGFYPSDIAVEWESNGQPENNYKTTPPVLDSDGSFALGSKLTVDKS<br>RWQQGNVFSCSVMHEALHNHYTQKSLSLSPGK (SEQ ID NO: 85) |
| EPKSSDKTHTCPPCPAPEAGGGPSVFLFPPKPKDTLMISRTPEVTCVVVD<br>VSHEDPEVKFNWYVDGVEVHNAKTKPREEQYNSTYRVVSVLTVLHQDWLN |

| SEQUENCES |
|---|
| GKEYKCKVSNKALPASIEKTISKAKGQPREPQVYTLPPSRDELTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK (SEQ ID NO: 86) |
| DKTHTCPPCPAPELLG (SEQ ID NO: 87) |
| EPKSSDKTHTCPPCPAPELLGGPS (SEQ ID NO: 88) |
| EPKSSDKTHTCPPCPAPELLGGSS (SEQ ID NO: 89) |
| EPKSSGSTHTCPPCPAPELLGGSS (SEQ ID NO: 90) |
| DKTHTCPPCPAPELLGGPS (SEQ ID NO: 91) |
| DKTHTCPPCPAPELLGGSS (SEQ ID NO: 92) |
| EPKSSDKTHTCPPCP (SEQ ID NO: 93) |

The following representative Examples contain important additional information, exemplification and guidance which can be adapted to the practice of this invention in its various embodiments and the equivalents thereof. These examples are intended to help illustrate the invention, and are not intended to, nor should they be construed to, limit its scope.

EXAMPLES

Example 1: High-Throughput Screening of Buffer Conditions for Refolding Denatured Proteins In order to identify effective refolding conditions for $^{10}$Fn3/Fc fusion proteins produced in *E. coli*, an automated liquid handling platform was used to execute protein refolding by dilution in triplicate in 96-well plates.

The biomass of a $^{10}$Fn3/Fc protein was produced in a 10 L fermentor. The biomass was harvested and the IBs were recovered and washed by centrifugation before being frozen.

The screening study looked at protein concentration, resolubilization buffer, refold pH, temperature, aggregation suppressing excipients, and redox excipients. JMP Design of Experiments (DoE) software was used to design the screening study and analyze data. Data were gathered using a plate reader and SE-HPLC. The data suggested a resolubilization buffer around pH 8 with Guanidine and a refold buffer with Arginine to suppress aggregation, and a Glutathione redox system, around pH 10, favored formation of soluble protein. In addition, these conditions showed protein around the correct molecular weight in solution, indicating disulfide bond formation, required to form the $^{10}$Fn3/Fc homodimer.

Scale up of the dilution refold to 50 mL, 100 mL and 200 mL final refold volumes using the above-identified conditions were performed using a calibrated pump and mixing. A variable and heavy precipitation event was observed in all cases and a low recovery of protein was observed. Only around 10 to 20% of the protein was recovered in solution and found to be at the appropriate molecular weight. For a subset of the bench scale dilution refolds, a majority of the protein recovered in solution was found to be at a smaller molecular weight corresponding to $^{10}$Fn3/Fc monomer and indicating that the disulfide bonds did not form. With these data, it was determined that alternative methods of refolding $^{10}$Fn3/Fc molecules should be evaluated.

Example 2: Effect of pH on Refolding Proteins from IBs

This Example describes that the efficiency of refolding denatured Fc fusion proteins varies with the pH of the buffer used for refolding the proteins, and that refolding is more efficient at higher pH than at lower pH.

The refold efficiency of an Fc fusion protein under different conditions was analyzed using Sephadex G25 chromatography. Briefly, a column is conditioned with refold buffer, following which solubilized IBs are added to the column and the protein from the IBs is recovered by passing the same refold buffer as that used for conditioning the column over the column.

The Fc fusion protein used was a $^{10}$Fn3/Fc molecule having the following amino acid sequence:

*MGVSDVPRDLEVVAATPTSLLISWVPPSDDYGYYRITYGETGGNSPVQE*

*FTVPIGKGTATISGLKPGVDYTITVYAVEFPWPHAGYYHRPISINYRTE*

*IEPKSSGS*THTCPPCPAPELLGGSSVFLFPPKPKDTLMISRTPEVTCVV

VDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKN

QVSLTCLVKGFYPSDIAVEWESNGQPENNYKTTPPVLDSGSFFLYSKL

TVDKSRWQQGNVFSCSVMHEALHNHYTQKSLSLSPGK (SEQ ID NO: 94; the $^{10}$Fn3 sequence is shown in italics).

The $^{10}$Fn3/Fc protein was expressed in *E. coli* and the IBs were collected. The IBs were solubilized at a weight (grams):volume (ml) ratio of 1:20 in 50 mM Tris pH 8.0, 6.0 M GuHCl, 0.2 mM TCEP. The solubilization reaction was mixed until complete solubilization of IBs occurred. The solubilization reaction was then mixed with a 2× volume of 50 mM Tris, 0.4M arginine pH 10.4, and 10 ml thereof was loaded onto 2.5×10 cm Sephadex G25 columns at 150 cm/hr. The G25 Sephadex columns were conditioned with refold buffer consisting of 0.4 M Arginine and 50 mM Tris pH 8.5, 9.0 or 10.4 by loading a 10% column volume equivalent of refold buffer on the column at 150 cm/hr until stable baseline pH was achieved. Absorbance of the eluate was monitored at 280 nm and the major absorbance peak of each column was collected for further analysis.

Figure 2A:
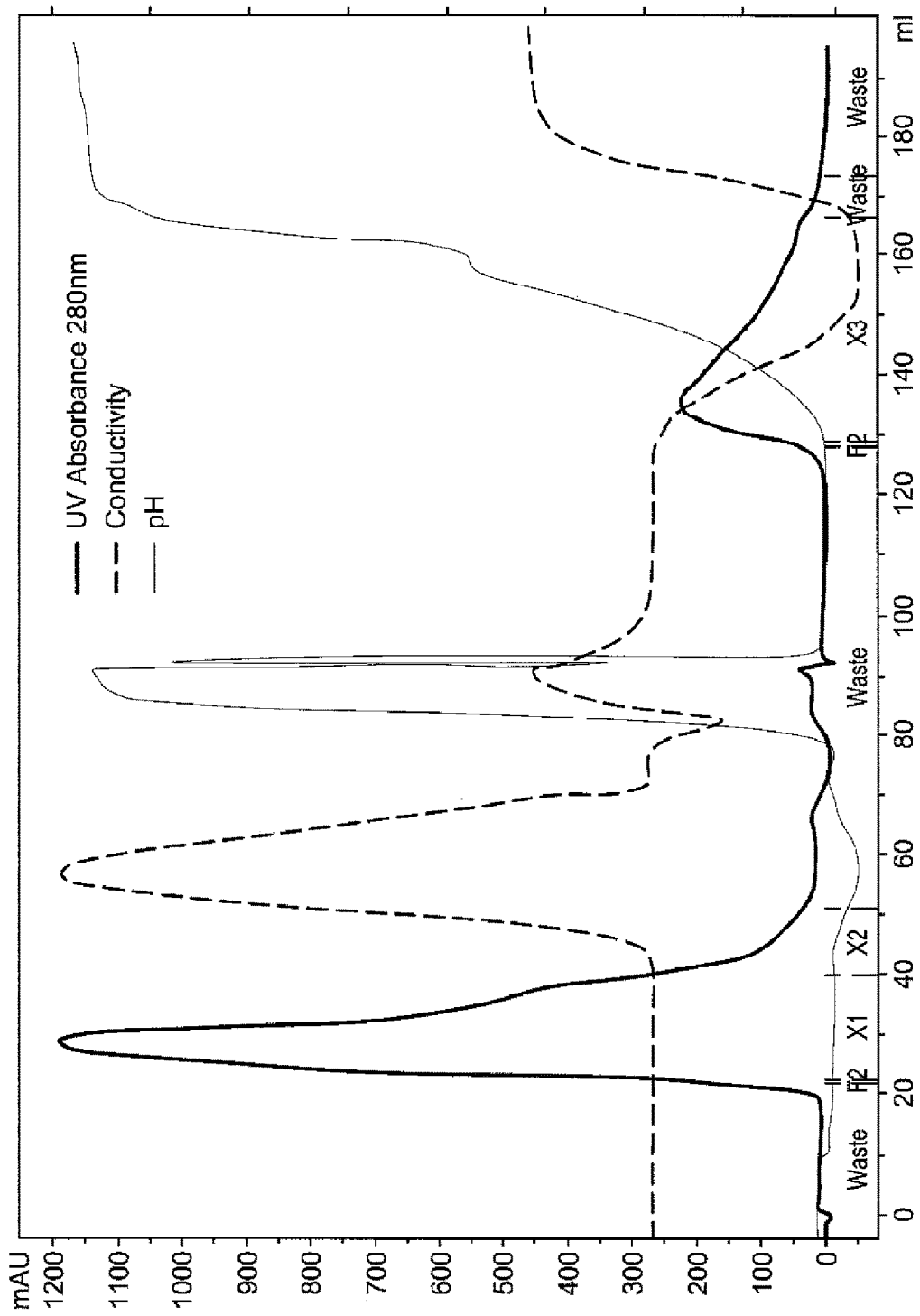
FIGS. 2A-2C show the results of the use of a G25 buffer exchange method to estimate refold efficiency.
Figure 2B:
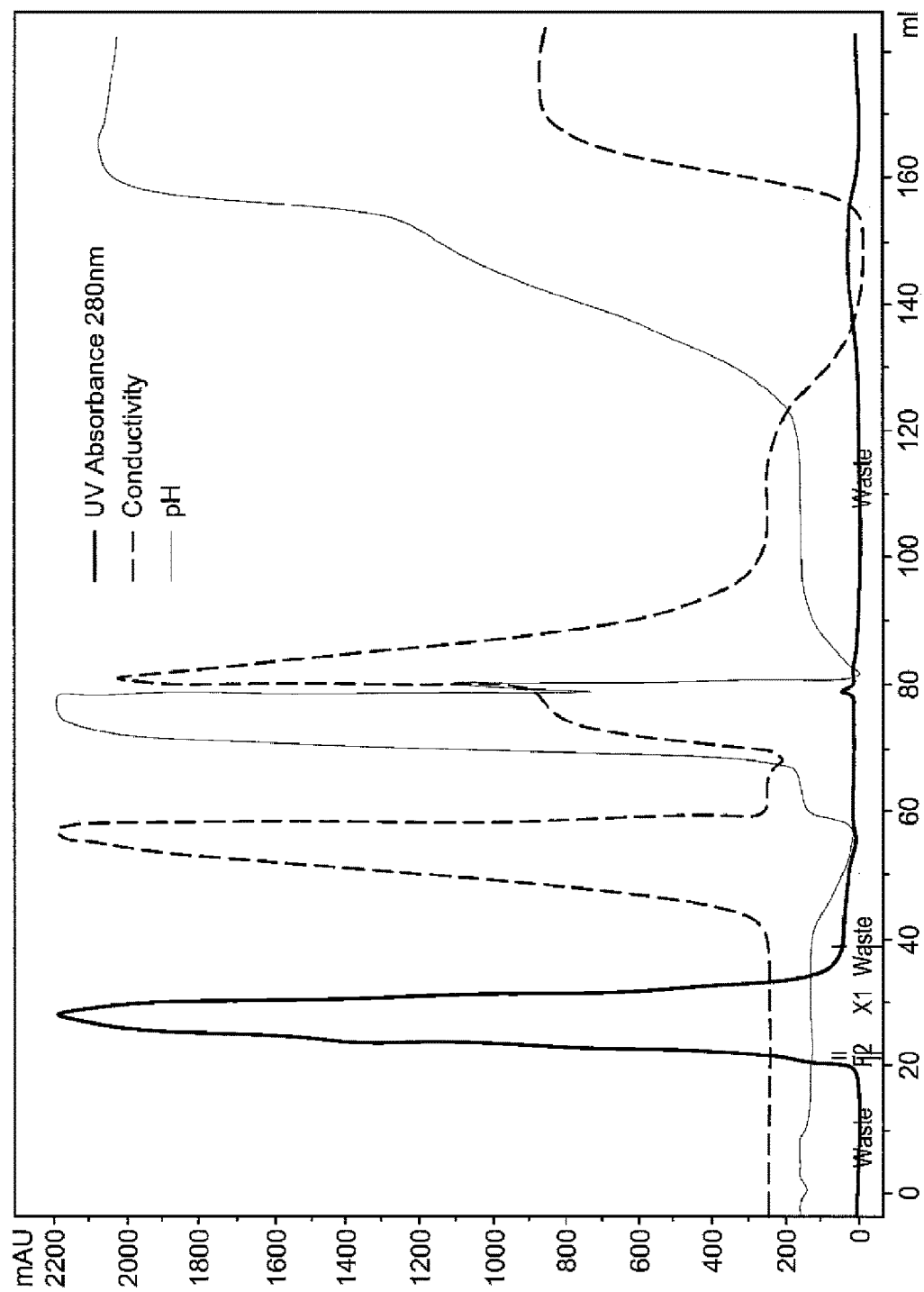
Figure 2C:
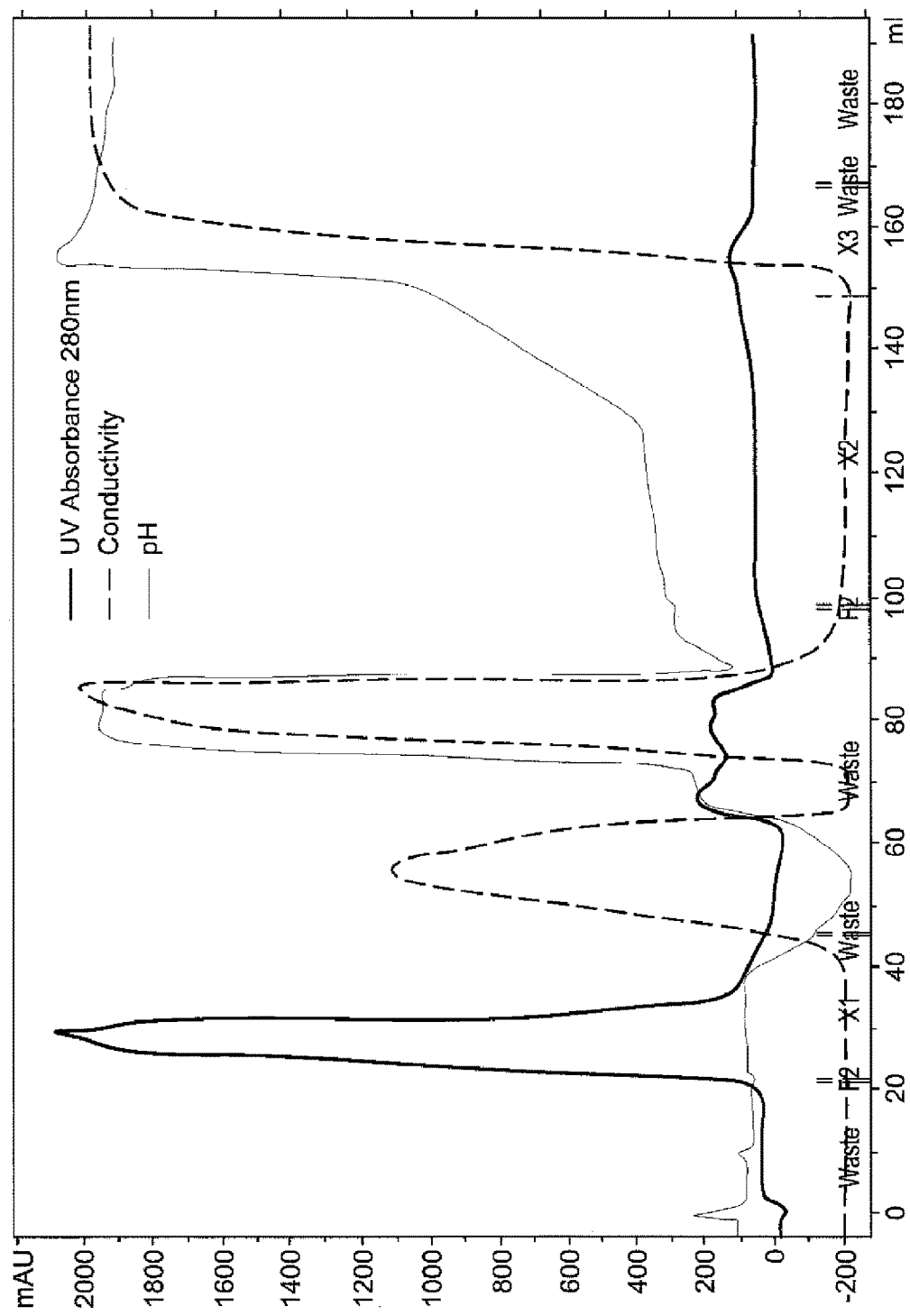

The chromatograms of the experiments conducted at pH 8.5, 9.0 and 10.4 are shown in FIGS. 2A, B and C, respectively. Aggregate and precipitated protein can be visualized in the chromatograms as peak shifts or as NaOH strip peaks. The chromatogram of the refold experiment conducted at pH 8.5 (FIG. 2A) shows a significant shift as well as a NaOH strip peak, whereas the chromatograms of the refold experiments conducted at pH 9.0 and 10.4 (FIGS. 2B and C, respectively) show good peak symmetry and no NaOH strip peak, indicating less aggregation and protein precipitation, and higher solubility of the proteins at pH 9.0 and 10.4 than at pH 8.5. As solubility is used as an indicator of proper protein folding in these experiments, the results indicate that refolding denatured protein at pH 9.0 and 10.4 is more efficient than at pH 8.5.

Efficiency of refolding at the different pH values was also analyzed with SDS PAGE. This method shows soluble aggregated protein, which is also indicative of protein misfolding. 10 μl of protein from the major absorbance peaks that were eluted from the G25 Sephadex columns described above were diluted with 20 μl of water and 10 μl LDL sample buffer, and 30 μl of diluted sample was loaded on a 10 well 4-12% Bis-Tris Gel (Novex). The gel was run at 200V for 35 minutes. The gel was rinsed with water for 10 minutes, stained overnight with thermo gelcode blue stain and destained for 3 hours prior to scanning.

Figure 3A:
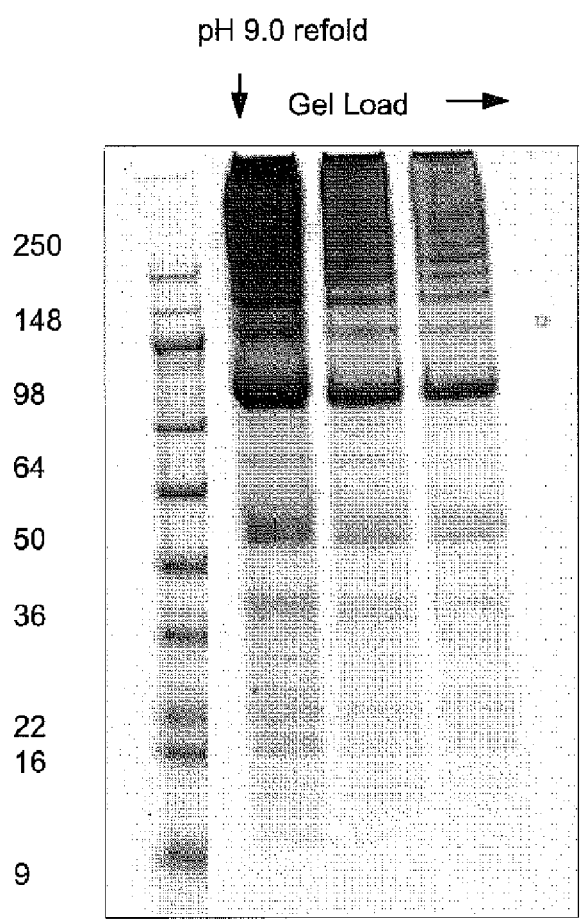
FIGS. 3A and 3B show soluble aggregate concentration visualized by SDS-PAGE. SDS PAGE analysis of G25 refolds performed at pH 9.0 (FIG. 3A) and pH 10.4 (FIG. 3B).
Figure 3B:
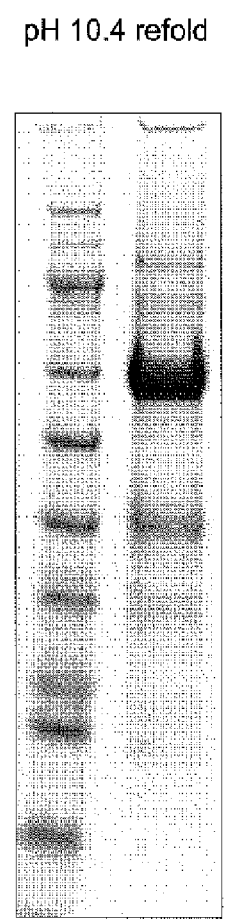

The stained gels are shown in FIGS. 3A and B. These indicate that significant soluble aggregate is present in the refold done at pH 9.0, whereas at pH 10.4, less soluble aggregate is present and more dimer is present, suggesting that refolding and dimer formation is more efficient at higher pH.

Example 3: A Reducing Agent is not Necessary During Refolding

Certain methods for refolding proteins comprising disulfide bonds use two refolding steps: a first refolding step during which a reducing agent, e.g., TCEP, is used to maintain a reduced conformation of the cysteines, to first refold the monomers; and a second refolding step during which disulfide bonds are formed, to dimerize the properly formed monomers. In this Example the necessity of including a reducing agent during a first refold step was investigated, and the results show that a reducing agent is not necessary for obtaining efficient refolding of a denatured protein.

The same experiment as that described in Example 2 was performed with the refold buffer at pH 10.4. The protein of the major absorbance peak was then incubated at room temperature for 30 minutes or 4 hours in the same buffer (i.e., in the absence of TCEP), prior to being loaded onto an SDS-PAGE gel. The gel was loaded and run and stained essentially as described in Example 2.

Figure 4A:
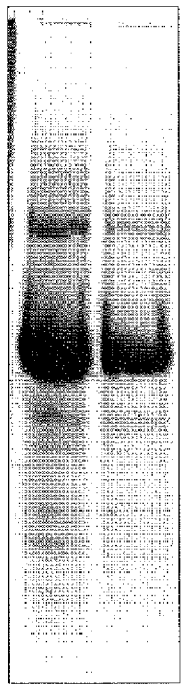
FIGS. 4A and 4B show SDS-PAGE gels of G25 refold reactions incubated for 30 minutes (FIG. 4A) or 4 hours (FIG. 4B) in the absence of TCEP prior to loading on SDS-PAGE.
Figure 4B:
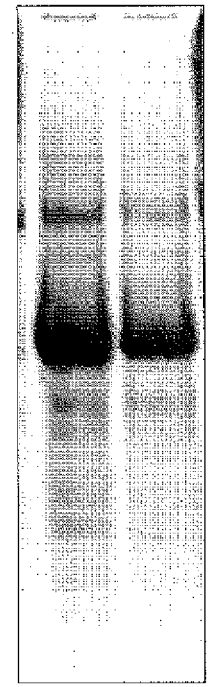

The stained SDS-PAGE gel is shown in FIGS. 4 A and B. The results show that dimer formation does not occur in the absence of TCEP even after the longer (4 hours) incubation time. This finding suggests that it is not necessary to include a reducing agent, e.g., TCEP, during the first refolding step. In addition, eliminating TCEP from the $^{10}$Fn3/Fc refolding procedures resulted in significant reduction of CH3 open loop content of $^{10}$Fn3/Fc preparations.

Example 4: The First Refolding Step Occurs Rapidly

This Example shows that refolding denatured protein during the first refolding step occurs rapidly, and therefore a long incubation time prior to the second refold (oxidizing) step is not necessary.

If proper refolding of monomer is required prior to correct dimer formation and the rate of refolding of the monomer is slow, it may be necessary to conduct the monomer refolding step (i.e., refold step 1) for a long time. The results of the G25 refold experiments described in Examples 1 and 2, however, appear to show that proper folding of $^{10}$Fn3/Fcs can be accomplished using an almost instantaneous removal of denaturant (i.e., a short refold step 1). The instant Example confirms this observation by testing different refold step 1 incubation times.

The same experiment as that described in Example 2 was performed with the refold buffer at pH 10.4. The protein of the major absorbance peak was then incubated at room temperature for 0, 1 hour or 2 hours either as eluted or after diluting it 1:1 with 50 mM Tris, 0.4M Arginine pH 10.4 refold buffer. After the incubation, Glutathione at a concentration of 1:0.2 mM oxidized:reduced was then added to samples. The reactions were then incubated for another 3 hours at room temperature. SDS-PAGE was then performed essentially as described in Example 2.

Figure 5:
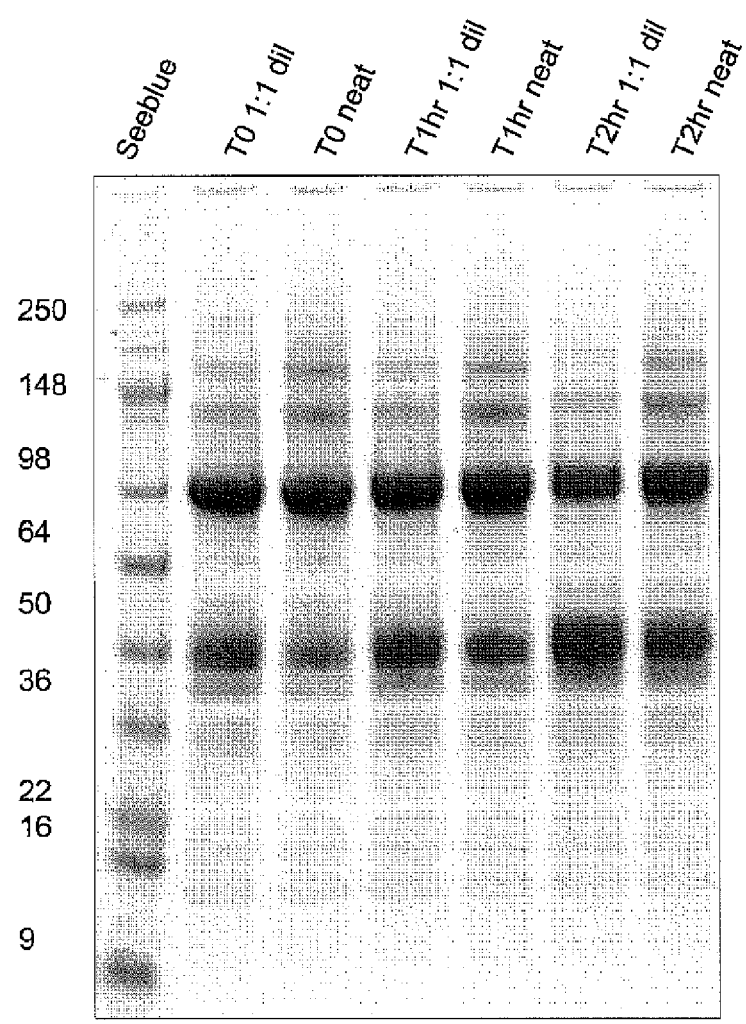
FIG. 5 shows dimer formation efficiency after 0, 1 and 2 hour refold incubation periods prior to redox addition. "Dil" refers to the lower concentration of $^{10}$Fn3/Fc relative to the concentration of the samples referred to as "neat."

The stained gels, which are shown in FIG. 5, indicate that similar levels of dimer formation occurred in all samples regardless of the incubation time of the samples (corresponding to refold step 1), suggesting that refolding occurs rapidly after the denaturing agent is removed. Although refold occurred in both the samples directly eluted from the column and those diluted 1:1 with refold buffer, dimer formation appears to be more efficient in the diluted samples.

Example 5: Solubilization of IBs at High pH in the Absence of Guanidine Hydrochloride This Example shows that IBs can be solubilized in a buffer having high pH in the absence of a denaturing agent, such as guanidine hydrochloride.

Solubilization efficiency of $^{10}$Fn3/Fc IBs in solubilization buffer with pH values from 10.4 through 12.5 was explored. IBs of the same protein as that in the previous Examples were added to a 20× volume of 50 mM Tris, 0.4M Arginine pH 10.4. Mixing was initiated, and the pH was slowly adjusted with 12M NaOH until all IBs were solubilized. The pH of the solution at solubilization was pH 12.2.

Later experiments explored reducing the pH of the solubilization using Proline and Glycine as additives. The only condition at lower pH that was successful in solubilizing IBs in a reasonable time frame was 50 mM Tris, 0.5M Arginine, 0.1M Proline pH 10.7. Solubilization took 20 minutes in this solution. Thus, at lower pH values, additives were required to fully solubilize the IBs, and the solubilization took significantly longer than at higher pH. Solubilization at pH 12.2 for 3-5 minutes was found to solubilize essentially all IBs in the reaction.

Example 6: Characterization of the Protein Folded State at Different pHs

This Example shows that at least partial tertiary structure of a $^{10}$Fn3/Fc protein is maintained during solubilization of IBs at high pH, but not in a 6M Guanidine solution.

To determine whether a $^{10}$Fn3/Fc protein retains a secondary and tertiary structure during solubilization at high pH, Far and Near UV Circular Dichroism (CD) was used.

A $^{10}$Fn3/Fc protein comprising a human IgG1 Fc linked to the N-terminus of a $^{10}$Fn3 moiety binding to a different target from that bound by the molecule used in Examples 2-5 was expressed in E. coli and IBs were isolated. The Fc has the following amino acid sequence:

(SEQ ID NO: 95)
MGDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVFSCSVMHEALHNHYTQKSLSLSP.

As Arginine is not compatible with CD, a solubilization buffer different from that in Example 5 was used. A purified high concentration sample of $^{10}$Fn3/Fc protein was diluted into the following buffers at a final concentration of 1 mg/ml: 50 mM phosphate pH 7.2; 50 mM Tris pH 8.0; 50 mM carbonate pH 10.2; 50 mM phosphate pH 12.2; 50 mM Tris pH 8.0+6M GuHCl. A sample of protein diluted into 50 mM phosphate pH 12.2 was adjusted back to pH 7.5 using hydrochloric acid. The samples were subjected to Far and Near UV CD.

Figure 6A:
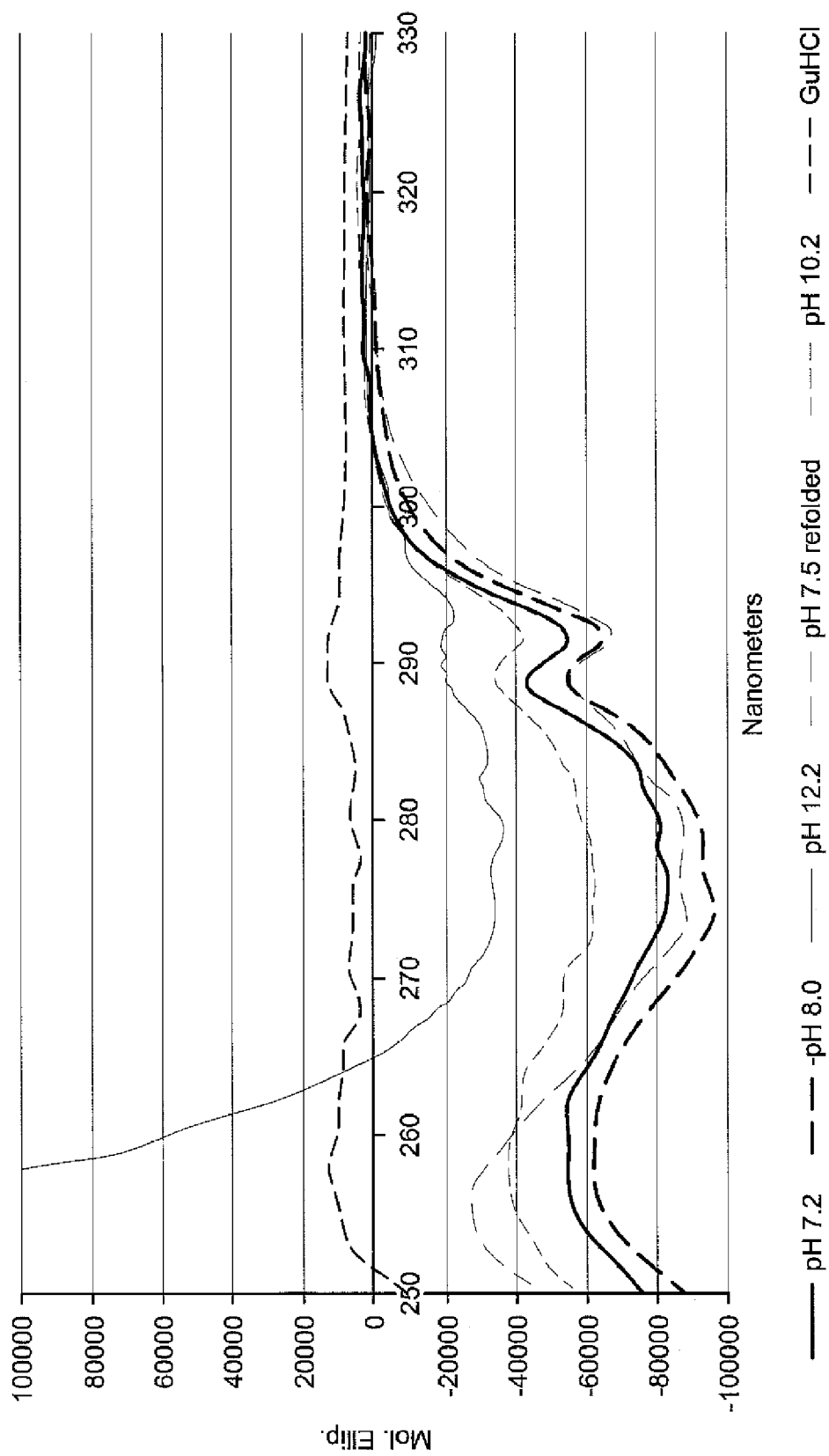
FIGS. 6A and 6B show Near and Far UV Circular Dichroism (CD) of $^{10}$Fn3/Fc in different conditions.
Figure 6B:
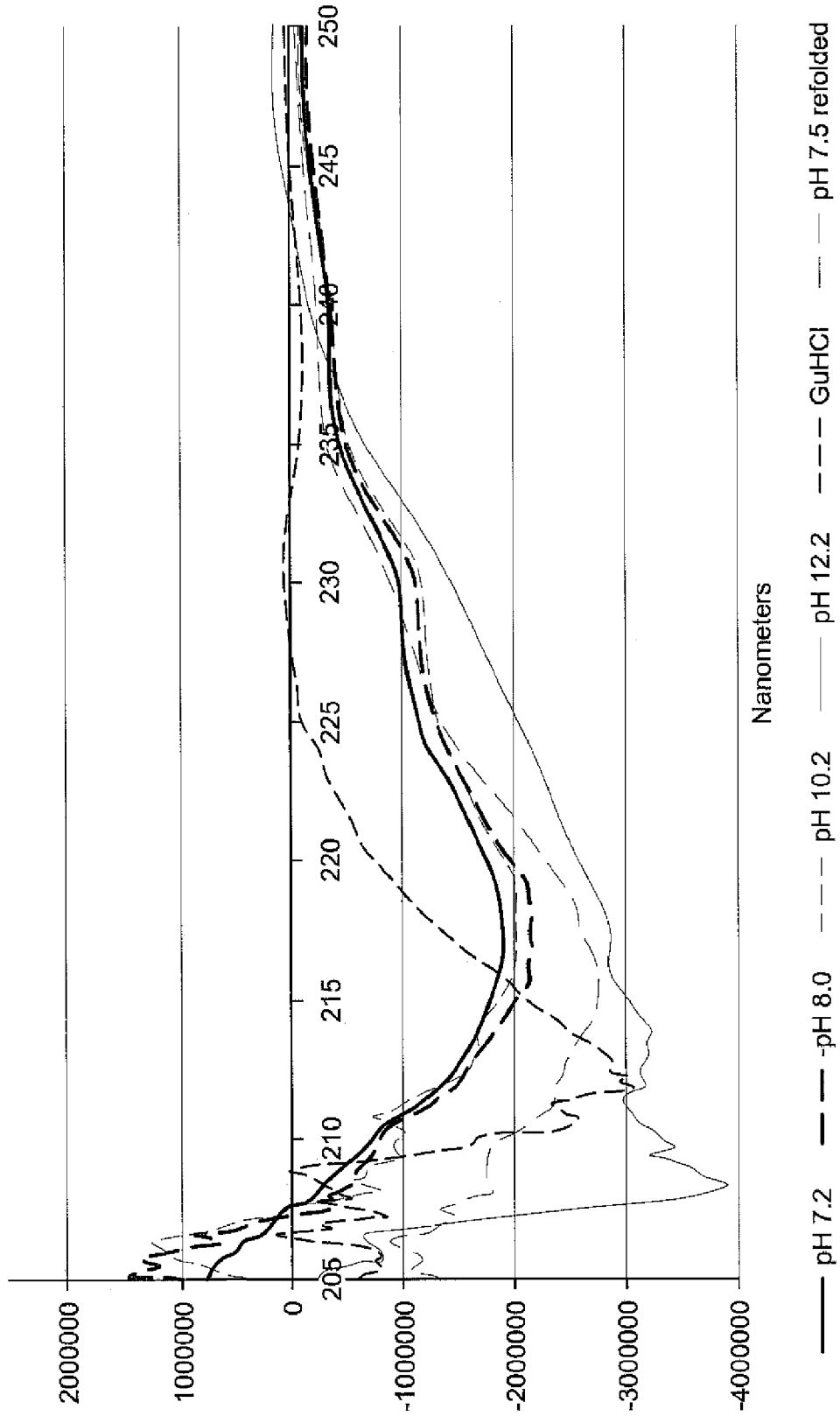

The results, which are shown in FIGS. 6A and B, indicate that at high pH some tertiary structure is maintained while with 6M Guanidine all the secondary and tertiary structure is lost (see FIGS. 6A and B). At pH 10.4 most of the secondary and tertiary structure is maintained. Bringing the protein from pH 12.2 to pH 7.5 showed partial refolding of the molecule. Thus, the results indicate that a denatured protein that is solubilized in a solubilizing buffer at high pH but in the absence of a denaturing agent maintains some tertiary structure, and that this may facilitate refolding of the protein relative to a solubilization/refolding method using a denaturing agent, such as guanidine hydrochloride.

Example 7: High pH IB Solubilization and Refold of $^{10}$Fn3/Fc Proteins

This Example describes a method for solubilizing and refolding denatured proteins in the absence of a denaturing agent. The method was used to solubilize and refold several different $^{10}$Fn3/Fc proteins, some of which were in the $^{10}$Fn3-Fc format and others in the Fc-$^{10}$Fn3 format.

All steps were performed at room temperature.

15 grams of IBs were suspended in 30 mls of Milli Q water. The suspension was mixed until a uniform appearance was observed and then placed aside.

Solubilization buffer was prepared by adding 1.398 ml of 12.5M NaOH to 300 mls of 50 mM Tris, 0.4M Arginine pH 10.4. Final pH after addition was 12.2.

Refold buffer was prepared as follows. A total of 0.915 g of oxidized glutathione and 0.0915 g of reduced glutathione was added to 900 ml of 50 mM Tris pH, 0.4 M Arginine pH 10.4. A total of 1.701 ml of 12.0M HCl was spiked into the refold buffer+glutathione.

Table 1 provides the amount of HCl to be added to various volumes of Refold buffer to achieve a pH around 10.4.

TABLE 1

| volumes of 12M HCl to add to refold buffer to obtain a pH of about 10.4 | | |
| --- | --- | --- |
| Volume of solubilization buffer | Volume of refold buffer at 1:3 dilution | Volume of 12.0M HCl to add to refold buffer prior to dilution |
| 1 ml | 3 ml | 5.67 µl |
| 250 ml | 750 ml | 1.42 ml |
| 750 ml | 2.25 L | 4.25 ml |
| 1 L | 3 L | 5.67 ml |

Solubilization was conducted as follows. Mixing of inclusion body suspension was initiated on a stir plate. The 300 ml of solubilization buffer were added to the mixing IB suspension and a timer was started.

Mixing of the 900 ml of refold buffer was initiated at 2 minutes.

After 2.5 minutes of mixing the IB suspension with the solubilization buffer, the mixing solubilization solution (or solubilization reaction) appeared transparent and there were no intact IBs present in the solution.

The solubilization reaction was then poured into the mixing refold buffer as quickly as possible (<5 seconds). Mixing was continued for 30 seconds after the solubilization reaction was added so that complete mixing of the two solutions was accomplished.

The refold reaction was then removed from the stir plate and allowed to sit static at room temperature for 1 hour. After 1 hour the refold reaction was placed back on the stir plate and mixing was again initiated. Once mixing occurred, 380 ml of a 0.1M HCl solution was added to the refold reaction as quickly as possible (<5 seconds). Refolding was accomplished at this point, and the refolded protein can be loaded onto protein A for purification.

Example 8: Refolding of a $^{10}$Fn3/Fc Protein

This Example describes a method for solubilizing and refolding denatured proteins in the absence of a denaturing agent.

Cell paste from the induction phase of fermentation of an *E. coli* culture expressing the $^{10}$Fn3/Fc protein of Example 6 was removed from −80° C. storage and suspended in 20 mM Sodium Phosphate pH 6.2, 250 mM Sodium Chloride, 5 mM EDTA at a ratio of 1:10 (W/W solids/buffer) using an UltraTurrax. The suspended material was passed through a microfluidizer twice at a psi of 18,000. The disrupted suspension was centrifuged at 10,000×g for 30 minutes to isolate the insoluble fraction. This fraction was resuspended, washed, and isolated twice. Wash Buffer was 20 mM Sodium Phosphate pH 6.2, 250 mM Sodium Chloride, 5 mM EDTA, 1% Triton X-100. The isolation was performed via centrifugation 10,000×g. The remaining insoluble fraction was then washed twice more in DI water. Isolation was performed via centrifugation at 10,000×g for 30 minutes. The isolated insoluble fraction (IBs) was stored at −20° C.

The $^{10}$Fn3/Fc protein fusion in the IBs was refolded as follows. Frozen IBs were thawed in RODI water. Once the IB solution was fully homogenous, the IBs were resolubilized by dilution with 50 mM Tris 0.4M Arginine pH 12.2 with stirring. This solution was left stirring for 2-5 minutes, until fully dissolved and no large particles were visible. After solubilization, the sample was diluted further with the addition of 50 mM Tris 0.4M Arginine pH 10.4, with the extra addition of 12M HCl to bring the pH of the solution to 10.4. To refold the protein, a redox reaction was performed using a 1 mM:0.2 mM oxidized to reduced ratio of Glutathione. Redox reaction was left for 1 hour at room temperature. After 1 hour, the pH of the reaction was dropped to about pH 8.0 with the addition of 0.3× volume of 1M HCl.

Example 9: Effect of Protein Concentration on Efficiency of High pH Solubilization and Refolding This Example shows that the high pH method for solubilizing and refolding denatured protein can be used with concentrations of proteins of up to at least 7 mg/ml.

Figure 7:
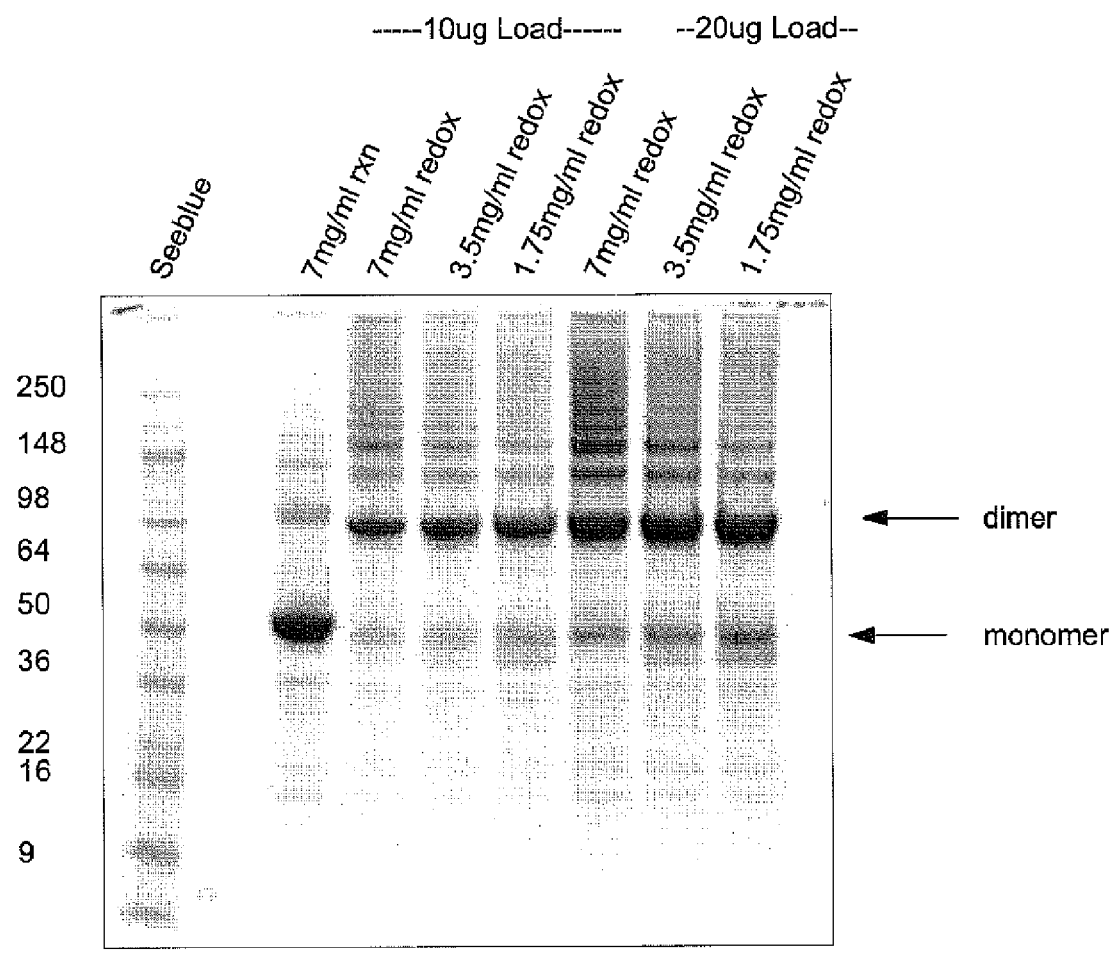
FIG. 7 shows high pH solubilization for refolding $^{10}$Fn3/Fc at 1.75, 3.5 and 7 mg/ml with either a 10 μg load (lanes 1-4) or 20 μg load (lanes 5-7).

The high pH solubilization method described Examples 7 and 8 was used for refolding $^{10}$Fn3/Fc protein (used in Examples 5 and 7) at 1.75, 3.5 and 7 mg/ml. Protein concentration was determined at the solubilization stage and adjusted for the later dilution. The concentration was measured by absorbance at 280 nm. 10 or 20 μg of refolded protein were subjected to SDS-PAGE analysis. The gel, which is shown in FIG. 7, indicates that dimer formation occurred at each of these concentrations. Therefore, concentrations of protein up to at least 7 mg/ml at the solubilization stage can be refolded using this method. Dimer formation was, however, more efficient at lower refold concentrations.

Example 10: Control of Deamidation that Occurs at High pH

A concern with using high pH to solubilize and refold $^{10}$Fn3/Fcs is deamidation of the protein. This Example shows that limiting the time of incubation at high pH for solubilization reduces deamidation.

In early experiments, solubilization at pH 12.2 as described in Examples 7 and 8 was conducted for one hour at room temperature and the refold (at pH 10.4) was incubated overnight at room temperature. The refold showed Iso-asp formation at a level of 28.1% and 17.8% deamidation by lys-C digestion followed by peptide map analysis.

To try to reduce deamidation levels, a solubilization and refold performed as in Examples 7 and 8 with the $^{10}$Fn3/Fc protein of Example 5 was conducted with a solubilization time of 5 minutes and a refold of 18-20 hours at pH of 10.4. The refolded protein showed only 5.6% iso-asp, 3.7% deamidation and 2.7% imide by lys-C peptide map.

Thus, by minimizing exposure to both pH 12.2 during the solubilization and pH 10.4 in the refold buffer, deamidation was minimized. The high pH solubilization and refolding method may provide more control over refolding time and therefore deamidation, considering that chemical denaturant removal is not required and simply reducing the pH will reduce deamidation.

Example 11: Determination of pH of Solubilization and Refold Reactions

This Example describes the pH of the solubilization and refold reactions when performing the solubilization and refold method described in Examples 7 and 8.

The $^{10}$Fn3/Fc protein used in Examples 6 and 7 was expressed in *E. coli* and IBs were obtained. 0.5 grams of IBs were suspended in 1 ml of Milli Q water. The suspension was mixed until a uniform appearance was observed and then placed aside.

Solubilization buffer was prepared by adding 46.6 μl of 12.5M NaOH to 10 mls of 50 mM Tris, 0.4 M Arginine pH 10.4. The final pH of this solubilization buffer was 12.3.

A total of 0.0305 g of oxidized glutathione and 0.003 g of reduced glutathione was added to 30 ml of 50 mM Tris, 0.4 M Arginine pH 10.4. The final pH of this refold buffer was 10.4.

A total of 56.7 μl of 12.0 M HCl was spiked into the refold buffer containing glutathione.

The entire 10 ml of solubilization buffer was added to the IB suspension. After 3 minutes, the mixing solubilization solution appeared transparent and there were no intact IBs present in the solution. The pH of this solubilization reaction was 12.5.

The solubilization reaction was then poured into the mixing refold buffer as quickly as possible (less than 5 seconds). Mixing was continued for 30 seconds after the solubilization reaction was added so that complete mixing of the two solutions was accomplished. The pH of this refold reaction was 10.3.

All steps of the method described in this Example were performed at room temperature.

Thus, the pH of the solubilization and refold reactions vary slightly from the pH of the solubilization and refold buffers, respectively. The pH of the solubilization reaction was pH 12.05, compared to the buffer, which was 12.3.

The pH of the refold reaction is also affected by the protein in solution. The pH of the refold reaction was measured at 10.3. Fc dimerization should be effective for any pH above 10.0, although a pH of as low as 9.0 can be used, although at such a pH protein aggregation may occur.

Example 12: Comparison of Target Binding of Refolded and Mammalian Expressed $^{10}$Fn3/Fc Protein This experiment shows that a $^{10}$Fn3/Fc protein that was expressed in *E. coli* and refolded as described herein binds similarly to its target protein relative to the same protein that was expressed in mammalian cell culture.

A $^{10}$Fn3-$^{10}$Fn3-Fc (i.e., a bispecific molecule having two $^{10}$Fn3 entities binding to two different targets) protein was expressed both in *E. coli* and refolded essentially as described in Example 8 and 9. The same protein was also expressed in mammalian cells HEK293-6E. Binding of both $^{10}$Fn3 entities to their target was determined by SPR. The following format was used. Protein A was covalently linked to a chip. 1.5 nM $^{10}$Fn3-$^{10}$Fn3-Fc was captured on the protein A. Binding to one of the two target proteins was measured by SPR. 0.15-5 nM of the target was used.

Figures 8A, 8B:
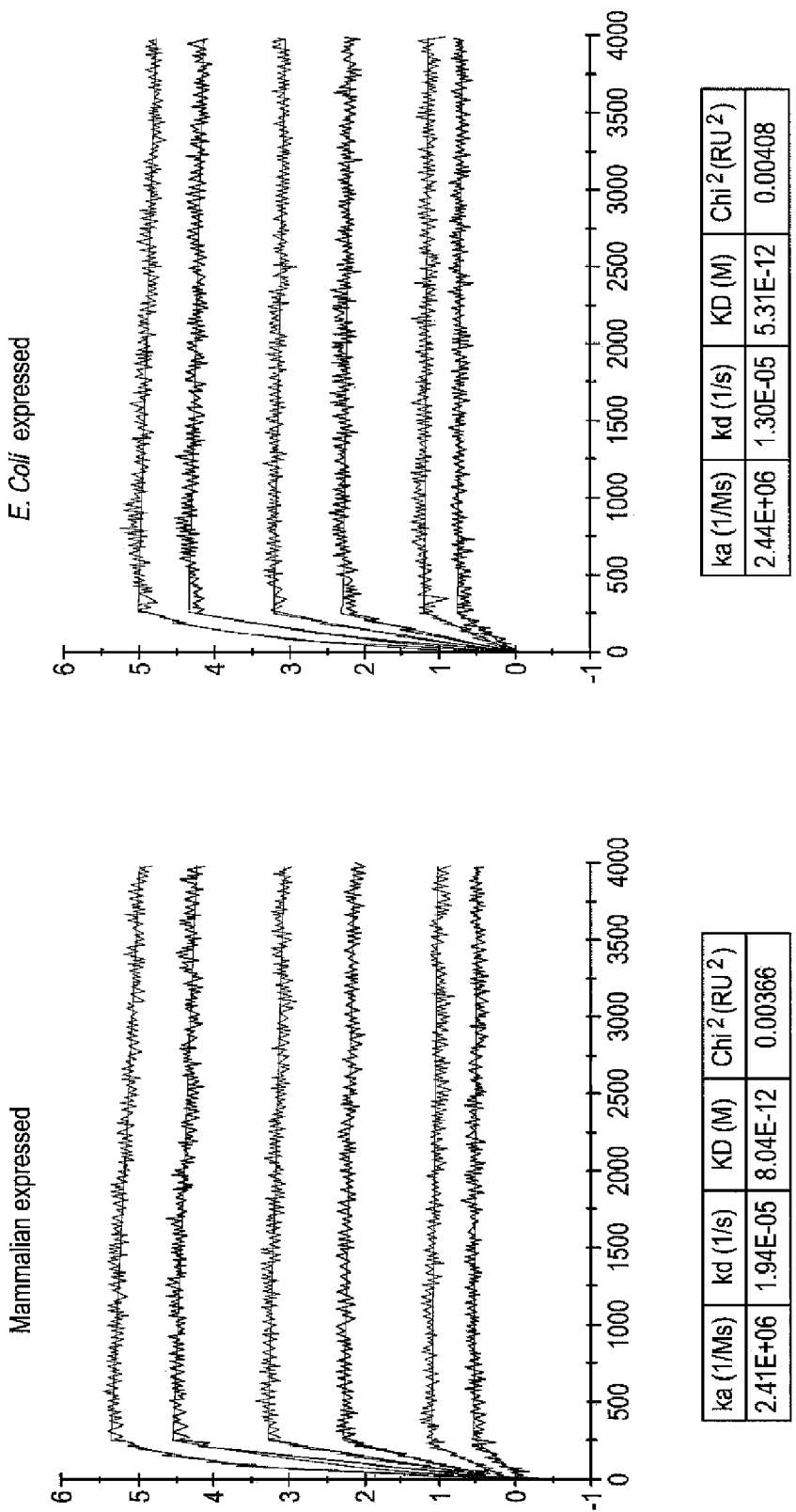
FIGS. 8A and 8B show SPR binding data of (FIG. 8A) mammalian expressed and (FIG. 8B) E. coli expressed and refolded $^{10}$Fn3/Fc protein. The Tables below the diagrams provide the ka, kd and KD values for each protein.

The results, which are shown in FIGS. 8A and B, indicate that the $^{10}$Fn3-$^{10}$Fn3-Fc protein expressed in *E. coli* and refolded has similar target binding kinetics to those of the $^{10}$Fn3-$^{10}$Fn3-Fc protein that was expressed in mammalian cells. Thus, $^{10}$Fn3/Fc proteins expressed in *E. coli* and refolded as described herein is at least sufficiently refolded to allow binding to its target.

Example 13: Comparison of Inhibition of Biological Activity of Refolded and Mammalian Expressed $^{10}$Fn3/Fc Protein This Example shows that a $^{10}$Fn3/Fc protein that was expressed in *E. coli* and refolded as described herein has similar biological activity relative to the same protein that was expressed in mammalian cell culture.

In this experiment mice are injected with the bispecific $^{10}$Fn3-$^{10}$Fn3-Fc of Example 12 made either in *E. coli* or in mammalian cells, and the level of activity of the $^{10}$Fn3-$^{10}$Fn3-Fc molecule was determined by determining the level of inhibition of the biological activity of the target. The mammalian protein was produced in a mammalian shake flask culture or in a mammalian bioreactor. For comparison purposes, the experiment also included an antibody to one of the two targets and a the adnectin binding to one of the targets alone (i.e. a mono-adnectin). Different concentrations of each were tested. Three different biological activities of the target protein were tested: two of the activities consisted of the induced secretion of two different cytokines and the third biological activity of the target protein was stimulation of signal transduction.

Figure 9:
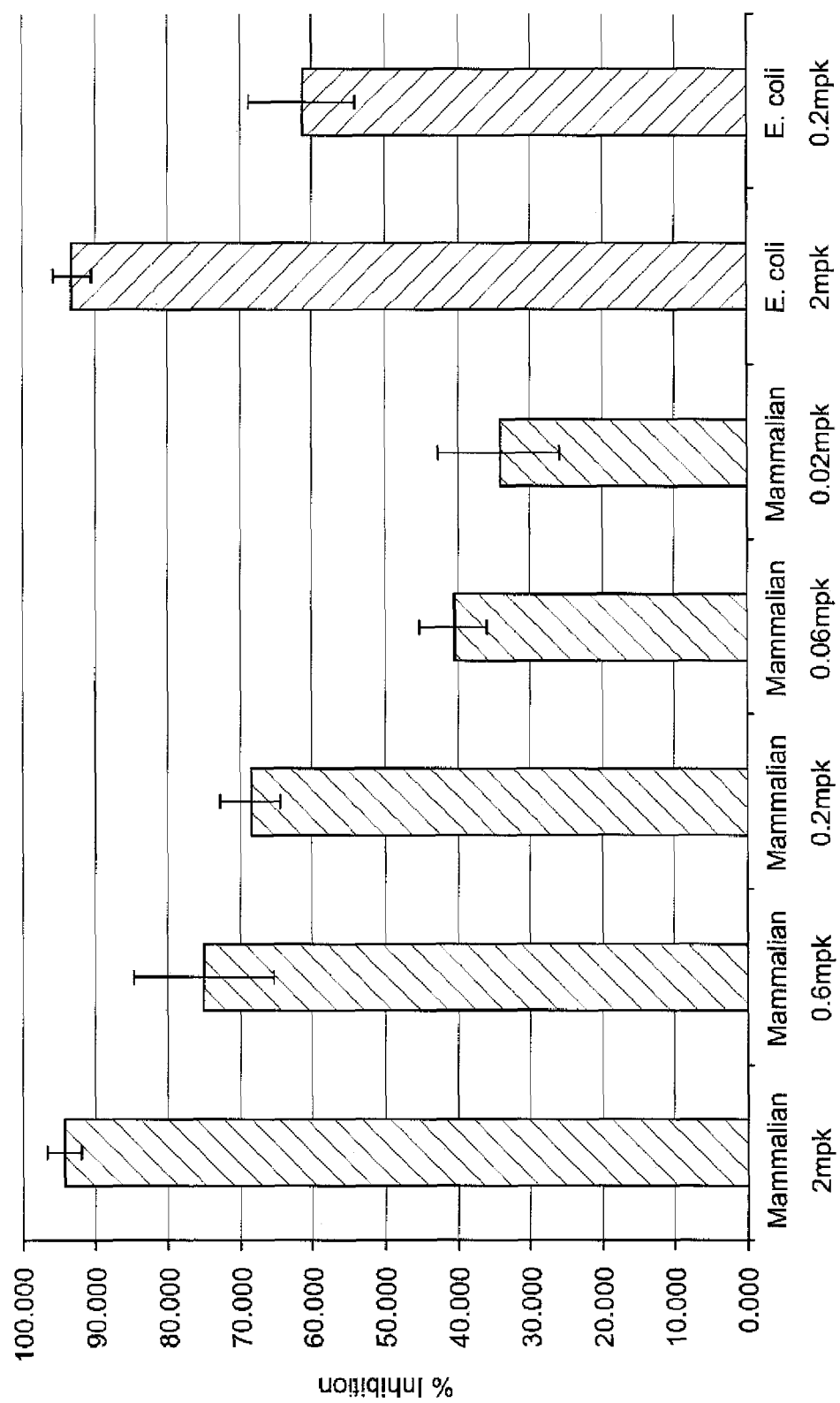
FIG. 9 shows the percent inhibition in mice of target induced cytokine secretion by various amounts of E. coli expressed and refolded, or mammalian expressed, $^{10}$Fn3/Fc protein, indicating that similar levels of inhibition are obtained with the E. coli expressed and refolded protein relative to the mammalian expressed protein. "mpk" refers to milligrams of protein per weight of the animal in kg.
Figure 10:
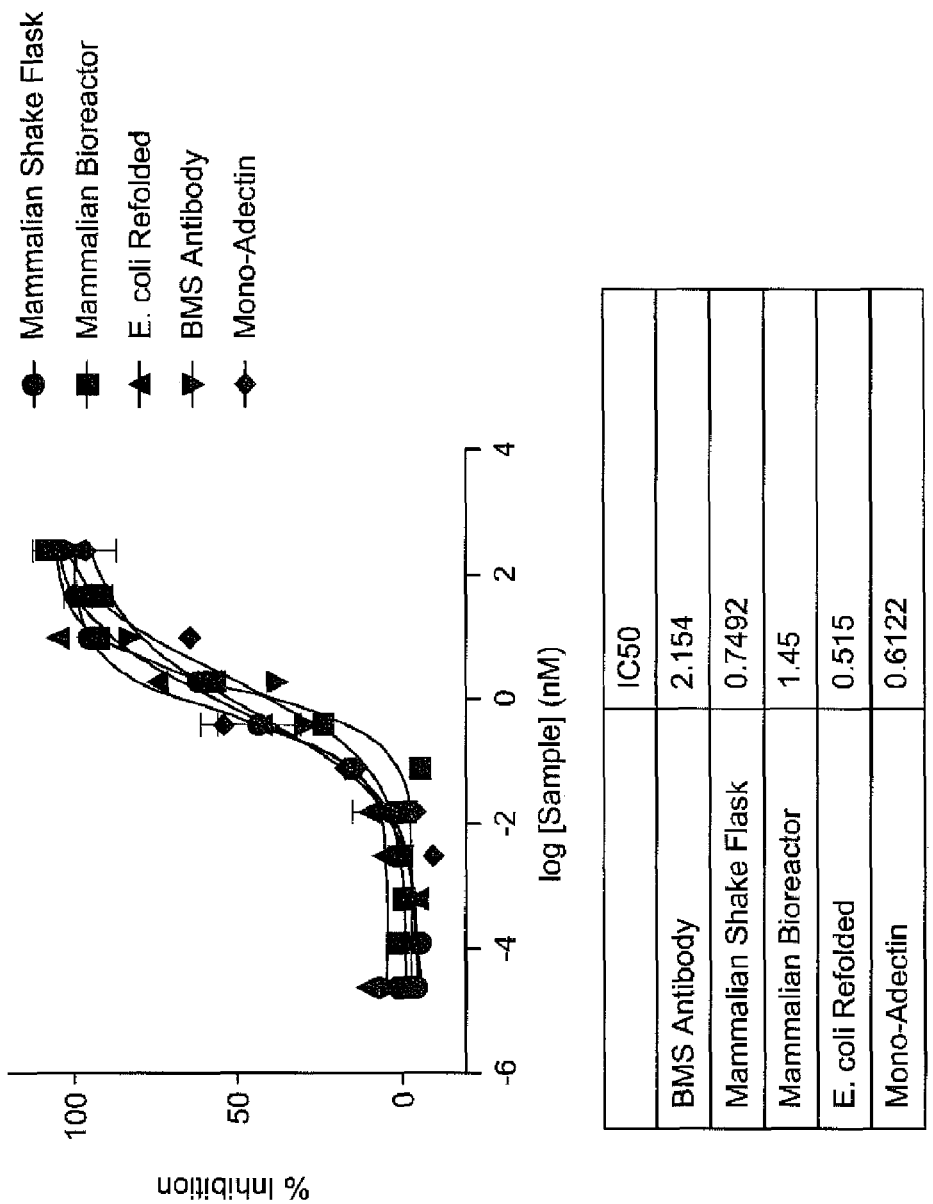
FIG. 10 shows the percent inhibition in mice of target induced cytokine (different from that in FIG. 9) secretion by various amounts of E. coli expressed and refolded $^{10}$Fn3/Fc protein ("E. coli Refolded"), or $^{10}$Fn3/Fc protein expressed in mammalian cells in a shake flask culture ("Mammalian Shake Flask), or bioreactor ("Mammalian Bioreactor"). Also shown is the percent inhibition obtained with an antibody ("BMS Antibody") binding to the same target as one of the targets of the $^{10}$Fn3/Fc molecule, as well as inhibition by one of the two $^{10}$Fn3 entities on its own ("mono-adnectin").

Inhibition of the secretion of one cytokine is shown in FIG. 9. The results indicate that the $^{10}$Fn3-$^{10}$Fn3-Fc protein expressed in *E. coli* and refolded as described herein inhibit cytokine secretion induced by the target to a similar level. A similar result was seen when measuring the level of inhibition of secretion of the second cytokine (FIG. 10).

Figure 11:
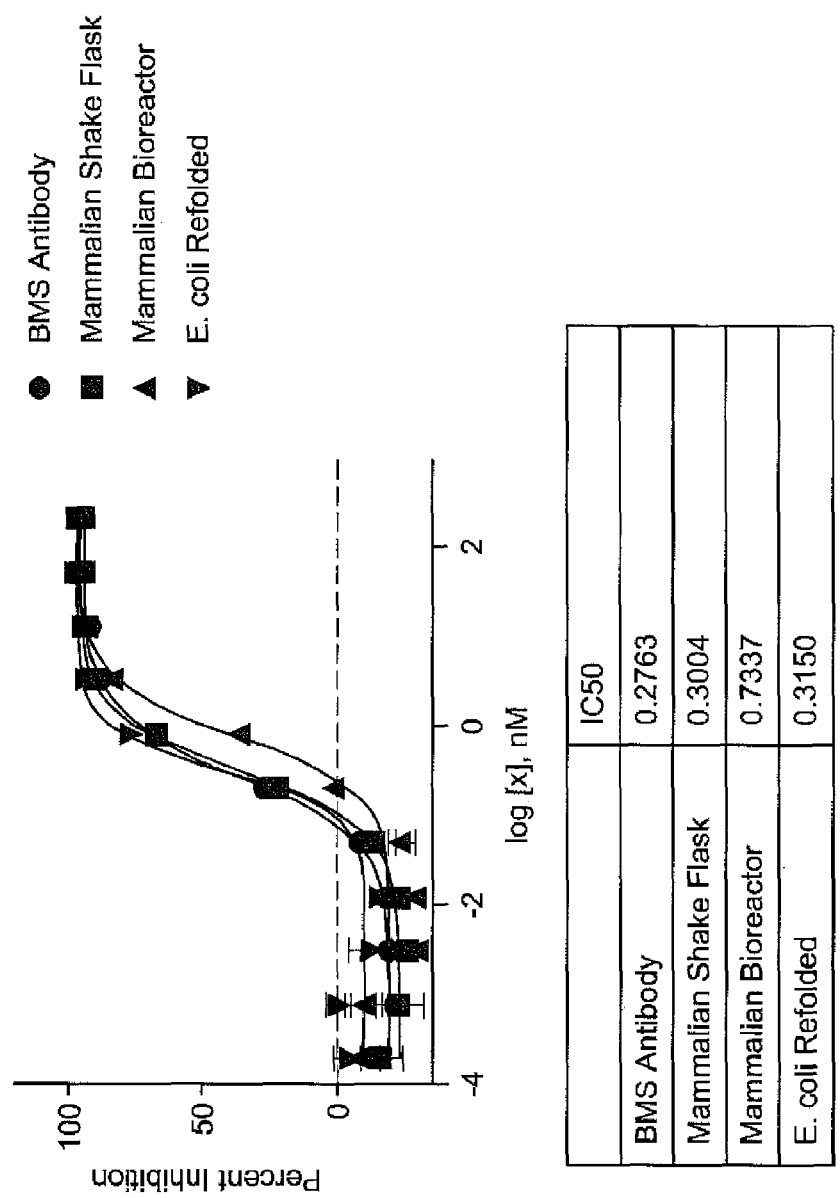
FIG. 11 shows the percent inhibition in mice of signal transduction by various amounts of E. coli expressed and refolded $^{10}$Fn3/Fc protein ("E. coli Refolded"), or $^{10}$Fn3/Fc protein expressed in mammalian cells in a shake flask culture ("Mammalian Shake Flask), or bioreactor ("Mammalian Bioreactor"). Also shown is the percent inhibition obtained with an antibody ("BMS Antibody") binding to the same target as one of the targets of the $^{10}$Fn3/Fc molecule.

Inhibition of signal transduction is shown in FIG. 11. The results indicate that the $^{10}$Fn3-$^{10}$Fn3-Fc protein expressed in *E. coli* and refolded as described herein inhibit signal transduction induced by the target to a similar level.

Thus, these results taken together with those of Example 12 indicate that the $^{10}$Fn3-$^{10}$Fn3-Fc protein expressed in *E. coli* and refolded as described herein is at least sufficiently refolded to have biological activity that is similar to that of the same protein expressed in a mammalian cell culture system.

The entire disclosures of each document cited (including patents, patent applications, journal articles, abstracts, laboratory manuals, books, GENBANK® Accession numbers, SWISS-PROT® Accession numbers, or other disclosures) in the instant patent application, including the Background, Detailed Description, Brief Description of the Drawings, and Examples, are hereby incorporated herein by reference in their entirety.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method for refolding a denatured protein, comprising combining a composition comprising suspended denatured proteins with a solubilization buffer having a pH in the range of 10.5 to 13 to thereby obtain a composition comprising solubilized denatured proteins; and combining the composition comprising solubilized denatured proteins with a refold buffer having a pH in the range of 9 to 11 to thereby obtain a composition comprising refolded proteins;
wherein the method does not include the use of a denaturing agent.

2. The method of claim 1, wherein the composition comprising suspended denatured proteins is combined with solubilization buffer at a ratio of weight (g) of denatured proteins:volume (ml) of solubilization buffer of 1:10-30.

3. The method of claim 1, wherein the composition comprising solubilized denatured proteins is combined with refold buffer at a ratio of volume of solubilization buffer:volume of refold buffer of 1:1-5.

4. The method of claim 1, wherein
the composition comprising suspended denatured proteins is combined with solubilization buffer at a ratio of weight (g) of denatured proteins:volume (ml) of solubilization buffer of 1:10-30; and
the composition comprising solubilized denatured proteins is combined with refold buffer at a ratio of volume of solubilization buffer:volume of refold buffer of 1:1-5.

5. The method of claim 4, wherein the solubilization buffer has a pH in the range of 11.5 to 12.8 and the refold buffer has a pH in the range of 10 to 10.9.

6. The method of claim 1, wherein the composition comprising suspended denatured proteins and the solubilization buffer are combined for 1-10 minutes prior to being combined with the refold buffer.

7. The method of claim 1, wherein the composition comprising the solubilized denatured proteins is combined with the refold buffer for 5-60 minutes.

8. The method of claim 1, wherein the solubilization buffer comprises Arginine.

9. The method of claim 1, wherein the refold buffer comprises Arginine.

10. The method of claim 1, wherein the refold buffer comprises an oxidizing agent.

11. The method of claim 1, wherein the denatured proteins are in the form of inclusion bodies (IBs).

12. The method of claim 1, wherein the protein comprises an Fc region.

13. The method of claim 12, wherein the protein comprises a binding domain that specifically binds to a target protein, and wherein the binding domain is an alternative scaffold binding domain.

14. The method of claim 13, wherein the alternative scaffold binding domain is a fibronectin based scaffold domain.

* * * * *